United States Patent
Bartlett et al.

(10) Patent No.: US 11,919,869 B2
(45) Date of Patent: Mar. 5, 2024

(54) CD73 COMPOUNDS

(71) Applicant: Gilead Sciences, Inc., Foster City, CA (US)

(72) Inventors: Mark J. Bartlett, Castro Valley, CA (US); Gregory F. Chin, San Francisco, CA (US); Michael O. Clarke, Redwood City, CA (US); Jennifer L Cosman, Foster City, CA (US); Deeba Ensan, Foster City, CA (US); Bindu Goyal, Fremont, CA (US); Stephen Ho, Redwood City, CA (US); Richard L Mackman, Millbrae, CA (US); Michael R. Mish, Foster City, CA (US); Dustin S. Siegel, Half Moon Bay, CA (US); Kyle C. Tamshen, Oakland, CA (US); Hai Yang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/050,404

(22) Filed: Oct. 27, 2022

(65) Prior Publication Data
US 2023/0183189 A1    Jun. 15, 2023

Related U.S. Application Data

(60) Provisional application No. 63/273,454, filed on Oct. 29, 2021.

(51) Int. Cl.
*C07D 247/00* (2006.01)
(52) U.S. Cl.
CPC .................. *C07D 247/00* (2013.01)
(58) Field of Classification Search
None
See application file for complete search history.

(56) References Cited

U.S. PATENT DOCUMENTS

2023/0039553 A1    2/2023    Bartlett et al.

FOREIGN PATENT DOCUMENTS

| CN | 1592624 A | 3/2005 |
|---|---|---|
| WO | WO-2011031979 A1 | 3/2011 |
| WO | WO-2011082270 A2 | 7/2011 |
| WO | WO-2012005805 A1 | 1/2012 |
| WO | WO-2019168744 A1 | 9/2019 |
| WO | WO-2021222522 A1 | 11/2021 |
| WO | WO-2022/068929 A1 | 4/2022 |

OTHER PUBLICATIONS

Intl. Search Report-Written Opinion dated Feb. 9, 2023 for Intl. Appl. No. PCT/US2022/078822, 12 pages.
Intl. Search Report-Written Opinion dated Jul. 12, 2021 for Intl. Appl. No. PCT/US2021/029828, 9 pages.
Office Action dated Apr. 6, 2022 for Taiwanese Appl. No. 110115754, 6 pages.
Office Action dated Jan. 12, 2023 for Panamanian Appl. No. PI/2022/94196-01, 2 pages.
Examination Report dated Feb. 22, 2023 for Indian Appl. No. 202217063551, 6 pages.
International Preliminary Report on Patentability dated Oct. 27, 2022 for Intl. Appl. No. PCT/US2021/029828, 7 pages.
Examination Report dated Apr. 19, 2023 for Australian Appl. No. 2021264550, 2 pages.
Office Action dated Jun. 12, 2023 for Taiwanese Appl. No. 111141131, 8 pages.

*Primary Examiner* — Samantha L Shterengarts

(57) ABSTRACT

Provided herein is A compound of Formula I:

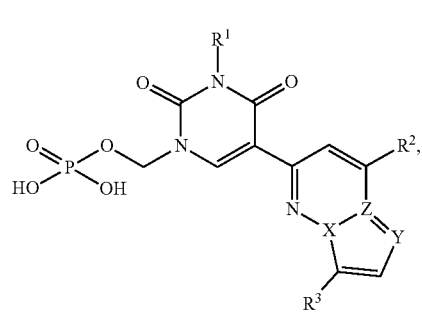

or a pharmaceutically acceptable salt thereof, wherein the various substituents are described herein.

27 Claims, 2 Drawing Sheets

CD73 COMPOUNDS

CROSS-REFERENCES TO RELATED APPLICATIONS

This application claims the benefit of priority to U.S. Provisional Patent Application No. 63/273,454, filed 29 Oct. 2021 and titled "CD73 Compounds," the entirety of which is incorporated by reference herein.

BACKGROUND OF THE INVENTION

The glycosyl-phosphatidylinositol-anchored CD73 antigen (also known as Cluster of Differentiation 73, ecto-5'-nucleotidase, ecto-5'-NT, 5'-NT, and NT5E) is considered the rate-limiting enzyme in the generation of extracellular adenosine (Stagg J, Smyth MJ. Extracellular adenosine triphosphate and adenosine in cancer. Oncogene. 2010; 29:5346-58. doi:10.1038/onc.2010.292). CD73 is a 70-kDa glycosylphosphatidylinositol (GPI)-anchored protein normally expressed on endothelial cells and subsets of hematopoietic cells. CD73, together with CD39, regulates adenosine triphosphate (ATP) metabolism. CD39 (NTP-Dase-1) converts ATP into AMP, with only trace amounts of ADP being released, while CD73 catalyzes the conversion of AMP to adenosine (Ado).

Extracellular Ado accumulates in cancerous tissues and constitutes an important mechanism of tumor immune escape. Among other effects, tumor-derived Ado profoundly inhibits infiltrating effector T cells. ATP degradation into Ado through CD39 and CD73 co-expressed on murine Treg (regulatory CD4+ T cells) has been shown as responsible for tumor immunosuppression.

CD73 can be found constitutively expressed at high levels on various types of cancer cells. CD73-generated adenosine is assumed to suppress adaptive anti-tumor immune responses thereby promoting tumor growth and metastasis. And studies in animal models have shown that blockade of CD73 activity suppresses tumor growth and prolongs survival by promoting anti-tumor adaptive immunity (Forte et al. (2012) J Immunol. 189(5):2226-33). Given the need for cancer treatments, new compositions and methods for regulating CD73 activity and related therapeutic agents is needed. This disclosure meets this and other needs.

BRIEF SUMMARY OF THE INVENTION

In one embodiment, the present disclosure provides a compound of Formula I:

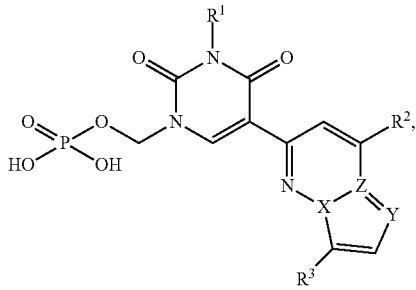

or a pharmaceutically acceptable salt thereof, wherein:
X is C or N,
Y is CH or N;
Z is C or N;
provided that one of X, Y and Z is CH or C, and two of X, Y and Z are N;
$R^1$ is selected from H and $CH_2OP(O)(OH)_2$;
$R^2$ is a $C_{3-6}$ cycloalkyl or a 3-8 membered heterocyclyl; wherein said cycloalkyl and said heterocyclyl are substituted with one or more $R^4$,
$R^3$ is H or halo;
$R^4$ is independently selected from H, halo, $C_{1-4}$ alkyl, $-OR^5$, $C_{6-10}$ aryl, or 4-10 membered heteroaryl; wherein said $C_{1-4}$ alkyl, $C_{6-10}$ aryl, or 4-10 membered heteroaryl is optionally substituted with one or more $R^6$;
$R^5$ is $C_{1-5}$ alkyl, $C_{1-5}$ alkenyl, $C_{1-5}$ alkynyl, said $C_{1-5}$ alkyl, $C_{1-5}$ alkenyl, $C_{1-5}$ alkynyl, $C_{6-10}$ aryl, or 4-10 membered heteroaryl and is optionally substituted with one or more $R^6$ and halo;
$R^6$ is a $C_{1-5}$ alkyl, $C_{3-6}$ cycloalkyl, $C_{1-5}$ alkenyl, $C_{1-5}$ alkynyl, or 4-10 membered heteroaryl, said $C_{1-5}$ alkyl, $C_{3-6}$ cycloalkyl, $C_{1-5}$ alkenyl, or $C_{1-5}$ alkynyl is optionally substituted with halo, and said 4-10 membered heteroaryl optionally substituted with $C_{1-4}$ alkyl, or $C_{1-4}$ haloalkyl.

In some embodiments, $R^1$ is H. In other embodiments, $R^1$ is $CH_2OP(O)(OH)_2$.

In some embodiments, $R^2$ is a $C_{3-6}$ cycloalkyl, substituted with one or more $R^4$.

In other embodiments, $R^2$ is a 3-8 membered heterocyclyl substituted with one or more $R^4$.

DETAILED DESCRIPTION OF THE INVENTION

I. Examples

Figure 1:
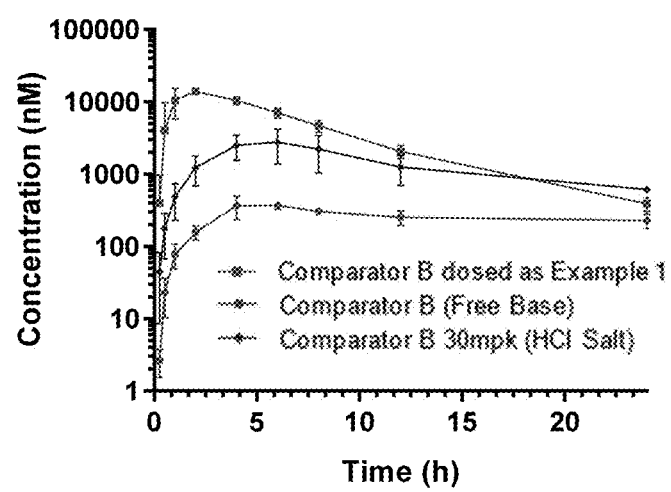
FIG. 1 shows plasma concentrations of Compound Comparator B (nM) during a 24 hour time period after dosing with either Comparator B or Example 1.

Abbreviations. Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Definition |
| --- | --- |
| Ac | acetate |
| Ar | argon |
| ACN | acetonitrile |
| cat | catalyst |
| DCM | dichloromethane |
| DIPEA | N,N-diisopropylethylamine |
| DMSO | dimethylsulfoxide |
| DMF | dimethylformamide |
| ES/MS | electrospray mass spectrometry |
| Et | ethyl |
| EtOAc | ethyl acetate |
| HPLC | high performance liquid chromatography |
| LC | liquid chromatography |
| Me | methyl |

TABLE 1-continued

List of abbreviations and acronyms.

| Abbreviation | Definition |
| --- | --- |
| MeCN | acetonitrile |
| m/z | mass to charge ratio |
| NMP | N-methyl-2-pyrrolidone |
| NMR | Nuclear Magnetic Resonance |
| Ph | phenyl |
| Pd(dppf)Cl$_2$ or PdCl$_2$(dppf) | [1,1'-Bis(diphenylphosphino)ferrocene]dichloropalladium(II) |
| Pr | propyl |
| RP | reverse phase |
| TFA | trifluoroacetic acid |
| THF | tetrahydrofuran |
| TBHP | tert-butyl hydroperoxide |
| δ | parts per million referenced to residual non-deuterated solvent peak |

General Procedure 1

Preparation of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate

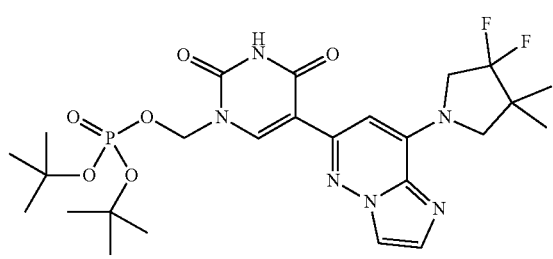 [SMILES: CC(C)(C)OP(=O)(OCn1cc(-c2cc(N3CC(C)(C)C(F)(F)C3)c3nccn3n2)c(=O)[nH]c1=O)OC(C)(C)C]

To a solution of 5-(8-(3,3-difluoro-4,4-dimethylpyrrolidin-1-yl)imidazo[1,2-b]pyridazin-6-yl)pyrimidine-2,4(1H,3H)-dione (500 mg, 1.38 mmol, 1 equiv) and triethylamine (0.67 Ml, 4.83 mmol, 3.5 equiv) in DMF (16 Ml) was added di-tert-butyl (chloromethyl) phosphate (1.07 g, 4.14 mmol, 3 equiv). The reaction mixture was heated to 60° C. and stirred for 16 h. Another aliquot of di-tert-butyl (chloromethyl) phosphate (1.07 g, 4.14 mmol, 3 equiv) and triethylamine (0.67 Ml, 4.83 mmol, 3.5 equiv) were added and the reaction stirred for another 16 hours. The reaction mixture was subsequently diluted with EtOAc/water, extracted twice with EtOAc. The combined organic layers were dried over MgSO4, filtered and concentrated in vacuo. The crude product was purified by silica chromatography (100% EtOAc) to provide di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate Preparation of (5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl dihydrogen phosphate

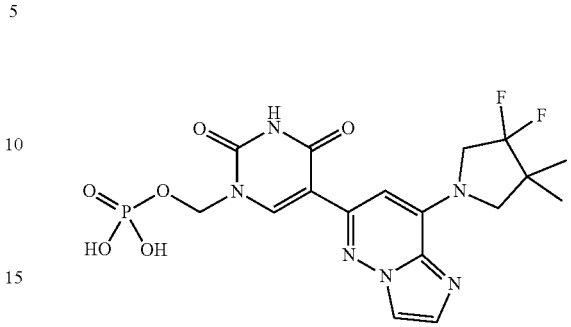

To a solution of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate (671 mg, 1.15 mmol, 1 equiv) in DCM (15 mL) was added TFA (5 mL). The reaction mixture was stirred at room temperature for 15 min before being concentrated in vacuo and purified by HPLC (10-80% MeCN/water with TFA). LC-MS m/z: 473.1 (M+1). 1H NMR (400 MHz, DMSO-d6) δ 11.79 (s, 1H), 8.25 (s, 1H), 8.08 (d, J=1.2 Hz, 1H), 7.59 (d, J=1.2 Hz, 1H), 6.54 (s, 1H), 5.53 (d, J=10.7 Hz, 2H), 4.41 (s, 2H), 3.86 (s, 2H), 1.21 (s, 6H). 19F NMR (376 MHz, DMSO-d6) δ −115.33 (m, 2F). 31P NMR (162 MHz, DMSO-d6) δ −2.24 (t, J=10.6 Hz, 1P).

The following compounds were prepared in an analogous manner to (5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl dihydrogen phosphate using the modifications listed below:

di-tert-butyl ((2,4-dioxo-5-(8-((1S,2S)-2-(1-(2,2,2-trifluoroethyl)-1H-indazol-6-yl)cyclopropyl)imidazo[1,2-b]pyridazin-6-yl)-3,4-dihydropyrimidin-1(2H)-yl)methyl) phosphate was prepared using 5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride in place of 5-(8-(3,3-difluoro-4,4-dimethylpyrrolidin-1-yl)imidazo[1,2-b]pyridazin-6-yl)pyrimidine-2,4(1H,3H)-dione

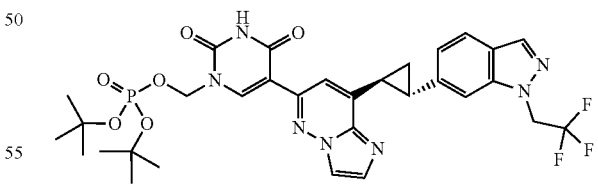

5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione was prepared using di-tert-butyl ((2,4-dioxo-5-(8-((1S,2S)-2-(1-(2,2,2-trifluoroethyl)-1H-indazol-6-yl)cyclopropyl)imidazo[1,2-b]pyridazin-6-yl)-3,4-dihydropyrimidin-1(2H)-yl)methyl) phosphate in place of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate

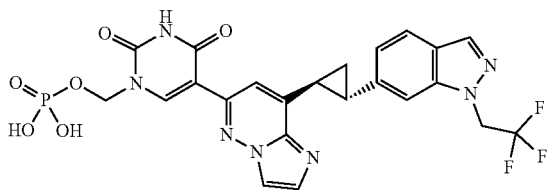 [SMILES: O=c1[nH]c(=O)n(COP(=O)(O)O)cc1-c1cc([C@H]2C[C@@H]2c2ccc3cnn(CC(F)(F)F)c3c2)c2nccn2n1]

LC-MS m/z: 578.1 (M+1). 1H NMR (400 MHz, DMSO-d6) δ 11.90 (s, 1H), 8.33 (s, 1H), 8.28 (d, J=1.3 Hz, 1H), 8.16 (d, J=0.9 Hz, 1H), 7.77-7.66 (m, 3H), 7.49 (s, 1H), 7.13 (dd, J=8.6, 1.2 Hz, 1H), 5.56 (d, J=10.8 Hz, 2H), 5.41 (q, J=9.1 Hz, 2H), 3.09-3.00 (m, 1H), 2.81 (dt, J=9.6, 5.2 Hz, 1H), 2.19 (dt, J=9.4, 5.1 Hz, 1H), 1.89 (dt, J=9.4, 5.3 Hz, 1H). 19F NMR (376 MHz, DMSO-d6) δ −70.08 (t, J=9.1 Hz, 3F). 31P NMR (162 MHz, DMSO-d6) δ −2.22 (t, J=11.0 Hz, 1P).

tetra-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxopyrimidine-1,3(2H,4H)-diyl)bis(methylene)) bis(phosphate) was prepared using 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione in place of 5-(8-(3,3-difluoro-4,4-dimethylpyrrolidin-1-yl)imidazo[1,2-b]pyridazin-6-yl)pyrimidine-2,4(1H,3H)-dione

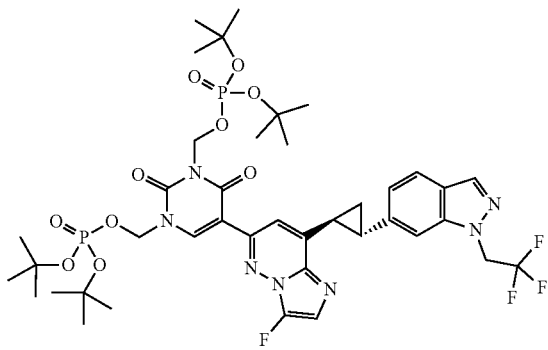 [SMILES: CC(C)(C)OP(=O)(OCn1cc(-c2cc([C@H]3C[C@@H]3c3ccc4cnn(CC(F)(F)F)c4c3)c3ncc(F)n3n2)c(=O)n(COP(=O)(OC(C)(C)C)OC(C)(C)C)c1=O)OC(C)(C)C]

(5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxopyrimidine-1,3(2H,4H)-diyl)bis(methylene) bis(dihydrogen phosphate) was prepared using tetra-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxopyrimidine-1,3(2H,4H)-diyl)bis(methylene)) bis (phosphate) in place of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate

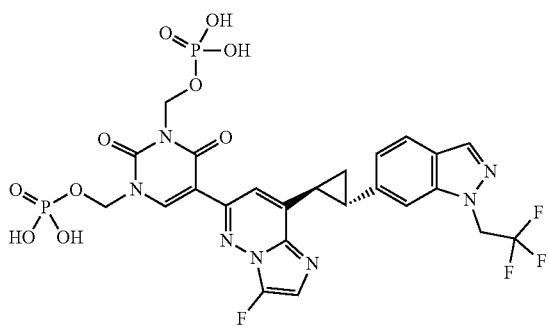 [SMILES: O=c1c(-c2cc([C@H]3C[C@@H]3c3ccc4cnn(CC(F)(F)F)c4c3)c3ncc(F)n3n2)cn(COP(=O)(O)O)c(=O)n1COP(=O)(O)O]

LC-MS m/z: 706.1 (M+1). 1H NMR (400 MHz, DMSO-d6) δ 8.45 (s, 1H), 8.15 (d, J=0.8 Hz, 1H), 7.73 (d, J=8.2 Hz, 2H), 7.60 (d, J=7.1 Hz, 1H), 7.43 (s, 1H), 7.13 (dd, J=8.4, 1.4 Hz, 1H), 5.69 (d, J=6.5 Hz, 2H), 5.64 (d, J=10.8 Hz, 2H), 5.41 (q, J=9.2 Hz, 2H), 3.02 (ddd, J=8.9, 6.3, 4.3 Hz, 1H), 2.83 (ddd, J=8.8, 5.9, 4.3 Hz, 1H), 2.21-2.09 (m, 1H), 1.91 (dt, J=8.7, 5.5 Hz, 1H). 19F NMR (376 MHz, DMSO-d6) δ −70.08 (t, J=9.1 Hz, 3F), −155.02 (d, J=7.2 Hz, 1F). 31P NMR (162 MHz, DMSO-d6) δ −2.18 (t, J=11.0 Hz, 1P), −3.44 (t, J=6.5 Hz, 1P).

General Procedure 2

Preparation of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate

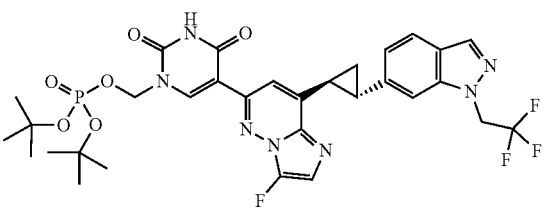 [SMILES: CC(C)(C)OP(=O)(OCn1cc(-c2cc([C@H]3C[C@@H]3c3ccc4cnn(CC(F)(F)F)c4c3)c3ncc(F)n3n2)c(=O)[nH]c1=O)OC(C)(C)C]

To a solution of 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride (100 mg, 0.192 mmol, 1 equiv) in DMAc (1 mL) was added KHCO₃ (48 mg, 0.479 mmol, 2.5 equiv) and di-tert-butyl (chloromethyl) phosphate (59.5 mg, 0.23 mmol, 1.2 equiv). The reaction mixture was heated to 60° C. and stirred for 16 h. The reaction mixture was subsequently diluted with EtOAc/water, extracted twice with EtOAc. The combined organic layers were dried over MgSO4, filtered and concentrated in vacuo. The crude product was purified by silica chromatography (100% EtOAc) to provide di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate.

Preparation of (5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl dihydrogen phosphate

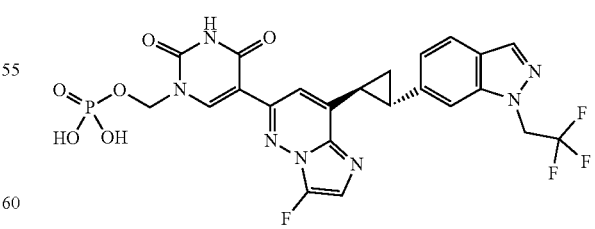

To a solution of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate (90 mg, 0.127 mmol, 1 equiv) in DCM (2.5 mL) was added TFA (0.25 mL). The reaction mixture was stirred at room temperature for 15 min before being concentrated in vacuo and purified by: HPLC (10-80% MeCN/water with TFA). LC-MS m/z: 596.1 (M+1). 1H NMR (400 MHz, DMSO-d6) δ 11.92 (s, 1H), 8.36 (s, 1H), 8.15 (s, 1H), 7.78-7.68 (m, 2H), 7.58 (d, J=7.0 Hz, 1H), 7.49 (s, 1H), 7.12 (d, J=8.5 Hz, 1H), 5.57 (d, J=10.8 Hz, 2H), 5.40 (q, J=9.1 Hz, 2H), 3.04 (ddd, J=9.3, 6.3, 4.4 Hz, 1H), 2.79 (dt, J=9.4, 5.2 Hz, 1H), 2.18 (dt, J=8.8, 5.2 Hz, 1H), 1.90 (dt, J=8.6, 5.2 Hz, 1H). 19F NMR (376 MHz, DMSO-d6) δ −70.08 (t, J=9.2 Hz, 3F), −155.18 (d, J=7.0 Hz, 1F).

The following compounds were prepared in an analogous manner to (5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl) methyl dihydrogen phosphate using the modifications listed below:

di-tert-butyl ((5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)-2,4-dioxo-3,4-dihydropyrimidin-1(2H)-yl)methyl) phosphate was prepared using 5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione in place of 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride.

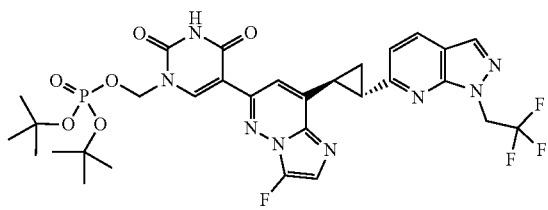 [SMILES: CC(C)(C)OP(=O)(OCn1cc(-c2cc([C@H]3C[C@@H]3c3ccc4cnn(CC(F)(F)F)c4n3)c3ncc(F)n3n2)c(=O)[nH]c1=O)OC(C)(C)C]

(5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)-2,4-dioxo-3,4-dihydropyrimidin-1(2H)-yl) methyl dihydrogen phosphate was prepared using di-tert-butyl ((5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)-2,4-dioxo-3,4-dihydropyrimidin-1(2H)-yl)methyl) phosphate in place of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate.

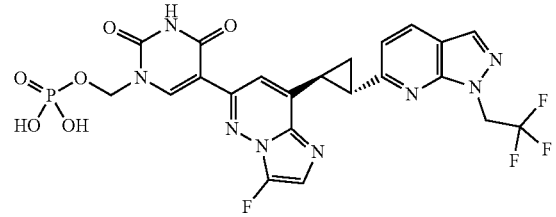 [SMILES: O=c1[nH]c(=O)n(COP(=O)(O)O)cc1-c1cc([C@H]2C[C@@H]2c2ccc3cnn(CC(F)(F)F)c3n2)c2ncc(F)n2n1]

LC-MS m/z: 597.1 (M+1). 1H NMR (400 MHz, DMSO-d6) δ 11.93 (s, 1H), 8.36 (s, 1H), 8.25 (s, 1H), 8.20 (d, J=8.3 Hz, 1H), 7.58 (d, J=7.1 Hz, 1H), 7.51 (s, 1H), 7.38 (d, J=8.3 Hz, 1H), 5.57 (d, J=10.8 Hz, 2H), 5.34 (tt, J=9.3, 4.8 Hz, 2H), 3.24 (ddd, J=8.6, 5.9, 4.1 Hz, 2H), 3.07 (ddd, J=8.9, 6.1, 4.0 Hz, 1H), 2.22 (ddd, J=8.6, 6.2, 3.9 Hz, 1H), 2.06 (ddd, J=9.4, 5.8, 3.9 Hz, 1H). 19F NMR (376 MHz, DMSO-d6) δ −69.89 (t, J=9.1 Hz, 3F), −155.18 (d, J=7.1 Hz, 1F). 31P NMR (162 MHz, DMSO-d6) δ −2.18 (t, J=10.8 Hz, 1P).

di-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)-3,4-dihydropyrimidin-1(2H)-yl)methyl) phosphate and tetra-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)pyrimidine-1,3(2H,4H)-diyl)bis (methylene)) bis(phosphate) were prepared using 5-(7-((1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione; trifluoroacetic acid in place of 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride.

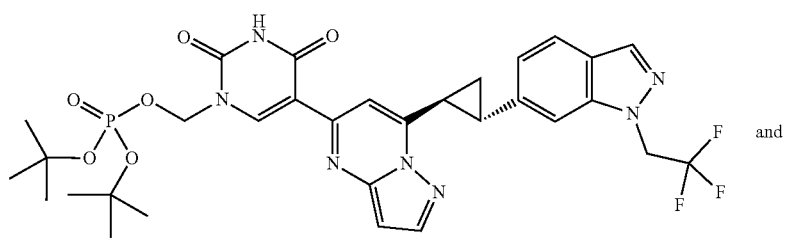

and

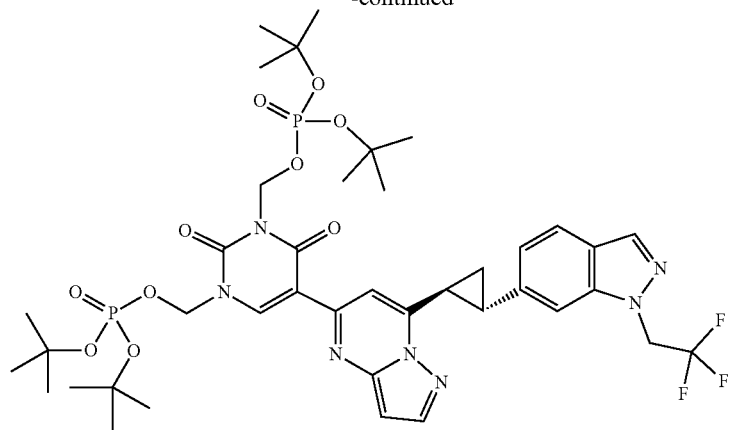

(2,4-dioxo-5-(7-((1S,2S)-2-(1-(2,2,2-trifluoroethyl)-1H-indazol-6-yl)cyclopropyl)pyrazolo[1,5-a]pyrimidin-5-yl)-3,4-dihydropyrimidin-1(2H)-yl)methyl dihydrogen phosphate was prepared using di-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)-3,4-dihydropyrimidin-1(2H)-yl)methyl) phosphate in place of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate

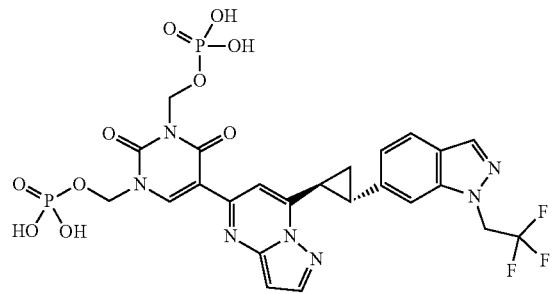 [SMILES: O=c1c(-c2cc([C@H]3C[C@@H]3c3ccc4cnn(CC(F)(F)F)c4c3)n3nccc3n2)cn(COP(=O)(O)O)c(=O)n1COP(=O)(O)O]

LC-MS m/z: 578.1 (M+1). 1H NMR (400 MHz, DMSO-d6) δ 11.91 (s, 1H), 8.68 (s, 1H), 8.21 (d, J=2.3 Hz, 1H), 8.17 (s, 1H), 7.78 (s, 1H), 7.75 (d, J=8.4 Hz, 1H), 7.68 (s, 1H), 7.20 (dd, J=8.4, 1.3 Hz, 1H), 6.70 (d, J=2.3 Hz, 1H), 5.61 (d, J=11.1 Hz, 2H), 5.42 (q, J=9.1 Hz, 2H), 3.17 (ddd, J=8.5, 6.4, 4.4 Hz, 1H), 2.82 (td, J=7.1, 4.5 Hz, 1H), 1.97 (t, J=8.2 Hz, 2H). 19F NMR (376 MHz, DMSO-d6) δ −70.06 (t, J=9.1 Hz, 3F). 31P NMR (162 MHz, DMSO-d6) δ −2.17 (t, J=11.1 Hz, 1P).

(2,4-dioxo-5-(7-((1S,2S)-2-(1-(2,2,2-trifluoroethyl)-1H-indazol-6-yl)cyclopropyl)pyrazolo[1,5-a]pyrimidin-5-yl)pyrimidine-1,3(2H,4H)-diyl)bis(methylene) bis(dihydrogen phosphate) was prepared using tetra-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)pyrimidine-1,3(2H,4H)-diyl)bis(methylene)) bis(phosphate) in place of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate.

LC-MS m/z: 688.1 (M+1). 1H NMR (400 MHz, DMSO-d6) δ 8.77 (s, 1H), 8.23 (d, J=2.4 Hz, 1H), 8.17 (s, 1H), 7.79 (s, 1H), 7.76 (d, J=8.3 Hz, 1H), 7.63 (s, 1H), 7.21 (dd, J=8.4, 1.3 Hz, 1H), 6.73 (d, J=2.4 Hz, 1H), 5.73 (d, J=6.3 Hz, 2H), 5.69 (d, J=11.1 Hz, 2H), 5.42 (q, J=9.1 Hz, 2H), 3.21 (td, J=7.4, 4.5 Hz, 3H), 2.83 (td, J=7.8, 4.5 Hz, 1H), 2.00 (t, J=7.6 Hz, 2H). 19F NMR (376 MHz, DMSO-d6) δ −70.06 (t, J=9.1 Hz, 3F). 31P NMR (162 MHz, DMSO-d6) δ −2.15 (t, J=11.1 Hz), −3.45 (t, J=6.5 Hz).

II. Definitions

"Alkyl" is a linear or branched saturated monovalent hydrocarbon. For example, an alkyl group can have 1 to 18 carbon atoms (i.e., $C_{1-18}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$. Other alkyl groups include heptyl, octyl, nonyl, decyl, undecyl, dodecyl, pentadecyl, hexadecyl, heptadecyl and octadecyl.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as C$_2$, C$_{2-3}$, C$_{2-4}$, C$_{2-5}$, C$_{2-6}$, C$_{2-7}$, C$_{2-8}$, C$_{2-9}$, C$_{2-10}$, C$_3$, C$_{3-4}$, C$_{3-5}$, C$_{3-6}$, C$_4$, C$_{4-5}$, C$_{4-6}$, C$_5$, C$_{5-6}$ and C$_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as C$_2$, C$_{2-3}$, C$_{2-4}$, C$_{2-5}$, C$_{2-6}$, C$_{2-7}$, C$_{2-8}$, C$_{2-9}$, C$_{2-10}$, C$_3$, C$_{3-4}$, C$_{3-5}$, C$_{3-6}$, C$_4$, C$_{4-5}$, C$_{4-6}$, C$_5$, C$_{5-6}$, and C$_6$. Examples of alkynyl groups include, but are not limited to, acetylenyl, propynyl, 1-butynyl, 2-butynyl, butadiynyl, 1-pentynyl, 2-pentynyl, isopentenyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatrienyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as C$_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers an alkoxy group linked to an alkyl group which is linked to the remainder of the compound such that the alkyl group is divalent. Alkoxyalkyl can have any suitable number of carbon, such as from 2 to 6 (C$_{2-6}$ alkoxyalkyl), 2 to 5 (C$_{2-5}$ alkoxyalkyl), 2 to 4 (C$_{2-4}$ alkoxyalkyl), or 2 to 3 (C$_{2-3}$ alkoxyalkyl). Alkoxy and alkyl are as defined above where the alkyl is divalent, and can include, but is not limited to, methoxymethyl (CH$_3$OCH$_2$—), methoxyethyl (CH$_3$OCH$_2$CH$_2$—) and others.

"Alkoxy-alkoxy" refers an alkoxy group linked to a second alkoxy group which is linked to the remainder of the compound. Alkoxy is as defined above, and can include, but is not limited to, methoxy-methoxy (CH$_3$OCH$_2$O—), methoxy-ethoxy (CH$_3$OCH$_2$CH$_2$O—) and others.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, C$_{1-4}$ haloalkyl is a C$_{1-4}$ alkyl wherein one or more of the hydrogen atoms of the C$_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Haloalkoxy" refers to an alkoxy group where some or all of the hydrogen atoms are substituted with halogen atoms. As for an alkyl group, haloalkoxy groups can have any suitable number of carbon atoms, such as C$_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a single saturated or partially unsaturated all carbon ring having 3 to 20 annular carbon atoms (i.e., C$_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having 6 to 12 annular carbon atoms such as bicyclo[3.1.0]hexane and bicyclo[2.1.1]hexane), and polycyclic carbocycles (e.g., tricyclic and tetracyclic carbocycles with up to 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as C$_{1-6}$, C$_{1-2}$, C$_{1-3}$, C$_{1-4}$, C$_{1-5}$, C$_{2-3}$, C$_{2-4}$, C$_{2-5}$, C$_{2-6}$, C$_{3-4}$, C$_{3-5}$, C$_{3-6}$, C$_{4-5}$, C$_{4-6}$ and C$_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocyclyl" or "heterocycle" or "heterocycloalkyl" as used herein refers to a single saturated or partially unsaturated non-aromatic ring or a multiple ring system having at least one heteroatom in the ring (i.e., at least one annular heteroatom selected from oxygen, nitrogen, and sulfur) wherein the multiple ring system includes at least non-aromatic ring containing at least one heteroatom. The multiple ring system can also include other aromatic rings and non-aromatic rings. Unless otherwise specified, a heterocyclyl group has from 3 to 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from 1 to 6 annular carbon atoms and from 1 to 3 annular heteroatoms selected from the group consisting of oxygen, nitrogen and sulfur in the ring. The heteroatoms can optionally be oxidized to form —N(—OH)—, =N(—O—)—, —S(=O)— or —S(=O)$_2$—. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, pyrazolidin-3-one, piperazin-2-one, oxazolidin-2-one, and the like.

Heterocycloalkyl rings also include 9 to 15 membered fused ring heterocycloalkyls having 2, 3, or more rings wherein at least one ring is an aryl ring and at least one ring is a non-aromatic ring containing at least one heteroatom. Representative fused bicyclic heterocycloalkyls include, but are not limited to, indoline (dihydroindole), isoindoline (dihydroisoindole), indazoline (dihydroindazole), benzo[d]imidazole, dihydroquinoline, dihydroisoquinoline, dihydrobenzofuran, dihydroisobenzofuran, benzo[d][1,3]dioxol, dihydrobenzo[b]dioxine, dihydrobenzo[d]oxazole, dihydrobenzo[b]thiophene, dihydroisobenzo[c]thiophene, dihydrobenzo[d]thiazole, dihydrobenzo[c]isothiazole, spiro[cyclobutane-1,3'-indolin]-2'-one, spiro[cyclopropane-1,3'-indolin]-2'-one, 2,3-dihydro-1H-benzo[d]pyrrolo[1,2-a]imidazole, benzo[d][1,3]dioxole, and benzo[b][1,4]thiazine, as shown in the structures below:

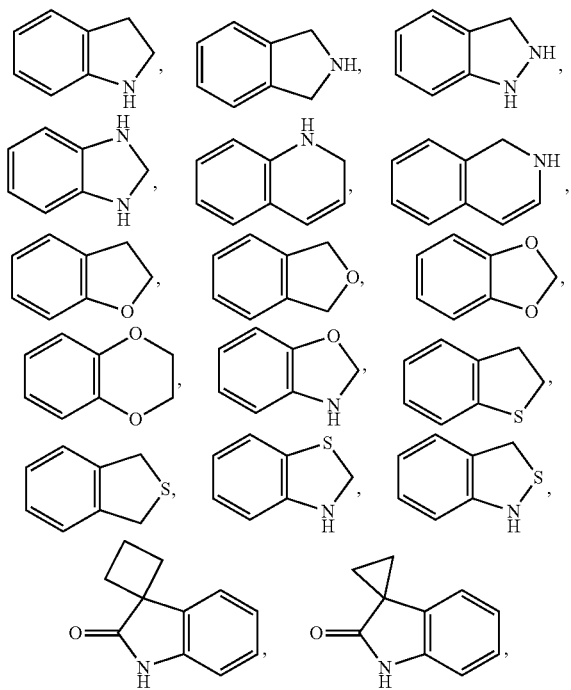

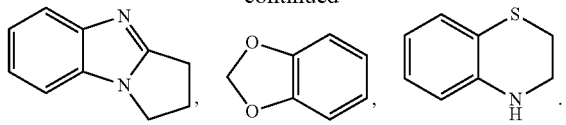

Fused bicyclic heterocycloalkyls can also be represented by the following structures:

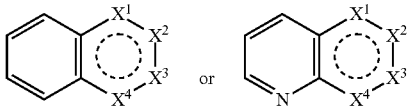

wherein $X^1$, $X^2$, $X^3$ and $X^4$ are each independently absent, —CH$_2$—, —NH—, —O— or —S—, at least one of $X^1$, $X^2$, $X^3$ and $X^4$ is —NH—, —O— or —S—, and the dashed circle represents a saturated or partially unsaturated non-aromatic ring. The fused bicyclic heterocycloalkyls are optionally substituted.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heterocycloalkyl component is as defined above. Alkyl-heterocycloalkyl groups can be substituted or unsubstituted.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from 1 to 6 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1-20 carbon atoms and 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thionaphthenyl, pyrrolo[2,3-b]pyridinyl, quinazolinyl-4(3H)-one, pyridin-2(1H)-one, isoquinolin-1(2H)-one, and triazolyl.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount can vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In certain embodiments, the subject is a human.

"Disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

"Cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma.

Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

"Leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

"Sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

"Melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

"Carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basal oid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

"Metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—$SO_2CH_2$—" is equivalent to "—$CH_2SO_2$—" and both may be connected in either direction. Similarly, an "arylalkyl" group, for example, may be attached to the remainder of the molecule at either an aryl or an alkyl portion of the group. A prefix such as "$C_{u-v}$" or ($C_u$-$C_v$) indicates that the following group has from u to v carbon atoms. For example, "$C_{1-6}$alkyl" and "$C_1$-$C_6$ alkyl" both indicate that the alkyl group has from 1 to 6 carbon atoms.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

III. Compounds

Pharmaceutical Formulations

In some embodiments, the present disclosure provides a pharmaceutical formulation comprising a pharmaceutically effective amount of a compound of the present disclosure, or a pharmaceutically acceptable salt thereof, and a pharmaceutically acceptable carrier or excipient. Also provided herein is a pharmaceutical formulation comprising a pharmaceutically effective amount of a compound of Formula (I), or a pharmaceutically acceptable salt thereof, and a pharmaceutically acceptable carrier or excipient.

In some embodiments, the pharmaceutical composition is for use in treating a cancer.

In some embodiments, the pharmaceutical composition further comprises one or more additional therapeutic agents. Any suitable additional therapeutic agent or combination therapy can be used with the compounds of Formula (I), or a pharmaceutically acceptable salt thereof, such as the agents and therapies described within.

In some embodiments, the pharmaceutical composition comprises a compound of Formula (I), and an additional therapeutic agent, wherein the additional therapeutic agent is an anticancer agent. In some embodiments, the pharmaceutical composition is the pharmaceutical composition wherein the additional therapeutic agent is independently an anti-neoplastic agent, chemotherapy, radiation therapy, or resection therapy. In some embodiments, the pharmaceutical composition is the pharmaceutical composition wherein the additional therapeutic agent is independently rituxan, doxorubicin, gemcitabine, nivolumab, pembrolizumab, nivolumab, pembrolizumab, atezolizumab, or ipilimumab. In some embodiments, the pharmaceutical composition is the pharmaceutical composition wherein the additional therapeutic agent is a PD-1/PD-L1 inhibitor.

In some embodiments, the pharmaceutical composition is the pharmaceutical composition wherein the additional therapeutic agent comprises one or more populations of immune cells, such as natural killer (NK) cells, NK-T cells, T cells, cytokine-induced killer (CIK) cells, macrophage (MAC) cells, tumor infiltrating lymphocytes (TILs) and dendritic cell (DCs).

In some embodiments, the pharmaceutical composition is the pharmaceutical composition wherein the additional therapeutic agent comprises one or more chimeric antigen receptors (CARs).

In some embodiments, the pharmaceutical composition is the pharmaceutical composition wherein the additional therapeutic agent comprises an immunotherapy, an immunostimulatory therapy, a cytokine therapy, a chemokine therapy, a cellular therapy, a gene therapy, or combinations thereof. In some embodiments, the immunotherapy includes co-administering one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins directed against one or more targets or tumor associated antigens (TAAs).

In some embodiments, compounds disclosed herein are formulated with conventional carriers and excipients, which can be selected in accord with ordinary practice. Tablets can contain excipients, glidants, fillers, binders and the like. Aqueous formulations can be prepared in sterile form, and can be isotonic, for instance when intended for delivery by other than oral administration. In some embodiments, formulations can optionally contain excipients such as those set forth in the "Handbook of Pharmaceutical Excipients" (1986). Excipients can include, for example, ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, for example from about 7 to about 10.

In some embodiments, the compounds disclosed herein are administered alone. In some embodiments, compounds disclosed herein are administered in pharmaceutical formulations. In some embodiments a formulation, for veterinary and/or for human use, comprises at least one compound of Formula (I), or a pharmaceutically acceptable salt thereof, together with one or more acceptable carriers and optionally other therapeutic ingredients, such as those additional therapeutic ingredients discussed herein. In some embodiments, carrier(s) are "acceptable" in the sense of being compatible with the other ingredients of the formulation and physiologically innocuous to the recipient thereof.

In some embodiments, formulations of the disclosure include those suitable for the foregoing administration routes. In some embodiments, formulations are presented in unit dosage form. Formulations may be prepared by methods known in the art of pharmacy. Techniques and formulations can be found, for example, in Remington's Pharmaceutical Sciences (Mack Publishing Co., Easton, Pa.). Such methods include, for instance, a step of bringing into association the active ingredient with a carrier comprising one or more accessory ingredients. In some embodiments, formulations are prepared by bringing into association the active ingredient with liquid carriers or finely divided solid carriers or both, and then, in some embodiments, shaping the product.

Formulations suitable for oral administration may be presented as discrete units such as capsules, cachets or tablets each containing a predetermined amount of active ingredient, such as a compound of Formula (I), or a pharmaceutically acceptable salt thereof; as a powder or granules; as a solution or a suspension in an aqueous or non-aqueous liquid; or as an oil-in-water liquid emulsion or a water-in-oil liquid emulsion. In some embodiments, an active ingredient is administered as a bolus, electuary or paste.

A tablet can be made, for example, by compression or molding, optionally with one or more accessory ingredients. Compressed tablets may be prepared, for example, by compressing in a suitable machine the active ingredient in a free-flowing form such as a powder or granules, optionally mixed with a binder, lubricant, inert diluent, preservative, surface active or dispersing agent. Molded tablets may be made, for instance, by molding in a suitable machine a mixture of the powdered active ingredient moistened with an inert liquid diluent. The tablets may optionally be coated or scored. In some embodiments, tablets are formulated so as to provide slow or controlled release of the active ingredient therefrom.

For infections of the eye or other external tissues e.g. mouth and skin, the formulations can be applied as a topical ointment or cream containing a compound of Formula (I), in an amount of, for example, about 0.075 to about 20% w/w (including active ingredient(s) in a range between about 0.1% and about 20% in increments of about 0.1% w/w such as about 0.6% w/w, about 0.7% w/w, etc.), such as about 0.2 to about 15% w/w and such as about 0.5 to about 10% w/w. When formulated in an ointment, a compound of Formula (I), or a pharmaceutically acceptable salt thereof, may be employed with either a paraffinic or a water-miscible ointment base. Alternatively, a compound of Formula (I), or a pharmaceutically acceptable salt thereof, may be formulated in a cream with an oil-in-water cream base.

If desired, the aqueous phase of the cream base may include, for example, at least about 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may in some embodiments include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it can comprise, for example, a mixture of at least one emulsifier with a fat or an oil or with both a fat and an oil. In some embodiments, a hydrophilic emulsifier is included together with a lipophilic emulsifier which acts as a stabilizer. In some embodiments, an emulsion includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include, for instance, Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired properties. The cream can be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

In some embodiments, pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparation, such as a sterile injectable aqueous or oleaginous suspension. Such suspensions may be formulated according to the known art using those suitable dispersing or wetting agents and suspending agents which have been mentioned above. Sterile injectable or intravenous preparations may also include a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed, including synthetic mono- or diglycerides. In addition, fatty acids such as oleic acid may likewise be used in the preparation of injectables.

The amount of active ingredient that may be combined with the carrier material to produce a single dosage form can vary depending upon the host treated and the particular mode of administration. For example, a time-release formulation intended for oral administration to humans may contain about 1 to about 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to about 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient can be present in such formulations in a concentration of about 0.5 to about 20%, such as about 0.5 to about 10%, for example about 1.5% w/w.

Formulations suitable for topical administration in the mouth include, for example, lozenges comprising the active ingredient in a flavored basis, such as sucrose and acacia or tragacanth; pastilles comprising the active ingredient in an inert basis, such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for intrapulmonary or nasal administration have a particle size, for example, in the range of about 0.1 to about 500 microns, such as about 0.5, about 1, about 30, or about 35, etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment of cancer as described below.

Another embodiment provides an inhalable composition comprising a compound of Formula (I), or a pharmaceutically acceptable salt thereof. In some embodiments, the inhalable composition is suitable for treating cancer. In some embodiments, pharmaceutically acceptable salts are inorganic acid salts including hydrochloride, hydrobromide, sulfate or phosphate salts. For example, such salts may cause less pulmonary irritation relative to other salts. In some embodiments, an inhalable composition is delivered to the endobronchial space in an aerosol comprising particles with a mass median aerodynamic diameter (MMAD) between about 1 and about 5 µm. In some embodiments, the compound of Formula (I), or a pharmaceutically acceptable salt thereof, is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In another embodiment, a formulation for nebulization is delivered to the endobronchial space in an aerosol comprising particles with a MMAD predominantly between about 1 µm and about 5 µm using a nebulizer able to aerosolize the formulation of the compound of Formula (I), or a pharmaceutically acceptable salt thereof, into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than about 5 µm, the particles are deposited in the upper airways decreasing the amount of drug delivered to the site of inflammation and bronchoconstriction in the lower respiratory tract. If the MMAD of the aerosol is smaller than about 1 µm, then the particles can in some cases remain suspended in the inhaled air and may be subsequently exhaled during expiration.

When formulated and delivered according to methods herein, the aerosol formulation for nebulization delivers a therapeutically efficacious dose of the compound of Formula (I), or a pharmaceutically acceptable salt thereof, to a therapeutic target, such as the site of a cancer. The amount of drug administered can be adjusted to reflect the efficiency of the delivery of a therapeutically efficacious dose of the compound of Formula (I), or a pharmaceutically acceptable salt thereof. In an embodiment, a combination of the aqueous aerosol formulation with the atomizing, jet, pressurized, vibrating porous plate, or ultrasonic nebulizer permits, depending on the nebulizer, from about 20 to about 90%, such as about 70% delivery of the administered dose of the compound of Formula (I), or a pharmaceutically acceptable salt thereof, into the airways. In an embodiment, from about 30 to about 50% of the active compound is delivered. For example, from about 70 to about 90% of the active compound can be delivered.

In another embodiment, a compound of Formula (I), or a pharmaceutically acceptable salt thereof, is delivered as a dry inhalable powder. The compounds are administered endobronchially as a dry powder formulation to efficaciously deliver fine particles of compound into the endobronchial space using dry powder or metered dose inhalers. For delivery by DPI, the compound of Formula (I), or a pharmaceutically acceptable salt thereof, is processed into particles with, predominantly, MMAD between about 1 μm and about 5 μm by milling spray drying, critical fluid processing, or precipitation from solution. Media milling, jet milling and spray-drying devices and procedures capable of producing the particle sizes with a MMAD between about 1 μm and about 5 μm are well known in the art. In one embodiment, excipients are added to the compound of Formula (I), or a pharmaceutically acceptable salt thereof, before processing into particles of the required sizes. In another embodiment, excipients are blended with the particles of the required size to aid in dispersion of the drug particles, for example by using lactose as an excipient.

Particle size determinations are made using devices well known in the art. For example, a multi-stage Anderson cascade impactor or other suitable method such as those specifically cited within the US Pharmacopoeia Chapter 601 as characterizing devices for aerosols within metered-dose and dry powder inhalers.

In another embodiment, a compound of Formula (I), or a pharmaceutically acceptable salt thereof, can be delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from about 1 μm to about 5 μm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In some embodiments, a compound of Formula (I), or a pharmaceutically acceptable salt thereof, is delivered as a dry powder using either type of dry powder inhaler as described herein, wherein the MMAD of the dry powder, exclusive of any excipients, is predominantly in the range of about 1 μm to about 5 μm.

In another embodiment, a compound of Formula (I), or a pharmaceutically acceptable salt thereof, is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In some embodiments, a compound of Formula (I), or a pharmaceutically acceptable salt thereof, is delivered as a dry powder using a metered dose inhaler wherein the MMAD of the dry powder, exclusive of any excipients, is predominantly in the range of about 1 to about 5 μm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Unit dosage formulations include those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient is controlled and regulated to allow less frequency dosing or to improve the pharmacokinetic or toxicity profile of a given active ingredient.

Effective dose of active ingredient depends at least on the nature of the condition being treated, toxicity, the method of delivery, and the pharmaceutical formulation, and can be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of about 70 kg body weight can range from about 1 mg to about 1000 mg, such as between about 5 mg and about 500 mg, and may take the form of single or multiple doses.

Some embodiments provide a method for manufacturing a medicament for treating cancer in a subject in need thereof. In some embodiments, the method for manufacturing a medicament for treating cancer includes using a compound having the structure of Formula (I), or a pharmaceutically acceptable salt thereof. Some embodiments provide a method for manufacturing a medicament for inhibiting cancer metastasis in a subject in need thereof. In some embodiments, the method for manufacturing a medicament for inhibiting cancer metastasis includes using a compound having the structure of Formula (I), or a pharmaceutically acceptable salt thereof.

In some embodiments, the disclosure provides a use of compound having the structure of Formula (I), or a pharmaceutically acceptable salt thereof, in the treatment of cancer in a subject in need thereof. In some embodiments, the disclosure provides a use of compound having the structure of Formula (I), or a pharmaceutically acceptable salt thereof, in inhibiting cancer metastasis in a subject in need thereof. In some embodiments, the disclosure provides a compound having the structure of Formula (I), or a pharmaceutically acceptable salt thereof, for use in therapy.

IV. Routes of Administration

One or more of the compounds of Formula (I), or a pharmaceutically acceptable salt thereof, (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the route may vary with for example the condition of the recipient. In some embodiments, compounds disclosed herein are orally bioavailable and can be dosed orally.

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the route may vary with for example the condition of the recipient. An advantage of certain compounds disclosed herein is that they are orally bioavailable and can be dosed orally.

A compound of the present disclosure, may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from about 1 mg to about 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, about 125, about 150, about 175, about 200, about 225, about 250, about 275, about 300, about 325, about 350, about 375, about 400, about 425, about 450, about 475, or about 500 mg per dose. Other therapeutically effective amounts of the compound of the present disclosure are about 100 mg per dose, or about 125, about 150, about 175, about 200, about 225, about 250, about 275, about 300, about 325, about 350, about 375, about 400, about 425, about 450, or about 500 mg per dose. A single dose can be administered hourly, daily, or weekly. For example, a single dose can be administered once about every 1 hour, about 2, about 3, about 4, about 6, about 8, about 12, about 16 or once about every 24 hours. A single dose can also be administered once about every 1 day, about 2, about 3, about 4, about 5, about 6, or once about every 7 days. A single dose can also be administered once about every 1 week, about 2, about 3, or once about every 4 weeks. In some embodiments, a single dose can be administered once about every week. A single dose can also be administered once about every month.

Other therapeutically effective amounts of the compound of the present disclosure are about 20, about 25, about 30, about 35, about 40, about 45, about 50, about 55, about 60, about 65, about 70, about 75, about 80, about 85, about 90, about 95, or about 100 mg per dose.

The frequency of dosage of the compound of the present disclosure can be determined by the needs of the individual patient and can be, for example, once per day or twice, or more times, per day. Administration of the compound continues for as long as necessary to treat the disease or condition. For example, a compound can be administered to a human having cancer for a period of from about 20 days to about 180 days or, for example, for a period of from about 20 days to about 90 days or, for example, for a period of from about 30 days to about 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from about 1 to about 14 days, followed by a period of about 7 to about 21 days during which the patient does not receive a dose of the compound, followed by a subsequent period (e.g., from about 1 to about 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

In order to prolong the effect of a compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

V. Combination Therapy

The compounds of Formula I, pharmaceutically acceptable salts thereof, and/or compositions provided herein can also used in combination with other active therapeutic agents for the treatment of cancer.

In some embodiments, a compound, or pharmaceutical composition provided herein, is administered with one or more (e.g., one, two, three, or four) additional therapeutic agents. In some embodiments the additional therapeutic agent includes, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (e.g., a mono- and multi-specific antibody, or fragment thereof, in any format, such as DART®, Duobody®, BiTE®, BiKE, TriKE, XmAb®, TandAb®, scFv, Fab, Fab derivative), a bi-specific antibody, a non-immunoglobulin antibody mimetic (e.g., including adnectin, affibody, affilin, affimer, affitin, alphabody, anticalin, peptide aptamer, armadillo repeat protein (ARM), atrimer, avimer, designed ankyrin repeat protein (DARPin®), fynomer, knottin, Kunitz domain peptide, monobody, and nanoCLAMPs), an antibody-drug conjugate (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, e.g., an inhibitor, agonist, antagonist, ligand, modulator, stimulator, blocker, activator or suppressor of a target (e.g., polypeptide or polynucleotide), such as: 2'-5'-oligoadenylate synthetase (OAS1; NCBI Gene ID: 4938); 5'-3' exoribonuclease 1 (XRN1; NCBI Gene ID: 54464); 5'-nucleotidase ecto (NT5E, CD73; NCBI Gene ID: 4907); ABL proto-oncogene 1, non-receptor tyrosine kinase (ABL1, BCR-ABL, c-ABL, v-ABL; NCBI Gene ID: 25); absent in melanoma 2 (AIM2; NCBI Gene ID: 9447); acetyl-CoA acyltransferase 2 (ACAA2; NCBI Gene ID: 10499); acid phosphatase 3 (ACP3; NCBI Gene ID: 55); adenosine deaminase (ADA, ADA1; NCBI Gene ID: 100); adenosine receptors (e.g., ADORA1 (A1), ADORA2A (A2a, A2AR), ADORA2B (A2b, A2BR), ADORA3 (A3); NCBI Gene IDs: 134, 135, 136, 137); AKT serine/threonine kinase 1 (AKT1, AKT, PKB; NCBI Gene ID: 207); alanyl aminopeptidase, membrane (ANPEP, CD13; NCBI Gene ID: 290); ALK receptor tyrosine kinase (ALK, CD242; NCBI Gene ID: 238); alpha fetoprotein (AFP; NCBI Gene ID: 174); amine oxidase copper containing (e.g., AOC1 (DAO1), AOC2, AOC3 (VAP1); NCBI Gene IDs: 26, 314, 8639); androgen receptor (AR; NCBI Gene ID: 367); angiopoietins (ANGPT1, ANGPT2; NCBI Gene IDs: 284, 285); angiotensin II receptor type 1 (AGTR1; NCBI Gene ID: 185); angiotensinogen (AGT; NCBI Gene ID: 183); apolipoprotein A1 (APOA1; NCBI Gene ID: 335); apoptosis inducing factor mitochondria associated 1 (AIFM1, AIF; NCBI Gene ID: 9131); arachidonate 5-lipoxygenase (ALOX5; NCBI Gene ID: 240); asparaginase (ASPG; NCBI Gene ID: 374569); asteroid homolog 1 (ASTE1; NCBI Gene ID: 28990); ATM serine/threonine kinase (ATM; NCBI Gene ID: 472); ATP binding cassette subfamily B member 1 (ABCB1, CD243, GP170; NCBI Gene ID: 5243); ATP-dependent Clp-protease (CLPP; NCBI Gene ID: 8192); ATR serine/threonine kinase (ATR; NCBI Gene ID: 545); AXL receptor tyrosine kinase (AXL; NCBI Gene ID: 558); B and T lymphocyte associated (BTLA, CD272; NCBI Gene ID: 151888); baculoviral IAP repeat containing proteins (BIRC2 (cIAP1), BIRC3 (cIAP2), XIAP (BIRC4, IAP3), BIRC5 (survivin); NCBI Gene IDs: 329, 330, 331, 332); basigin (Ok blood group) (BSG, CD147; NCBI Gene ID: 682); B-cell lymphoma 2 (BCL2; NCBI Gene ID: 596); BCL2 binding component 3 (BBC3, PUMA; NCBI Gene ID: 27113); BCL2 like (e.g., BCL2L1 (Bcl-x), BCL2L2 (BIM); Bcl-x; NCBI Gene IDs: 598, 10018); beta 3-adrenergic receptor (ADRB3; NCBI Gene ID: 155); bone gamma-carboxyglutamate protein (BGLAP; NCBI Gene ID: 632); bone morphogenetic protein-10 ligand (BMP10; NCBI Gene ID: 27302); bradykinin receptors (e.g., BDKRB1, BDKRB2; NCBI Gene IDs: 623, 624); B-RAF (BRAF; NCBI Gene ID: 273); breakpoint cluster region (BCR; NCBI Gene ID: 613); bromodomain and external domain (BET) bromodomain containing proteins (e.g., BRD2, BRD3, BRD4, BRDT; NCBI Gene IDs: 6046, 8019, 23476, 676); Bruton's tyrosine kinase (BTK; NCBI Gene ID: 695); cadherins (e.g., CDH3 (p-cadherin), CDH6 (k-cadherin); NCBI Gene IDs: 1001, 1004); cancer/testis antigens (e.g., CTAG1A, CTAG1B, CTAG2; NCBI Gene IDs: 1485, 30848, 246100); cannabinoid receptors (e.g., CNR1 (CB1), CNR2 (CB2); NCBI Gene IDs: 1268, 1269); carbohydrate sulfotransferase 15 (CHST15; NCBI Gene ID: 51363); carbonic anhydrases (e.g., CA1, CA2, CA3, CA4, CA5A, CA5B, CA6, CA7, CA8, CA9, CA10, CA11, CA12, CA13, CA14; NCBI Gene IDs: 759, 760, 761, 762, 763, 765, 766, 767, 768, 770, 771, 11238, 23632, 56934, 377677); carcinoembryonic antigen related cell adhesion molecules (e.g., CEACAM3 (CD66d), CEACAM5 (CD66e), CEACAM6 (CD66c); NCBI Gene IDs: 1048, 1084, 4680); casein kinases (e.g., CSNK1A1 (CK1), CSNK2A1 (CK2); NCBI Gene IDs: 1452, 1457); caspases (e.g., CASP3, CASP7, CASP8; NCBI Gene IDs: 836, 840, 841, 864); catenin beta 1 (CTNNB1; NCBI Gene ID: 1499); cathepsin G (CTSG; NCBI Gene ID: 1511); Cbl proto-oncogene B (CBLB, Cbl-b; NCBI Gene ID: 868); C-C motif chemokine ligand 21 (CCL21; NCBI Gene ID: 6366); C-C motif chemokine receptor 2 (CCR2; NCBI Gene ID: 729230); C-C motif chemokine receptors (e.g., CCR3 (CD193), CCR4 (CD194), CCR5 (CD195), CCR8 (CDw198); NCBI Gene IDs: 1232, 1233, 1234, 1237); CCAAT enhancer binding protein alpha (CEBPA, CEBP; NCBI Gene ID: 1050); cell adhesion molecule 1 (CADM1; NCBI Gene ID: 23705); cell division cycle 7 (CDC7; NCBI Gene ID: 8317); cellular communication network factor 2 (CCN2; NCBI Gene ID: 1490); cereblon (CRBN; NCBI Gene ID: 51185); checkpoint kinases (e.g., CHEK1 (CHK1), CHEK2 (CHK2); NCBI Gene IDs: 1111, 11200); cholecystokinin B receptor (CCKBR; NCBI Gene ID: 887); chorionic somatomammotropin hormone 1 (CSH1; NCBI Gene ID: 1442); claudins (e.g., CLDN6, CLDN18; NCBI Gene IDs: 9074, 51208); cluster of differentiation markers (e.g., CD1A, CD1C, CD1D, CD1E, CD2, CD3 alpha (TRA), CD beta (TRB), CD gamma (TRG), CD delta (TRD), CD4, CD8A, CD8B, CD19, CD20 (MS4A1), CD22, CD24, CD25 (IL2RA, TCGFR), CD28, CD33 (SIGLEC3), CD37, CD38, CD39 (ENTPD1), CD40 (TNFRSF5), CD44 (MIC4, PGP1), CD47 (IAP), CD48 (BLAST1), CD52, CD55 (DAF), CD58 (LFA3), CD74, CD79a, CD79b, CD80 (B7-1), CD84, CD86 (B7-2), CD96 (TACTILE), CD99 (MIC2), CD115 (CSF1R), CD116 (GMCSFR, CSF2RA), CD122 (IL2RB), CD123 (IL3RA), CD128 (IL8R1), CD132 (IL2RG), CD135 (FLT3), CD137 (TNFRSF9, 4-1BB), CD142 (TF, TFA), CD152 (CTLA4), CD160, CD182 (IL8R2), CD193 (CCR3), CD194 (CCR4), CD195 (CCR5), CD207, CD221 (IGF1R), CD222 (IGF2R), CD223 (LAG3), CD226 (DNAM1), CD244, CD247, CD248, CD276 (B7-H3), CD331 (FGFR1), CD332 (FGFR2), CD333 (FGFR3), CD334 (FGFR4); NCBI Gene IDs: 909, 911, 912, 913, 914, 919, 920, 923, 925, 926, 930, 931, 933, 940, 941, 942, 945, 951, 952, 953, 958,960, 961, 962, 965, 972, 973, 974, 1043, 1232, 1233, 1234, 1237, 1436, 1438, 1493, 1604, 2152, 2260, 2261, 2263, 2322, 3480, 3482, 3559, 3560, 3561, 3563, 3577, 3579, 3604, 3902, 4267, 6955, 6957, 6964, 6965, 8832, 10666, 11126, 50489, 51744, 80381, 100133941); clusterin (CLU; NCBI Gene ID: 1191); coagulation factors (e.g., F7, FXA; NCBI Gene IDs: 2155, 2159); collagen type IV alpha chains (e.g., COL4A1, COL4A2, COL4A3, COL4A4, COL4A5; NCBI Gene IDs: 1282, 1284, 1285, 1286, 1287); collectin subfamily member 10 (COLEC10; NCBI Gene ID: 10584); colony stimulating factors (e.g., CSF1 (MCSF), CSF2 (GMCSF), CSF3 (GCSF); NCBI Gene IDs: 1435, 1437, 1440); complement factors (e.g., C3, C5; NCBI Gene IDs: 718, 727); COP9 signalosome subunit 5 (COPS5; NCBI Gene ID: 10987); C-type lectin domain family member (e.g., CLEC4C (CD303), CLEC9A (CD370), CLEC12A (CD371); CD371; NCBI Gene ID: 160364, 170482, 283420); C-X-C motif chemokine ligand 12 (CXCL12; NCBI Gene ID: 6387); C-X-C motif chemokine receptors (CXCR1 (IL8R1, CD128), CXCR2 (IL8R2, CD182), CXCR3 (CD182, CD183, IP-10R), CXCR4 (CD184); NCBI Gene ID: 2833, 3577, 3579, 7852); cyclin D1 (CCND1, BCL1; NCBI Gene ID: 595); cyclin dependent kinases (e.g., CDK1, CDK2, CDK3, CDK4, CDK5, CDK6, CDK7, CDK8, CDK9, CDK10, CDK12; NCBI Gene ID: 983, 1017, 1018, 1019, 1020, 1021, 1022, 1024, 1025, 8558, 51755); cyclin G1 (CCNG1; NCBI Gene ID: 900); cytochrome P450 family members (e.g., CYP2D6, CYP3A4, CYP11A1, CYP11B2, CYP17A1, CYP19A1, CYP51A1; NCBI Gene IDs: 1565, 1576, 1583, 1585, 1586, 1588, 1595); cytochrome P450 oxidoreductase (POR; NCBI Gene ID: 5447); cytokine inducible SH2 containing protein (CISH; NCBI Gene ID: 1154); cytotoxic T-lymphocyte associated protein 4 (CTLA4, CD152; NCBI Gene ID: 1493); DEAD-box helicases (e.g., DDX5, DDX6, DDX58; NCBI Gene IDs: 1655, 1656, 23586); delta like canonical Notch ligands (e.g., DLL3, DLL4; NCBI Gene IDs: 10683, 54567); diablo IAP-binding mitochondrial protein (DIABLO, SMAC; NCBI Gene ID: 56616); diacylglycerol kinases (e.g., DGKA, DGKZ; NCBI Gene IDs: 1606, 8525); dickkopf WNT signaling pathway inhibitors (e.g., DKK1, DKK3; NCBI Gene ID: 22943, 27122); dihydrofolate reductase (DHFR; NCBI Gene ID: 1719); dihydropyrimidine dehydrogenase (DPYD; NCBI Gene ID: 1806); dipeptidyl peptidase 4 (DPP4; NCBI Gene ID: 1803); discoidin domain receptor tyrosine kinases (e.g., DDR1 (CD167), DDR2; CD167; NCBI Gene ID: 780, 4921); DNA dependent protein kinase (PRKDC; NCBI Gene ID: 5591); DNA topoisomerases (e.g., TOP1, TOP2A, TOP2B, TOP3A, TOP3B; NCBI Gene ID: 7150, 7153, 7155, 7156, 8940); dopachrome tautomerase (DCT; NCBI Gene ID: 1638); dopamine receptor D2 (DRD2; NCBI Gene ID: 1318); DOT1 like histone lysine methyltransferase (DOT1L; NCBI Gene ID: 84444); ectonucleotide pyrophosphatase/phosphodiesterase 3 (ENPP3, CD203c; NCBI Gene ID: 5169); EMAP like 4 (EML4; NCBI Gene ID: 27436); endoglin (ENG; NCBI Gene ID: 2022); endoplasmic reticulum aminopeptidases (e.g., ERAP1, ERAP2; NCBI Gene ID: 51752, 64167); enhancer of zeste 2 polycomb repressive complex 2 subunit (EZH2; NCBI Gene ID: 2146); ephrin receptors (e.g., EPHA1, EPHA2EPHA3, EPHA4, EPHA5, EPHA7, EPHB4; NCBIGene ID: 1969, 2041, 2042, 2043, 2044, 2045, 2050); ephrins (e.g., EFNA1, EFNA4, EFNB2; NCBI Gene ID: 1942, 1945, 1948); epidermal growth factor receptors (e.g., ERBB1 (HER1, EGFR), ERBB1 variant III (EGFRvIII), ERBB2 (HER2, NEU, CD340), ERBB3 (HER3), ERBB4 (HER4); NCBI Gene ID: 1956, 2064, 2065, 2066); epithelial cell adhesion molecule (EPCAM; NCBI Gene ID: 4072); epithelial mitogen (EPGN; NCBI Gene ID: 255324); eukaryotic translation elongation factors (e.g., EEF1A2, EEF2; NCBI Gene ID: 1917, 1938); eukaryotic translation initiation factors (e.g., EIF4A1, EIF5A; NCBI Gene ID: 1973, 1984); exportin-1 (XPO1; NCBI Gene ID: 7514); farnesoid X receptor (NR1H4, FXR; NCBI Gene ID: 9971); Fas ligand (FASLG, FASL, CD95L, CD178, TNFSF6;

NCBI Gene ID: 356); fatty acid amide hydrolase (FAAH; NCBI Gene ID: 2166); fatty acid synthase (FASN; FAS; NCBI Gene ID: 2194); Fc fragment of Ig receptors (e.g., FCER1A, FCGRT, FCGR3A (CD16); NCBI Gene IDs: 2205, 2214, 2217); Fc receptor like 5 (FCRL5, CD307; NCBI Gene ID: 83416); fibroblast activation protein alpha (FAP; NCBI Gene ID: 2191); fibroblast growth factor receptors (e.g., FGFR1 (CD331), FGFR2 (CD332), FGFR3 (CD333), FGFR4 (CD334); NCBI Gene IDs: 2260, 2261, 2263, 2264); fibroblast growth factors (e.g., FGF1 (FGF alpha), FGF2 (FGF beta), FGF4, FGF5; NCBI Gene IDs: 2246, 2247, 2249, 2250); fibronectin 1 (FN1, MSF; NCBI Gene ID: 2335); fms related receptor tyrosine kinases (e.g., FLT1 (VEGFR1), FLT3 (STK1, CD135), FLT4 (VEGFR2); NCBI Gene IDs: 2321, 2322, 2324); fms related receptor tyrosine kinase 3 ligand (FLT3LG; NCBI Gene ID: 2323); focal adhesion kinase 2 (PTK2, FAK1; NCBI Gene ID: 5747); folate hydrolase 1 (FOLH1, PSMA; NCBI Gene ID: 2346); folate receptor 1 (FOLR1; NCBI Gene ID: 2348); forkhead box protein M1 (FOXM1; NCBI Gene ID: 2305); FURIN (FURIN, PACE; NCBI Gene ID: 5045); FYN tyrosine kinase (FYN, SYN; NCBI Gene ID: 2534); galectins (e.g., LGALS3, LGALS8 (PCTA1), LGALS9; NCBI Gene ID: 3958, 3964, 3965); glucocorticoid receptor (NR3C1, GR; NCBI Gene ID: 2908); glucuronidase beta (GUSB; NCBI Gene ID: 2990); glutamate metabotropic receptor 1 (GRM1; NCBI Gene ID: 2911); glutaminase (GLS; NCBI Gene ID: 2744); glutathione S-transferase Pi (GSTP1; NCBI Gene ID: 2950); glycogen synthase kinase 3 beta (GSK3B; NCBI Gene ID: 2932); glypican 3 (GPC3; NCBI Gene ID: 2719); gonadotropin releasing hormone 1 (GNRH1; NCBI Gene ID: 2796); gonadotropin releasing hormone receptor (GNRHR; NCBI Gene ID: 2798); GPNMB glycoprotein nmb (GPNMB, osteoactivin; NCBI Gene ID: 10457); growth differentiation factor 2 (GDF2, BMP9; NCBI Gene ID: 2658); growth factor receptor-bound protein 2 (GRB2, ASH; NCBI Gene ID: 2885); guanylate cyclase 2C (GUCY2C, STAR, MECIL, MUCIL, NCBI Gene ID: 2984); H19 imprinted maternally expressed transcript (H19; NCBI Gene ID: 283120); HCK proto-oncogene, Src family tyrosine kinase (HCK; NCBI Gene ID: 3055); heat shock proteins (e.g., HSPA5 (HSP70, BIP, GRP78), HSPB1 (HSP27), HSP90B1 (GP96); NCBI Gene IDs: 3309, 3315, 7184); heme oxygenases (e.g., HMOX1 (HO1), HMOX2 (HO1); NCBI Gene ID: 3162, 3163); heparanase (HPSE; NCBI Gene ID: 10855); hepatitis A virus cellular receptor 2 (HAVCR2, TIM3, CD366; NCBI Gene ID: 84868); hepatocyte growth factor (HGF; NCBI Gene ID: 3082); HERV-H LTR-associating 2 (HHLA2, B7-H7; NCBI Gene ID: 11148); histamine receptor H2 (HRH2; NCBI Gene ID: 3274); histone deacetylases (e.g., HDAC1, HDAC7, HDAC9; NCBI Gene ID: 3065, 9734, 51564); HRas proto-oncogene, GTPase (HRAS; NCBI Gene ID: 3265); hypoxia-inducible factors (e.g., HIF1A, HIF2A (EPAS1); NCBI Gene IDs: 2034, 3091); I-Kappa-B kinase (IKK beta; NCBI Gene IDs: 3551, 3553); IKAROS family zinc fingers (IKZF1 (LYF1), IKZF3; NCBI Gene ID: 10320, 22806); immunoglobulin superfamily member 11 (IGSF11; NCBI Gene ID: 152404); indoleamine 2,3-dioxygenases (e.g., IDO1, IDO2; NCBI Gene IDs: 3620, 169355); inducible T cell costimulator (ICOS, CD278; NCBI Gene ID: 29851); inducible T cell costimulator ligand (ICOSLG, B7-H2; NCBI Gene ID: 23308); insulin like growth factor receptors (e.g., IGF1R, IGF2R; NCBI Gene ID: 3480, 3482); insulin like growth factors (e.g., IGF1, IGF2; NCBI Gene IDs: 3479, 3481); insulin receptor (INSR, CD220; NCBI Gene ID: 3643); integrin subunits (e.g., ITGA5 (CD49e), ITGAV (CD51), ITGB1 (CD29), ITGB2 (CD18, LFA1, MAC1), ITGB7; NCBI Gene IDs: 3678, 3685, 3688, 3695, 3698); intercellular adhesion molecule 1 (ICAM1, CD54; NCBI Gene ID: 3383); interleukin 1 receptor associated kinase 4 (IRAK4; NCBI Gene ID: 51135); interleukin receptors (e.g., IL2RA (TCGFR, CD25), IL2RB (CD122), IL2RG (CD132), IL3RA, IL6R, IL13RA2 (CD213A2), IL22RA1; NCBI Gene IDs: 3598, 3559, 3560, 3561, 3563, 3570, 58985); interleukins (e.g., IL1A, IL1B, IL2, IL3, IL6 (HGF), IL7, IL8 (CXCL8), IL10 (TGIF), IL12A, IL12B, IL15, IL17A (CTLA8), IL18, IL23A, IL24, IL-29 (IFNL1); NCBI Gene IDs: 3552, 3553, 3558, 3562, 3565, 3569, 3574, 3586, 3592, 3593, 3600, 3605, 3606, 11009, 51561, 282618); isocitrate dehydrogenases (NADP(+)1) (e.g., IDH1, IDH2; NCBI Gene IDs: 3417, 3418); Janus kinases (e.g., JAK1, JAK2, JAK3; NCBI Gene IDs: 3716, 3717, 3718); kallikrein related peptidase 3 (KLK3; NCBI Gene ID: 354); killer cell immunoglobulin like receptor, Ig domains and long cytoplasmic tails (e.g., KIR2DL1 (CD158A), KIR2DL2 (CD158B1), KIR2DL3 (CD158B), KIR2DL4 (CD158D), KIR2DL5A (CD158F), KIR2DL5B, KIR3DL1 (CD158E1), KIR3DL2 (CD158K), KIR3DP1 (CD158c), KIR2DS2 (CD158J); NCBI Gene IDs: 3802, 3803, 3804, 3805, 3811, 3812, 57292, 553128, 548594, 100132285); killer cell lectin like receptors (e.g., KLRC1 (CD159A), KLRC2 (CD159c), KLRC3, KLRRC4, KLRD1 (CD94), KLRG1, KLRK1 (NKG2D, CD314); NCBI Gene IDs: 3821, 3822, 3823, 3824, 8302, 10219, 22914); kinase insert domain receptor (KDR, CD309, VEGFR2; NCBI Gene ID: 3791); kinesin family member 11 (KIF11; NCBI Gene ID: 3832); KiSS-1 metastasis suppressor (KISS1; NCBI Gene ID: 3814); KIT proto-oncogene, receptor tyrosine kinase (KIT, C-KIT, CD117; NCBI Gene ID: 3815); KRAS proto-oncogene, GTPase (KRAS; NCBI Gene ID: 3845); lactotransferrin (LTF; NCBI Gene ID: 4057); LCK proto-oncogene, Src family tyrosine kinase (LCK; NCBI Gene ID: 3932); LDL receptor related protein 1 (LRP1, CD91, IGFBP3R; NCBI Gene ID: 4035); leucine rich repeat containing 15 (LRRC15; NCBI Gene ID: 131578); leukocyte immunoglobulin like receptors (e.g., LILRB1 (ILT2, CD85J), LILRB2 (ILT4, CD85D); NCBI Gene ID: 10288, 10859); leukotriene A4 hydrolase (LTA4H; NCBI Gene ID: 4048); linker for activation of T-cells (LAT; NCBI Gene ID: 27040); luteinizing hormone/choriogonadotropin receptor (LHCGR; NCBI Gene ID: 3973); LY6/PLAUR domain containing 3 (LYPD3; NCBI Gene ID: 27076); lymphocyte activating 3 (LAG3; CD223; NCBI Gene ID: 3902); lymphocyte antigens (e.g., LY9 (CD229), LY75 (CD205); NCBI Gene IDs: 4063, 17076); LYN proto-oncogene, Src family tyrosine kinase (LYN; NCBI Gene ID: 4067); lymphocyte cytosolic protein 2 (LCP2; NCBI Gene ID: 3937); lysine demethylase 1A (KDM1A; NCBI Gene ID: 23028); lysophosphatidic acid receptor 1 (LPAR1, EDG2, LPA1, GPR26; NCBI Gene ID: 1902); lysyl oxidase (LOX; NCBI Gene ID: 4015); lysyl oxidase like 2 (LOXL2; NCBI Gene ID: 4017); macrophage migration inhibitory factor (MIF, GIF; NCBI Gene ID: 4282); macrophage stimulating 1 receptor (MST1R, CD136; NCBI Gene ID: 4486); MAGE family members (e.g., MAGEA1, MAGEA2, MAGEA2B, MAGEA3, MAGEA4, MAGEA5, MAGEA6, MAGEA10, MAGEA11, MAGEC1, MAGEC2, MAGED1, MAGED2; NCBI Gene IDs: 4100, 4101, 4102, 4103, 4104, 4105, 4109, 4110, 9500, 9947, 10916, 51438, 266740); major histocompatibility complexes (e.g., HLA-A, HLA-E, HLA-F, HLA-G; NCBI Gene IDs: 3105, 3133, 3134, 3135); major vault protein (MVP, VAULT1; NCBI Gene ID: 9961); MALT1 paracaspase (MALT1; NCBI Gene ID: 10892); MAPK activated protein kinase 2 (MAPKAPK2; NCBI Gene ID: 9261); MAPK interacting serine/threonine kinases (e.g., MKNK1, MKNK2; NCBI Gene IDs: 2872, 8569); matrix metallopeptidases (e.g., MMP1, MMP2, MMP3, MMP7, MMP8, MMP9, MMP10, MMP11, MMP12, MMP13, MMP14, MMP15, MMP16, MMP17, MMP19, MMP20, MMP21, MMP24, MMP25, MMP26, MMP27, MMP28; NCBI Gene IDs: 4312, 4313, 4314, 4316, 4317, 4318, 4319, 4320, 4321, 4322, 4323, 4324, 4325, 4326, 4327, 9313, 10893, 56547, 64066, 64386, 79148, 118856); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; BMFS6; NCBI Gene ID: 4194); mechanistic target of rapamycin kinase (MTOR, FRAP1; NCBI Gene ID: 2475); melan-A (MLANA; NCBI Gene ID: 2315); melanocortin receptors (MC1R, MC2R; NCBI Gene IDs: 4157, 4148); MER proto-oncogene, tyrosine kinase (MERTK; NCBI Gene ID: 10461); mesothelin (MSLN; NCBI Gene ID: 10232); MET proto-oncogene, receptor tyrosine kinase (MET, c-Met, HGFR; NCBI Gene ID: 4233); methionyl aminopeptidase 2 (METAP2, MAP2; NCBI Gene ID: 10988); MHC class I polypeptide-related sequences (e.g., MICA, MICB; NCBI Gene IDs: 4277, 100507436); mitogen activated protein kinases (e.g., MAPK1 (ERK2), MAPK3 (ERK1), MAPK8 (JNK1), MAPK9 (JNK2), MAPK10 (JNK3), MAPK11 (p38 beta), MAPK12; NCBI Gene IDs: 5594, 5595, 5599, 5600, 5601, 5602, 819251); mitogen-activated protein kinase kinase kinases (e.g., MAP3K5 (ASK1), MAP3K8 (TPL2, AURA2); NCBI Gene IDs: 4217, 1326); mitogen-activated protein kinase kinase kinase kinase 1 (MAP4K1, HPK1; NCBI Gene ID: 11184); mitogen-activated protein kinase kinases (e.g., MAP2K1 (MEK1), MAP2K2 (MEK2), MAP2K7 (MEK7); NCBI Gene IDs: 5604, 5605, 5609); MPL proto-oncogene, thrombopoietin receptor (MPL; NCBI Gene ID: 4352); mucins (e.g., MUC1 (including splice variants thereof (e.g., including MUC1/A, C, D, X, Y, Z and REP)), MUC5AC, MUC16 (CA125); NCBI Gene IDs: 4582, 4586, 94025); MYC proto-oncogene, bHLH transcription factor (MYC; NCBI Gene ID: 4609); myostatin (MSTN, GDF8; NCBI Gene ID: 2660); myristoylated alanine rich protein kinase C substrate (MARCKS; NCBI Gene ID: 4082); natriuretic peptide receptor 3 (NPR3; NCBI Gene ID: 4883); natural killer cell cytotoxicity receptor 3 ligand 1 (NCR3LG1, B7-H6; NCBI Gene ID: 374383); necdin, MAGE family member (NDN; NCBI Gene ID: 4692); nectin cell adhesion molecules (e.g., NECTIN2 (CD112, PVRL2), NECTIN4 (PVRL4); NCBI Gene IDs: 5819, 81607); neural cell adhesion molecule 1 (NCAM1, CD56; NCBI Gene ID: 4684); neuropilins (e.g., NRP1 (CD304, VEGF165R), NRP2 (VEGF165R2); NCBI Gene IDs: 8828, 8829); neurotrophic receptor tyrosine kinases (e.g., NTRK1 (TRKA), NTRK2 (TRKB), NTRK3 (TRKC); NCBI Gene IDs: 4914, 4915, 4916); NFKB activating protein (NKAP; NCBI Gene ID: 79576); NIMA related kinase 9 (NEK9; NCBI Gene ID: 91754); NLR family pyrin domain containing 3 (NLRP3, NALP3; NCBI Gene ID: 114548); notch receptors (e.g., NOTCH1, NOTCH2, NOTCH3, NOTCH4; NCBI Gene IDs: 4851, 4853, 4854, 4855); NRAS proto-oncogene, GTPase (NRAS; NCBI Gene ID: 4893); nuclear factor kappa B (NFKB1, NFKB2; NCBI Gene IDs: 4790, 4791); nuclear factor, erythroid 2 like 2 (NFE2L2; NRF2; NCBI Gene ID: 4780); nuclear receptor subfamily 4 group A member 1 (NR4A1; NCBI Gene ID: 3164); nucleolin (NCL; NCBI Gene ID: 4691); nucleophosmin 1 (NPM1; NCBI Gene ID: 4869); nucleotide binding oligomerization domain containing 2 (NOD2; NCBI Gene ID: 64127); nudix hydrolase 1 (NUDT1; NCBI Gene ID: 4521); O-6-methylguanine-DNA methyltransferase (MGMT; NCBI Gene ID: 4255); opioid receptor delta 1 (OPRD1; NCBI Gene ID: 4985); ornithine decarboxylase 1 (ODC1; NCBI Gene ID: 4953); oxoglutarate dehydrogenase (OGDH; NCBI Gene ID: 4967); parathyroid hormone (PTH; NCBI Gene ID: 5741); PD-L1 (CD274; NCBI Gene ID: 29126); periostin (POSTN; NCBI Gene ID: 10631); peroxisome proliferator activated receptors (e.g., PPARA (PPAR alpha), PPARD (PPAR delta), PPARG (PPAR gamma); NCBI Gene IDs: 5465, 5467, 5468); phosphatase and tensin homolog (PTEN; NCBI Gene ID: 5728); phosphatidylinositol-4,5-bisphosphate 3-kinases (PIK3CA (PI3K alpha), PIK3CB (PI3K beta), PIK3CD (PI3K delta), PIK3CG (PI3K gamma); NCBI Gene IDs: 5290, 5291, 5293, 5294); phospholipases (e.g., PLA2G1B, PLA2G2A, PLA2G2D, PLA2G3, PLA2G4A, PLA2G5, PLA2G7, PLA2G10, PLA2G12A, PLA2G12B, PLA2G15; NCBI Gene IDs: 5319, 5320, 5321, 5322, 7941, 8399, 50487, 23659, 26279, 81579, 84647); Pim proto-oncogene, serine/threonine kinases (e.g., PIM1, PIM2, PIM3; NCBI Gene IDs: 5292, 11040, 415116); placenta growth factor (PGF; NCBI Gene ID: 5228); plasminogen activator, urokinase (PLAU, u-PA, ATF; NCBI Gene ID: 5328); platelet derived growth factor receptors (e.g., PDGFRA (CD140A, PDGFR2), FDGFRB (CD140B, PDGFR1); NCBI Gene IDs: 5156, 5159); plexin B1 (PLXNB1; NCBI Gene ID: 5364); poliovirus receptor (PVR) cell adhesion molecule (PVR, CD155; NCBI Gene ID: 5817); polo like kinase 1 (PLK1; NCBI Gene ID: 5347); poly(ADP-ribose) polymerases (e.g., PARP1, PARP2, PARP3; NCBI Gene IDs: 142, 10038, 10039); polycomb protein EED (EED; NCBI Gene ID: 8726); porcupine O-acyltransferase (PORCN; NCBI Gene ID: 64840); PRAME nuclear receptor transcriptional regulator (PRAME; NCBI Gene ID: 23532); premelanosome protein (PMEL; NCBI Gene ID: 6490); progesterone receptor (PGR; NCBI Gene ID: 5241); programmed cell death 1 (PDCD1, PD-1, CD279; NCBI Gene ID: 5133); programmed cell death 1 ligand 2 (PDCD1LG2, CD273, PD-L2; NCBI Gene ID: 80380); prominin 1 (PROM1, CD133; NCBI Gene ID: 8842); promyelocytic leukemia (PML; NCBI Gene ID: 5371); prosaposin (PSAP; NCBI Gene ID: 5660); prostaglandin E receptor 4 (PTGER4; NCBI Gene ID: 5734); prostaglandin E synthase (PTGES; NCBI Gene ID: 9536); prostaglandin-endoperoxide synthases (PTGS1 (COX1), PTGS2 (COX2); NCBI Gene IDs: 5742, 5743); proteasome 20S subunit beta 9 (PSMB9; NCBI Gene ID: 5698); protein arginine methyltransferases (e.g., PRMT1, PRMT5; NCBI Gene ID: 3276, 10419); protein kinase N3 (PKN3; NCBI Gene ID: 29941); protein phosphatase 2A (PPP2CA; NCBI Gene ID: 5515); protein tyrosine kinase 7 (inactive) (PTK7; NCBI Gene ID: 5754); protein tyrosine phosphatase receptors (PTPRB (PTPB), PTPRC (CD45R); NCBI Gene ID: 5787, 5788); prothymosin alpha (PTMA; NCBI Gene ID: 5757); purine nucleoside phosphorylase (PNP; NCBI Gene ID: 4860); purinergic receptor P2X 7 (P2RX7; NCBI Gene ID: 5027); PVR related immunoglobulin domain containing (PVRIG, CD112R; NCBI Gene ID: 79037); Raf-1 proto-oncogene, serine/threonine kinase (RAF1, c-Raf; NCBI Gene ID: 5894); RAR-related orphan receptor gamma (RORC; NCBI Gene ID: 6097); ras homolog family member C (RHOC); NCBI Gene ID: 389); Ras homolog, mTORC1 binding (RHEB; NCBI Gene ID: 6009); RB transcriptional corepressor 1 (RB1; NCBI Gene ID: 5925); receptor-interacting serine/threonine protein kinase 1 (RIPK1; NCBI Gene ID: 8737); ret proto-oncogene (RET; NCBI Gene ID: 5979);

retinoic acid early transcripts (e.g., RAET1E, RAET1G, RAET1L; NCBI Gene IDs: 135250, 154064, 353091); retinoic acid receptors alpha (e.g., RARA, RARG; NCBI Gene IDs: 5914, 5916); retinoid X receptors (e.g., RXRA, RXRB, RXRG; NCBI Gene IDs: 6256, 6257, 6258); Rho associated coiled-coil containing protein kinases (e.g., ROCK1, ROCK2; NCBI Gene IDs: 6093, 9475); ribosomal protein S6 kinase B1 (RPS6KB1, S6K-beta 1; NCBI Gene ID: 6198); ring finger protein 128 (RNF128, GRAIL; NCBI Gene ID: 79589); ROS proto-oncogene 1, receptor tyrosine kinase (ROS1; NCBI Gene ID: 6098); roundabout guidance receptor 4 (ROBO4; NCBI Gene ID: 54538); RUNX family transcription factor 3 (RUNX3; NCBI Gene ID: 864); S100 calcium binding protein A9 (S100A9; NCBI Gene ID: 6280); secreted frizzled related protein 2 (SFRP2; NCBI Gene ID: 6423); secreted phosphoprotein 1 (SPP1; NCBI Gene ID: 6696); secretoglobin family 1A member 1 (SCGB1A1; NCBI Gene ID: 7356); selectins (e.g., SELE, SELL (CD62L), SELP (CD62); NCBI Gene IDs: 6401, 6402, 6403); semaphorin 4D (SEMA4D; CD100; NCBI Gene ID: 10507); sialic acid binding Ig like lectins (SIGLEC7 (CD328), SIGLEC9 (CD329), SIGLEC10; NCBI Gene ID: 27036, 27180, 89790); signal regulatory protein alpha (SIRPA, CD172A; NCBI Gene ID: 140885); signal transducer and activator of transcription (e.g., STAT1, STAT3, STAT5A, STAT5B; NCBI Gene IDs: 6772, 6774, 6776, 6777); sirtuin-3 (SIRT3; NCBI Gene ID: 23410); signaling lymphocytic activation molecule (SLAM) family members (e.g., SLAMF1 (CD150), SLAMF6 (CD352), SLAMF7 (CD319), SLAMF8 (CD353), SLAMF9; NCBI Gene IDs: 56833, 57823, 89886, 114836); SLIT and NTRK like family member 6 (SLITRK6; NCBI Gene ID: 84189); smoothened, frizzled class receptor (SMO; NCBI Gene ID: 6608); soluble epoxide hydrolase 2 (EPHX2; NCBI Gene ID: 2053); solute carrier family members (e.g., SLC3A2 (CD98), SLC5A5, SLC6A2, SLC10A3, SLC34A2, SLC39A6, SLC43A2 (LAT4), SLC44A4; NCBI Gene IDs: 6520, 6528, 6530, 8273, 10568, 25800, 80736, 124935); somatostatin receptors (e.g., SSTR1, SSTR2, SSTR3, SSTR4, SSTR5; NCBI Gene IDs: 6751, 6752, 6753, 6754, 6755); sonic hedgehog signaling molecule (SHH; NCBI Gene ID: 6469); Sp1 transcription factor (SP1; NCBI Gene ID: 6667); sphingosine kinases (e.g., SPHK1, SPHK2; NCBI Gene IDs: 8877, 56848); sphingosine-1-phosphate receptor 1 (S1PR1, CD363; NCBI Gene ID: 1901); spleen associated tyrosine kinase (SYK; NCBI Gene ID: 6850); splicing factor 3B factor 1 (SF3B1; NCBI Gene ID: 23451); SRC proto-oncogene, non-receptor tyrosine kinase (SRC; NCBI Gene ID: 6714); stabilin 1 (STAB1, CLEVER-1; NCBI Gene ID: 23166); STEAP family member 1 (STEAP1; NCBI Gene ID: 26872); steroid sulfatase (STS; NCBI Gene ID: 412); stimulator of interferon response cGAMP interactor 1 (STING1; NCBI Gene ID: 340061); superoxide dismutase 1 (SOD1, ALS1; NCBI Gene ID: 6647); suppressors of cytokine signaling (SOCS1 (CISH1), SOCS3 (CISH3); NCBI Gene ID: 8651, 9021); synapsin 3 (SYN3; NCBI Gene ID: 8224); syndecan 1 (SDC1, CD138, syndecan; NCBI Gene ID: 6382); synuclein alpha (SNCA, PARK1; NCBI Gene ID: 6622); T cell immunoglobulin and mucin domain containing 4 (TIMD4, SMUCKLER; NCBI Gene ID: 91937); T cell immunoreceptor with Ig and ITIM domains (TIGIT; NCBI Gene ID: 201633); tachykinin receptors (e.g., TACR1, TACR3; NCBI Gene ID: 6869, 6870); TANK binding kinase 1 (TBK1; NCBI Gene ID: 29110); tankyrase (TNKS; NCBI Gene ID: 8658); TATA-box binding protein associated factor, RNA polymerase I subunit B (TAF1B; NCBI Gene ID: 9014); T-box transcription factor T (TBXT; NCBI Gene ID: 6862); TCDD inducible poly(ADP-ribose) polymerase (TIPARP, PAPR7; NCBI Gene ID: 25976); tec protein tyrosine kinase (TEC; NCBI Gene ID: 7006); TEK receptor tyrosine kinase (TEK, CD202B, TIE2; NCBI Gene ID: 7010); telomerase reverse transcriptase (TERT; NCBI Gene ID: 7015); tenascin C (TNC; NCBI Gene ID: 3371); three prime repair exonucleases (e.g., TREX1, TREX2; NCBI Gene ID: 11277, 11219); thrombomodulin (THBD, CD141; NCBI Gene ID: 7056); thymidine kinases (e.g., TK1, TK2; NCBI Gene IDs: 7083, 7084); thymidine phosphorylase (TYMP; NCBI Gene ID: 1890); thymidylate synthase (TYMS; NCBI Gene ID: 7298); thyroid hormone receptor (THRA, THRB; NCBI Gene IDs: 7606, 7608); thyroid stimulating hormone receptor (TSHR; NCBI Gene ID: 7253); TNF superfamily members (e.g., TNFSF4 (OX40L, CD252), TNFSF5 (CD40L), TNFSF7 (CD70), TNFSF8 (CD153, CD30L), TNFSF9 (4-1BB-L, CD137L), TNFSF10 (TRAIL, CD253, APO2L), TNFSF11 (CD254, RANKL2, TRANCE), TNFSF13 (APRIL, CD256, TRAIL2), TNFSF13b (BAFF, BLYS, CD257), TNFSF14 (CD258, LIGHT), TNFSF18 (GITRL); NCBI Gene IDs: 944, 959, 970, 7292, 8600, 8740, 8741, 8743, 8744, 8995); toll like receptors (e.g., TLR1 (CD281), TLR2 (CD282), TLR3 (CD283), TLR4 (CD284), TLR5, TLR6 (CD286), TLR7, TLR8 (CD288), TLR9 (CD289), TLR10 (CD290); NCBI Gene IDs: 7096, 7097, 7098, 7099, 10333, 51284, 51311, 54106, 81793); transferrin (TF; NCBI Gene ID: 7018); transferrin receptor (TFRC, CD71; NCBI Gene ID: 7037); transforming growth factors (e.g., TGFA, TGFB1; NCBI Gene ID: 7039, 7040); transforming growth factor receptors (e.g., TGFBR1, TGFBR2, TGFBR3; NCBI Gene ID: 7046, 7048, 7049); transforming protein E7 (E7; NCBI Gene ID: 1489079); transglutaminase 5 (TGM5; NCBI Gene ID: 9333); transient receptor potential cation channel subfamily V member 1 (TRPV1, VR1; NCBI Gene ID: 7442); transmembrane and immunoglobulin domain containing 2 (TMIGD2, CD28H, IGPR1; NCBI Gene ID: 126259); triggering receptors expressed on myeloid cells (e.g., TREM1 (CD354), TREM2; NCBI Gene ID: 54209, 54210); trophinin (TRO, MAGED3; NCBI Gene ID: 7216); trophoblast glycoprotein (TPBG; NCBI Gene ID: 7162); tryptophan 2,3-dioxygenase (TDO2; NCBI Gene ID: 6999); tryptophan hydroxylases (e.g., TPH1, TPH2; NCBI Gene ID: 7166, 121278); tumor associated calcium signal transducer 2 (TACSTD2, TROP2, EGP1; NCBI Gene ID: 4070); tumor necrosis factor (TNF; NCBI Gene ID: 7124); tumor necrosis factor (TNF) receptor superfamily members (e.g., TNFRSF1A (CD120a), TNFRSF1B (CD120b), TNFRSF4 (OX40), TNFRSF5 (CD40), TNFRSF6 (CD95, FAS receptor), TNFRSF7 (CD27), TNFRSF8 (CD30), TNFRSF9 (CD137, 4-1BB), TNFRSF10A (CD261), TNFRSF10B (TRAIL, DR5, CD262), TNFRSF10C, TNFRSF10D, TNFRSF11A, TNFRSF11B (OPG), TNFRSF12A, TNFRSF13B, TNFR13C, (CD268, BAFFR), TNFRSF14 (CD270, LIGHTR), TNFRSF16, TNFRSF17 (CD269, BCMA), TNFRSF18 (GITR, CD357), TNFRSF19, TNFRSF21, TNFRSF25; NCBI Gene IDs: 355, 608, 939, 943, 958, 3604, 4804, 4982, 7132, 7133, 7293, 8718, 8764, 8784, 8792, 8793, 8794, 8795, 8797, 23495, 27242, 51330, 55504); tumor protein p53 (TP53; NCBI Gene ID: 7157); tumor suppressor 2, mitochondrial calcium regulator (TUSC2; NCBI Gene ID: 11334); TYRO3 protein tyrosine kinase (TYRO3; BYK; NCBI Gene ID: 7301); tyrosinase (TYR; NCBI Gene ID: 7299); tyrosine hydroxylase (TH; NCBI Gene ID: 7054); tyrosine kinase with immunoglobulin like and EGF like domains 1 (e.g., TIE1, TIE1; NCBI Gene ID: 7075); tyrosine-protein phosphatase non-receptor type 11 (PTPN11, SHP2; NCBI Gene ID: 5781); ubiquitin conjugating enzyme E2 I (UBE2I, UBC9; NCBI Gene ID: 7329); ubiquitin C-terminal hydrolase L5 (UCHL5; NCBI Gene ID: 51377); ubiquitin specific peptidase 7 (USP7; NCBI Gene ID: 7874); ubiquitin-like modifier activating enzyme 1 (UBA1; NCBI Gene ID: 7317); UL16 binding proteins (e.g., ULBP1, ULBP2, ULBP3; NCBI Gene ID: 79465, 80328, 80328); valosin-containing protein (VCP, CDC48; NCBI Gene ID: 7415); vascular cell adhesion molecule 1 (VCAM1, CD106; NCBI Gene ID: 7412); vascular endothelial growth factors (e.g., VEGFA, VEGFB; NCBI Gene ID: 7422, 7423); vimentin (VIM; NCBI Gene ID: 7431); vitamin D receptor (VDR; NCBI Gene ID: 7421); V-set domain containing T cell activation inhibitor 1 (VTCN1, B7-H4; NCBI Gene ID: 79679); V-set immunoregulatory receptor (VSIR, VISTA, B7-H5; NCBI Gene ID: 64115); WEE1 G2 checkpoint kinase (WEE1; NCBI Gene ID: 7465); WRN RecQ like helicase (WRN; RECQ3; NCBI Gene ID: 7486); WT1 transcription factor (WT1; NCBI Gene ID: 7490); WW domain containing transcription regulator 1 (WWTR1; TAZ; NCBI Gene ID: 25937); X-C motif chemokine ligand 1 (XCL1, ATAC; NCBI Gene ID: 6375); X-C motif chemokine receptor 1 (XCR1, GPRS, CCXCR1; NCBI Gene ID: 2829); Yes1 associated transcriptional regulator (YAP1; NCBI Gene ID: 10413); zeta chain associated protein kinase 70 (ZAP70; NCBI Gene ID: 7535).

In some embodiments, the one or more additional therapeutic agents include, e.g., an agent targeting 5'-nucleotidase ecto (NT5E or CD73; NCBI Gene ID: 4907); adenosine $A_{2A}$ receptor (ADORA2A; NCBI Gene ID: 135); adenosine $A_{2B}$ receptor (ADORA2B; NCBI Gene ID: 136); C-C motif chemokine receptor 8 (CCR8, CDw198; NCBI Gene ID: 1237); cytokine inducible SH2 containing protein (CISH; NCBI Gene ID: 1154); diacylglycerol kinase alpha (DGKA, DAGK, DAGK1 or DGK-alpha; NCBI Gene ID: 1606); fms like tyrosine kinase 3 (FLT3, CD135; NCBI Gene ID: 2322); integrin associated protein (IAP, CD47; NCBI Gene ID: 961); interleukine-2 (IL2; NCBI Gene ID:3558); interleukine 2 receptor (IL2RA, IL2RB, IL2RG; NCBI Gene IDs: 3559, 3560, 3561); Kirsten rat sarcoma virus (KRAS; NCBI Gene ID: 3845; including mutations, such as KRAS G12C or G12D); mitogen-activated protein kinase kinase kinase kinase 1 (MAP4K1) (also called Hematopoietic Progenitor Kinase 1 (HPK1), NCBI Gene ID: 11184); myeloid cell leukemia sequence 1 apoptosis regulator (MCL1; NCBI Gene ID: 4170); phosphatidylinositol-4,5-bisphosphate 3-kinase, catalytic subunit delta (PIK3CD; NCBI Gene ID: 5293); programmed death-ligand 1 (PD-L1, CD274; NCBI Gene ID 29126); programmed cell death protein 1 (PD-1, CD279; NCBI Gene ID: 5133); proto-oncogen c-KIT (KIT, CD117; NCBI Gene ID: 3815); signal-regulatory protein alpha (SIRPA, CD172A; NCBI Gene ID: 140885); TCDD inducible poly(ADP-ribose) polymerase (TIPARP, PARP7; NCBI Gene ID: 25976); T cell immunoreceptor with Ig and ITIM domains (TIGIT; NCBI Gene ID: 201633); triggering receptor expressed on myeloid cells 1 (TREM1; NCBI Gene ID: 54210); triggering receptor expressed on myeloid cells 2 (TREM2; NCBI Gene ID: 54209); tumor-associated calcium signal transducer 2 (TACSTD2, TROP2, EGP1; NCBI Gene ID: 4070); tumor necrosis factor receptor superfamily, member 4 (TNFRSF4, CD134, OX40; NCBI Gene ID:7293); tumor necrosis factor receptor superfamily, member 9 (TNFRSF9, 4-1BB, CD137; NCBI Gene ID: 3604); tumor necrosis factor receptor superfamily, member 18 (TNFRSF18, CD357, GITR; NCBI Gene ID: 8784); WRN RecQ like helicase (WRN; NCBI Gene ID: 7486); zinc finger protein Helios (IKZF2; NCBI Gene ID: 22807).

Illustrative Mechanisms of Action
Immune Checkpoint Modulators

In some embodiments an Compound provided herein is administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res.* (2018) 37:110). In some embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688). Inhibition of regulatory T-cells (Treg) or Treg depletion can alleviate their suppression of antitumor immune responses and have anticancer effects (e.g., reviewed in Plitas and Rudensky, *Annu. Rev. Cancer Biol.* (2020) 4:459-77; Tanaka and Sakaguchi, *Eur. J. Immunol.* (2019) 49:1140-1146).

Examples of immune checkpoint proteins or receptors include CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80

(B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAETIE; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLEC15A, MAFA, 2F1; NCBI Gene ID: 10219); sialic acid binding Ig like lectin 7 (SIGLEC7; NCBI Gene ID: 27036); and sialic acid binding Ig like lectin 9 (SIGLEC9; NCBI Gene ID: 27180).

In some embodiments an Compound provided herein is administered with one or more blockers or inhibitors of one or more T-cell inhibitory immune checkpoint proteins or receptors. Illustrative T-cell inhibitory immune checkpoint proteins or receptors include CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the Compound provided herein is administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In some embodiments the Compound provided herein is administered with one or more blockers or inhibitors of one or more NK-cell inhibitory immune checkpoint proteins or receptors. Illustrative NK-cell inhibitory immune checkpoint proteins or receptors include killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments the Compound provided herein is administered with one or more agonist or activators of one or more NK-cell stimulatory immune checkpoint proteins or receptors. Illustrative NK-cell stimulatory immune checkpoint proteins or receptors include CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments the one or more immune checkpoint inhibitors comprises a proteinaceous (e.g., antibody or fragment thereof, or antibody mimetic) inhibitor of PD-L1 (CD274), PD-1 (PDCD1), CTLA4, or TIGIT. In some embodiments the one or more immune checkpoint inhibitors comprises a small organic molecule inhibitor of PD-L1 (CD274), PD-1 (PDCD1), CTLA4, or TIGIT. In some embodiments the one or more immune checkpoint inhibitors comprises a proteinaceous (e.g., antibody or fragment thereof, or antibody mimetic) inhibitor of LAG3.

Examples of inhibitors of CTLA4 that can be co-administered include ipilimumab, tremelimumab, BMS-986218, AGEN1181, zalifrelimab (AGEN1884), BMS-986249, MK-1308, REGN-4659, ADU-1604, CS-1002 (ipilimumab biosimilar), BCD-145, APL-509, JS-007, BA-3071, ONC-392, AGEN-2041, HBM-4003, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include pembrolizumab, nivolumab, cemiplimab, pidilizumab, AMP-224, MEDI0680 (AMP-514), spartalizumab, atezolizumab, avelumab, durvalumab, BMS-936559, cosibelimab (CK-301), sasanlimab (PF-06801591), tislelizumab (BGB-A317), GLS-010 (WBP-3055), AK-103 (HX-008), AK-105, CS-1003, HLX-10, retifanlimab (MGA-012), BI-754091, balstilimab (AGEN-2034), AMG-404, toripalimab (JS-001), cetrelimab (JNJ-63723283), genolimzumab (CBT-501), LZM-009, prolgolimab (BCD-100), lodapolimab (LY-3300054), SHR-1201, camrelizumab (SHR-1210), Sym-021, budigalimab (ABBV-181), PD1-PIK, BAT-1306, avelumab (MSB0010718C), CX-072, CBT-502, dostarlimab (TSR-042), MSB-2311, JTX-4014, BGB-A333, SHR-1316, CS-1001 (WBP-3155, envafolimab (KN-035), sintilimab (IBI-308), HLX-20, KL-A167, STI-A1014, STI-A1015 (IMC-001), BCD-135, FAZ-053, TQB-2450, MDX1105-01, GS-4224, GS-4416, INCB086550, MAX10181, zimberelimab (AB122), spartalizumab (PDR-001), and compounds disclosed in WO2018195321, WO2020014643, WO2019160882, or WO2018195321, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1), RO-7247669 (PD-1/LAG-3), MGD-019 (PD-1/CTLA4), KN-046 (PD-1/CTLA4), MEDI-5752 (CTLA4/PD-1), RO-7121661 (PD-1/TIM-3), RG7769 (PD-1/TIM-3), TAK-252 (PD-1/OX40L), XmAb-20717 (PD-1/CTLA4), AK-104 (CTLA4/PD-1), FS-118 (LAG-3/PD-L1), FPT-155 (CTLA4/PD-L1/CD28), GEN-1046 (PD-L1/4-1BB), bintrafusp alpha (M7824; PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments the PD-L1 inhibitor is a small molecule inhibitor, such as CA-170, GS-4224, GS-4416 and lazertinib (GNS-1480; PD-L1/EGFR).

Examples of inhibitors of TIGIT that can be co-administered include tiragolumab (RG-6058), vibostolimab, domvanalimab, domvanalimab (AB154), AB308, BMS-986207, AGEN-1307, COM-902, or etigilimab.

Examples of inhibitors of LAG3 that can be co-administered include leramilimab (LAG525). Inhibition of regulatory T-cell (Treg) activity or Treg depletion can alleviate their suppression of antitumor immune responses and have anticancer effects. See, e.g., Plitas and Rudensky, *Annu. Rev. Cancer Biol.* (2020) 4:459-77; Tanaka and Sakaguchi, *Eur. J. Immunol.* (2019) 49:1140-1146. In some embodiments, an Compound provided herein is administered with one or more inhibitors of Treg activity or a Treg depleting agent. Treg inhibition or depletion can augment the effect of immune checkpoint inhibitors in cancer therapeutics.

In some embodiments an Compound provided herein is administered with one or more Treg inhibitors. In some embodiments the Treg inhibitor can suppress the migration of Tregs into the tumor microenvironment. In some embodiments Treg inhibitor can reduce the immunosuppressive function of Tregs. In some embodiments, the Treg inhibitor can modulate the cellular phenotype and induce production of proinflammatory cytokines. Exemplary Treg inhibitors include without limitation, CCR4 (NCBI Gene ID: 1233) antagonists and degraders of Ikaros zinc-finger proteins (e.g., Ikaros (IKZF1; NCBI Gene ID: 10320), Helios (IKZF2; NCBI Gene ID: 22807), Aiolos (IKZF3; NCBI Gene ID: 22806), and Eos (IKZF4; NCBI Gene ID: 64375).

Examples of Helios degraders that can be co-administered include without limitation I-57 (Novartis) and compounds disclosed in WO2019038717, WO2020012334, WO20200117759, and WO2021101919.

In some embodiments an Compound provided herein is administered with one or more Treg depleting agents. In some embodiments the Treg depleting agent is an antibody. In some embodiments the Treg depleting antibody has antibody-dependent cytotoxic (ADCC) activity. In some embodiments, the Treg depleting antibody is Fc-engineered to possess an enhanced ADCC activity. In some embodiments the Treg depleting antibody is an antibody-drug conjugate (ADC). Illustrative targets for Treg depleting agents include without limitation CD25 (IL2RA; NCBI Gene ID: 3559), CTLA4 (CD152; NCBI Gene ID: 1493); GITR (TNFRSF18; NCBI Gene ID: 8784); 4-1BB (CD137; NCBI Gene ID: 3604), OX-40 (CD134; NCBI Gene ID: 7293), LAG3 (CD223; NCBI Gene ID: 3902), TIGIT (NCBI Gene ID: 201633), CCR4 (NCBI Gene ID: 1233), and CCR8 (NCBI Gene ID: 1237).

In some embodiments the Treg inhibitor or Treg depleting agent that can be co-administered comprises an antibody or antigen-binding fragment thereof that selectively binds to a cell surface receptor selected from the group consisting of C-C motif chemokine receptor 4 (CCR4), C-C motif chemokine receptor 7 (CCR7), C-C motif chemokine receptor 8 (CCR8), C-X-C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ectonucleotide triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL2RA (CD25) or a combination thereof.

Examples of Treg depleting anti-CCR8 antibodies that can be administered include without limitation JTX-1811 (GS-1811) (Jounce Therapeutics, Gilead Sciences), BMS-986340 (Bristol Meyers Squibb), S-531011 (Shionogi), FPA157 (Five Prime Therapeutics), SRF-114 (Surface Oncology), HBM1022 (Harbor BioMed), IO-1 (Oncurious), and antibodies disclosed in WO2021163064, WO2020138489, and WO2021152186.

Examples of Treg depleting anti-CCR4 antibodies that can be administered include mogamulizumab.

Inhibiting, depleting, or reprogramming of non-stimulatory myeloid cells in the tumor microenvironment can enhance anti-cancer immune responses (see, e.g., Binnewies et al., *Nat. Med.* (2018) 24(5): 541-550; WO2016049641). Illustrative targets for depleting or reprogramming non-stimulatory myeloid cells include triggering receptors expressed on myeloid cells, TREM-1 (CD354, NCBI Gene ID: 54210) and TREM-2 (NCBI Gene ID: 54209). In some embodiments an Compound provided herein is administered with one or more myeloid cell depleting or reprogramming agents, such as an anti-TREM-1 antibody (e.g. PY159; antibodies disclosed in WO2019032624) or an anti-TREM-2 antibody (e.g., PY314; antibodies disclosed in WO2019118513).

Cluster of Differentiation Agonists or Activators

In some embodiments, the Compound provided herein is administered with agents targeting a cluster of differentiation (CD) marker. Exemplary CD marker targeting agents that can be co-administered include without limitation A6, AD-IL24, neratinib, tucatinib (ONT 380), mobocertinib (TAK-788), tesevatinib, trastuzumab (HERCEPTIN®), trastuzumab biosimimar (HLX-02), margetuximab, BAT-8001, pertuzumab (Perjeta), pegfilgrastim, RG6264, zanidatamab (ZW25), cavatak, AIC-100, tagraxofusp (SL-401), HLA-A2402/HLA-A0201 restricted epitope peptide vaccine, dasatinib, imatinib, nilotinib, sorafenib, lenvatinib mesylate, ofranergene obadenovec, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, olverembatinib dimesylate (HQP-1351), cabozantinib, ponatinib, and famitinib L-malate, CX-2029 (ABBV-2029), SCB-313, CA-170, COM-701, CDX-301, GS-3583, asunercept (APG-101), APO-010, and compounds disclosed in WO2016196388, WO2016033570, WO2015157386, WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, PCT/US2019/063091, WO19173692, WO2016179517, WO2017096179, WO2017096182, WO2017096281, WO2018089628, WO2017096179, WO2018089628, WO2018195321, WO2020014643, WO2019160882, WO2018195321, WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, WO2020068752, Cancer Discov. 2019 Jan. 9(1):8; and Gariepy J., et al. 106th Annu Meet Am Assoc Immunologists (AAI) (May 9-13, San Diego, 2019, Abst 71.5).

In some embodiments the CD marker targeting agent that can be co-administered include small molecule inhibitors, such as PBF-1662, BLZ-945, pemigatinib (INCB-054828), rogaratinib (BAY-1163877), AZD4547, roblitinib (FGF-401), quizartinib dihydrochloride, SX-682, AZD-5069, PLX-9486, avapritinib (BLU-285), ripretinib (DCC-2618), imatinib mesylate, JSP-191, BLU-263, CD117-ADC, AZD3229, telatinib, vorolanib, GO-203-2C, AB-680, PSB-12379, PSB-12441, PSB-12425, CB-708, HM-30181A, motixafortide (BL-8040), LY2510924, burixafor (TG-0054), X4P-002, mavorixafor (X4P-001-IO), plerixafor, CTX-5861, or REGN-5678 (PSMA/CD28).

In some embodiments the CD marker targeting agent that can be co-administered include small molecule agonists, such as interleukin 2 receptor subunit gamma, eltrombopag, rintatolimod, poly-ICLC (NSC-301463), Riboxxon, Apoxxim, RIBOXXIM®, MCT-465, MCT-475, G100, PEPA-10, eftozanermin alfa (ABBV-621), E-6887, motolimod, resiquimod, selgantolimod (GS-9688), VTX-1463, NKTR-262, AST-008, CMP-001, cobitolimod, tilsotolimod, litenimod, MGN-1601, BB-006, IMO-8400, IMO-9200, agatolimod, DIMS-9054, DV-1079, lefitolimod (MGN-1703), CYT-003, and PUL-042.

In some embodiments the CD marker targeting agent that can be co-administered include antibodies, such as tafasitamab (MOR208; MorphoSys AG), Inebilizumab (MEDI-551), obinutuzumab, IGN-002, rituximab biosimilar (PF-05280586), varlilumab (CDX-1127), AFM-13 (CD16/CD30), AMG330, otlertuzumab (TRU-016), isatuximab, felzartamab (MOR-202), TAK-079, TAK573, daratumumab (DARZALEX®), TTX-030, selicrelumab (RG7876), APX-005M, ABBV-428, ABBV-927, mitazalimab (JNJ-64457107), lenziluma, alemtuzuma, emactuzumab, AMG-820, FPA-008 (cabiralizumab), PRS-343 (CD-137/Her2), AFM-13 (CD16/CD30), belantamab mafodotin (GSK-2857916), AFM26 (BCMA/CD16A), simlukafusp alfa (RG7461), urelumab, utomilumab (PF-05082566), AGEN2373, ADG-106, BT-7480, PRS-343 (CD-137/HER2), FAP-4-IBBL (4-1BB/FAP), ramucirumab, CDX-0158, CDX-0159 and FSI-174, relatlimab (ONO-4482), LAG-525, MK-4280, fianlimab (REGN-3767), INCAGN2385, encelimab (TSR-033), atipotuzumab, BrevaRex (Mab-AR-20.5), MEDI-9447 (oleclumab), CPX-006, IPH-53, BMS-986179, NZV-930, CPI-006, PAT-SC1, lirilumab (IPH-2102), lacutamab (IPH-4102), monalizumab, BAY-1834942, NEO-201 (CEACAM 5/6), Iodine (131I) apamistamab (131I-BC8 (lomab-B)), MED10562 (tavolixizumab), GSK-3174998, INCAGN1949, BMS-986178, GBR-8383, ABBV-368, denosumab, BION-1301, MK-4166, INCAGN-1876, TRX-518, BMS-986156, MK-1248, GWN-323, CTB-006, INBRX-109, GEN-1029, pepinemab (VX-15), vopratelimab (JTX-2011), GSK3359609, cobolimab (TSR-022), MBG-453, INCAGN-2390, and compounds disclosed in WO 2017096179, WO2017096276, WO2017096189, and WO2018089628.

In some embodiments the CD marker targeting agent that can be co-administered include cell therapies, such as CD19-ARTEMIS, TBI-1501, CTL-119 huCART-19 T cells, 1 iso-cell, lisocabtagene maraleucel (JCAR-017), axicabtagene ciloleucel (KTE-C19, Yescarta®), axicabtagene ciloleucel (KTE-X19), U.S. Pat. Nos. 7,741,465, 6,319,494, UCART-19, tabelecleucel (EBV-CTL), T tisagenlecleucel-T (CTL019), CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110, anti-CD19 CAR T-cell therapy (B-cell acute lymphoblastic leukemia, Universiti Kebangsaan Malaysia), anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem, UCAR-011, ICTCAR-014, GC-007F, PTG-01, CC-97540, GC-007G, TC-310, GC-197, tisagenlecleucel-T, CART-19, tisagenlecleucel (CTL-019)), anti-CD20 CAR T-cell therapy (non-Hodgkin's lymphoma), MB-CART2019.1 (CD19/CD20), WZTL-002 dual anti-CD19/anti-CD20 CAR-T cells, ICG-132 (CD19/CD20), ACTR707 ATTCK-20, PBCAR-20A, LB-1905, CIK-CAR.CD33, CD33CART, dual anti-BCMA/anti-CD38 CAR T-cell therapy, CART-ddBCMA, MB-102, IM-23, JEZ-567, UCART-123, PD-1 knockout T cell therapy (esophageal cancer/NSCLC), ICT-CAR-052, Tn MUC-1 CAR-T, ICTCAR-053, PD-1 knockout T cell therapy (esophageal cancer/NSCLC), AUTO-2, anti-BCMA CAR T-cell therapy, Descartes-011, anti-BCMA/anti-CD38 CAR T-cell therapy, CART-ddBCMA, BCMA-CS1 cCAR, CYAD-01 (NKG2D LIGAND MODULATOR), KD-045, PD-L1 t-haNK, BCMA-CS1 cCAR, MED15083, anti-CD276 CART, and therapies disclosed in WO2012079000 or WO2017049166.

Cluster of Differentiation 47 (CD47) Inhibitors

In some embodiments the Compound provided herein is administered with an inhibitor of CD47 (IAP, MER6, OA3; NCBI Gene ID: 961). Examples of CD47 inhibitors include anti-CD47 mAbs (Vx-1004), anti-human CD47 mAbs (CNTO-7108), CC-90002, CC-90002-ST-001, humanized anti-CD47 antibody or a CD47-blocking agent, NI-1701, NI-1801, RCT-1938, ALX148, SG-404, SRF-231, and TTI-621. Additional exemplary anti-CD47 antibodies include CC-90002, magrolimab (Hu5F9-G4), AO-176 (Vx-1004), letaplimab (IBI-188) (letaplimab), lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, ALX-148, AK-117, TTI-621, TTI-622, or compounds disclosed in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, and WO2020009725. In some embodiments, the CD47 inhibitor is RRx-001, DSP-107, VT-1021, IMM-02, SGN-CD47M, or SIRPa-Fc-CD40L (SL-172154). In some embodiments the CD47 inhibitor is magrolimab.

In some embodiments, the CD47 inhibitor is a bispecific antibodies targeting CD47, such as IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801.

SIRPa Targeting Agents

In some embodiments the Compound provided herein is administered with a SIRPa targeting agent (NCBI Gene ID: 140885; UniProt P78324). Examples of SIRPa targeting agents include SIRPa inhibitors, such as AL-008, RRx-001, and CTX-5861, and anti-SIRPa antibodies, such as FSI-189 (GS-0189), ES-004, BI-765063, ADU1805, CC-95251, Q-1801 (SIRPa/PD-L1). Additional SIRPa-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

FLT3R Agonists

In some embodiments the Compound provided herein is administered with a FLT3R agonist. In some embodiments, the Compound provided herein is administered with a FLT3 ligand. In some embodiments, the Compound provided herein is administered with a FLT3L-Fc fusion protein, e.g., as described in WO2020263830. In some embodiments the Compound provided herein is administered with GS-3583 or CDX-301. In some embodiments the Compound provided herein is administered with GS-3583.

TNF Receptor Superfamily (TNFRSF) Member Agonists or Activators

In some embodiments, the Compound provided herein is administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include MEDI6469, MEDI6383, tavolixizumab (MEDI0562), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include RG7876, SEA-CD40, APX-005M, and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include urelumab, utomilumab (PF-05082566), AGEN-2373, and ADG-106.

In some embodiments the anti-TNFRSF17 (BCMA) antibody GSK-2857916 is co-administered.

Example anti-TNFRSF18 (GITR) antibodies that can be co-administered include MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include PRS-343 (CD-137/HER2), AFM26 (BCMA/CD16A), AFM-13 (CD16/CD30), odronextamab (REGN-1979; CD20/CD3), AMG-420 (BCMA/CD3), INHIBRX-105 (4-1BB/PDL1), FAP-4-IBBL (4-1BB/FAP), plamotamab (XmAb-13676; CD3/CD20), RG-7828 (CD20/CD3), CC-93269 (CD3/BCMA), REGN-5458 (CD3/BCMA), and IMM-0306 (CD47/CD20).

Bi-Specific T-Cell Engagers

In some embodiments Compound provided herein is administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include duvortuxizumab (JNJ-64052781; CD19/CD3), AMG-211 (CEA/CD3), AMG-160 (PSMA/CD3), RG7802 (CEA/CD3), ERY-974 (CD3/GPC3), PF-06671008 (Cadherins/CD3), APV0436 (CD123/CD3), flotetuzumab (CD123/CD3), odronextamab (REGN-1979; CD20/CD3), MCLA-117 (CD3/CLEC12A), JNJ-0819 (heme/CD3), JNJ-7564 (CD3/heme), AMG-757 (DLL3-CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), AMG-211 (CEA/CD3), blinatumomab (CD19/CD3), huGD2-BsAb (CD3/GD2), ERY974 (GPC3/CD3), GEMoab (CD3/PSCA), RG6026 (CD20/CD3), RG6194 (HER2/CD3), PF-06863135 (BCMA/CD3), SAR440234 (CD3/CDw123), JNJ-9383 (MGD-015), AMG-424 (CD38/CD3), tidutamab (XmAb-18087 (SSTR2/CD3)), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), tidutamab (XmAb-18087; SSTR2/CD3), catumaxomab (CD3/EpCAM), REGN-4018 (MUC16/CD3), mosunetuzumab (RG-7828; CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., Oncoimmunology. (2017) May 17; 6(7):e1326437); PD-L1 (Horn, et al., Oncotarget. 2017 Aug. 3; 8(35):57964-57980); and EGFRvIII (Yang, et al., Cancer Lett. 2017 Sep. 10; 403:224-230).

Bi- and Tri-Specific Natural Killer (NK)-Cell Engagers

In some embodiments the Compound provided herein is administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., Methods Mol Biol. (2016) 1441:333-346; Fang, et al., Semin Immunol. (2017) 31:37-54.

MCL1 Apoptosis Regulator, BCL2 Family Member (MCL1) Inhibitors

In some embodiments the Compound provided herein is administered with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include tapotoclax (AMG-176), AMG-397, 5-64315, AZD-5991, 483-LM, A-1210477, UMI-77, JKY-5-037, PRT-1419, GS-9716, and those described in WO2018183418, WO2016033486, and WO2017147410.

SHP2 Inhibitors

In some embodiments Compound provided herein is administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, and those described in WO2018172984 and WO2017211303.

Hematopoietic Progenitor Kinase 1 (HPK1) Inhibitors and Degraders

In some embodiments, the Compound provided herein is administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO2020092621, WO2018183956, WO2018183964, WO2018167147, WO2018049152, WO2020092528, WO2016205942, WO2016090300, WO2018049214, WO2018049200, WO2018049191, WO2018102366, WO2018049152, and WO2016090300.

Apoptosis Signal-Regulating Kinase (ASK) Inhibitors

In some embodiments the Compound provided herein is administered with an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include those described in WO2011008709 (Gilead Sciences) and WO 2013112741 (Gilead Sciences).

Bruton Tyrosine Kinase (BTK) Inhibitors

In some embodiments the Compound provided herein is administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include (S)-6-amino-9-(1-(but-2-ynoyl)pyrrolidin-3-yl)-7-(4-phenoxyphenyl)-7H-purin-8(9H)-one, acalabrutinib (ACP-196), zanubrutinib (BGB-3111), CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, PCI-32765, and TAS-5315.

Cyclin-Dependent Kinase (CDK) Inhibitors

In some embodiments the Compound provided herein is administered with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1;

HCAK; MO15; STK1; CDKN7; p39MO15; NCBI Gene ID: 1022), or cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include abemaciclib, alvocidib (HMR-1275, flavopiridol), AT-7519, dinaciclib, ibrance, FLX-925, LEE001, palbociclib, samuraciclib, ribociclib, rigosertib, selinexor, UCN-01, SY1365, CT-7001, SY-1365, G1T38, milciclib, trilaciclib, simurosertib hydrate (TAK931), and TG-02.

Discoidin Domain Receptor (DDR) Inhibitors

In some embodiments the Compound provided herein is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In some embodiments the Compound provided herein is administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In some embodiments the targeted E3 ligase ligand conjugates comprise a targeting or binding moiety that targets or binds a protein described herein, and an E3 ligase ligand or binding moiety. In some embodiments the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In some embodiments the targeted E3 ligase ligand conjugates comprise a kinase inhibitor (e.g., a small molecule kinase inhibitor, e.g., of BTK and an E3 ligase ligand or binding moiety. See, e.g., WO2018098280. In some embodiments the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208, and WO2018144649.

Histone Deacetylase (HDAC) Inhibitors

In some embodiments the Compound provided herein is administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

Indoleamine-pyrrole-2,3-dioxygenase (IDO1) Inhibitors

In some embodiments the Compound provided herein is administered with an inhibitor of indoleamine 2,3-dioxygenase 1 (IDO1; NCBI Gene ID: 3620). Examples of IDO1 inhibitors include BLV-0801, epacadostat, linrodostat (F-001287, BMS-986205), GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST, EOS-200271, KHK-2455, and LY-3381916.

Janus Kinase (JAK) Inhibitors

In some embodiments, the Compound provided herein is administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include AT9283, AZD1480, baricitinib, BMS-911543, fedratinib, filgotinib (GLPG0634), gandotinib (LY2784544), INCB039110 (itacitinib), lestaurtinib, momelotinib (CYT0387), ilginatinib maleate (NS-018), pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In some embodiments the Compound provided herein is administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL2 inhibitors include the antibodies described in WO 2009017833 (Arresto Biosciences), WO 2009035791 (Arresto Biosciences), and WO 2011097513 (Gilead Biologics).

Matrix Metalloprotease (MMP) Inhibitors

In some embodiments the Compound provided herein is administered with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include marimastat (BB-2516), cipemastat (Ro 32-3555), GS-5745 (andecaliximab), and those described in WO 2012027721 (Gilead Biologics).

RAS and RAS Pathway Inhibitors

In some embodiments the Compound provided herein is administered with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893) or HRAS proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID:

3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include sotorasib (AMG-510), COTI-219, ARS-3248, WDB-178, BI-3406, BI-1701963, SML-8-73-1 (G12C), adagrasib (MRTX-849), ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 and KRpep-2d. Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered include BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, inavolisib (RG6114), ASN-003. Illustrative AKT inhibitors that can be co-administered include capivasertib and GSK2141795. Illustrative PI3K/mTOR inhibitors that can be co-administered include dactolisib, omipalisib, voxtalisib. gedatolisib, GSK2141795, GSK-2126458, inavolisib (RG6114), sapanisertib, ME-344, sirolimus (oral nano-amorphous formulation, cancer), racemetyrosine (TYME-88 (mTOR/cytochrome P450 3A4)), temsirolimus (TORISEL®, CCI-779), CC-115, onatasertib (CC-223), SF-1126, and PQR-309 (bimiralisib). In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

Mitogen-Activated Protein Kinase (MEK) Inhibitors

In some embodiments the Compound provided herein is administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib.

Phosphatidylinositol 3-kinase (PI3K) Inhibitors

In some embodiments Compound provided herein is administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments the PI3K inhibitor is a pan-PI3K inhibitor. Examples of PI3K inhibitors include ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO2005113556 (ICOS), WO 2013/052699 (Gilead Calistoga), WO2013116562 (Gilead Calistoga), WO2014100765 (Gilead Calistoga), WO2014100767 (Gilead Calistoga), and WO2014201409 (Gilead Sciences).

Spleen Tyrosine Kinase (SYK) Inhibitors

In some embodiments the Compound provided herein is administered with an inhibitor of spleen associated tyrosine kinase (SYK, p72-Syk, NCBI Gene ID: 6850). Examples of SYK inhibitors include 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), gusacitinib (ASN-002), and those described in U.S. Pat. No. 8,450,321 (Gilead Connecticut) and US20150175616.

Toll-Like Receptor (TLR) Agonists

In some embodiments Compound provided herein is administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, BDB-001, DSP-0509, and the compounds disclosed in US20100143301 (Gilead Sciences), US20110098248 (Gilead Sciences), and US20090047249 (Gilead Sciences), US20140045849 (Janssen), US20140073642 (Janssen), WO2014056953 (Janssen), WO2014076221 (Janssen), WO2014128189 (Janssen), US20140350031 (Janssen), WO2014023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-kinase Inhibitors (TKIs)

In some embodiments the Compound provided herein is administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). Exemplary EGFR targeting agents include neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596 (EGFRvIII/CD3), lifirafenib (BGB-283), vectibix, lazertinib (LECLAZA®), and compounds disclosed in Booth, et al., Cancer Biol Ther. 2018 Feb. 1; 19(2):132-137. Antibodies targeting EGFR include without limitation modotuximab, cetuximab sarotalocan (RM-1929), seribantumab, necitumumab, depatuxizumab mafodotin (ABT-414), tomuzotuximab, depatuxizumab (ABT-806), and cetuximab.

Chemotherapeutic Agents

In some embodiments the compounds provided herein is administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8;dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; sabizabulin (Veru-111); platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204, enobosarm (GTX-024), darolutamide, and IONIS-AR-2.5Rx (antisense).

An example progesterone receptor antagonist includes onapristone. Additional progesterone targeting agents include TRI-CYCLEN LO (norethindrone+ethinyl estradiol), norgestimate+ethinylestradiol (Tri-Cyclen) and levonorgestrel.

Anti-Angiogenic Agents

In some embodiments the compounds provided herein is administered with an anti-angiogenic agent. Anti-angiogenic agents that can be co-administered include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2 (3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2. Examples for anti-VEGFA antibodies that can be co-administered include bevacizumab, vanucizumab, faricimab, dilpacimab (ABT-165; DLL4/VEGF), or navicixizumab (OMP-305B83; DLL4/VEGF).

Anti-Fibrotic Agents

In some embodiments the compound provided herein is administered with an anti-fibrotic agent. Anti-fibrotic agents that can be co-administered include the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 20040248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments the compounds provided herein is administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include mofezolac, GLY-230, and TRK-700.

Examples of inhibitors of prostaglandin-endoperoxide synthase 2 (PTGS2, COX-2; NCBI Gene ID: 5743) that can be co-administered include diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, NS-398, pamicogrel, parecoxib, robenacoxib, rofecoxib, rutecarpine, tilmacoxib, and zaltoprofen. Examples of dual COX1/COX2 inhibitors that can be co-administered include HP-5000, lornoxicam, ketorolac tromethamine, bromfenac sodium, ATB-346, HP-5000. Examples of dual COX-2/carbonic anhydrase (CA) inhibitors that can be co-administered include polmacoxib and imrecoxib.

Examples of inhibitors of secreted phospholipase A2, prostaglandin E synthase (PTGES, PGES; Gene ID: 9536) that can be co-administered include LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett*. (2017) 389:23-32; and Liu, et al., *Oncotarget*. (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include meclofenamate sodium, zileuton.

Examples of inhibitors of soluble epoxide hydrolase 2 (EPHX2, SEH; NCBI Gene ID: 2053) that can be co-administered include compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include GS-4875, GS-5290, BHM-078 and those described in WO2006124944, WO2006124692, WO2014064215, WO2018005435, Teli, et al., *J Enzyme Inhib Med Chem*. (2012) 27(4):558-70; Gangwall, et al., *Curr Top Med Chem*. (2013) 13(9):1015-35; Wu, et al., *Bioorg Med Chem Lett*. (2009) 19(13):3485-8; Kaila, et al., *Bioorg Med Chem*. (2007) 15(19):6425-42; and Hu, et al., *Bioorg Med Chem Lett*. (2011) 21(16):4758-61.

Tumor Oxygenation Agents

In some embodiments the compounds provided herein is administered with an agent that promotes or increases tumor oxygenation or reoxygenation, or prevents or reduces tumor hypoxia. Illustrative agents that can be co-administered include, e.g., Hypoxia inducible factor-1 alpha (HIF-1α) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO2007137767, WO2007139791, WO2014107171, and WO2016149562.

Immunotherapeutic Agents

In some embodiments the compounds provided herein is administered with an immunotherapeutic agent. In some embodiments the immunotherapeutic agent is an antibody. Example immunotherapeutic agents that can be co-administered include abagovomab, AB308, ABP-980, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, camnidanilumab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab, and 3F8. Rituximab can be used for treating indolent B-cell cancers, including marginal-zone lymphoma, WM, CLL, and small lymphocytic lymphoma. A combination of rituximab and chemotherapy agents is especially effective.

The exemplified therapeutic antibodies can be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include gemtuzumab, brentuximab, belantamab (e.g., belantamab mafodotin), camidanlhmab (e.g., camidanlumab tesirine), trastuzumab (e.g., trastuzumab deruxtecan; trasuzumab emtansine), inotuzumab, glembatumumab, anetumab, mirvetuximab (e.g., mirvetuximab soravtansine), depatuxizumab, vadastuximab, labetuzumab, ladiratuzumab (e.g., ladiratuzumab vedotin), loncastuximab (e.g., loncastuximab tesirine), sacituzumab (e.g., sacituzumab govitecan), datopotamab (e.g., datopotamab deruxtecan; DS-1062; Dato-DXd), patritumab (e.g., patritumab deruxtecan), lifastuzumab, indusatumab, polatuzumab (e.g., polatuzumab vedotin), pinatuzumab, coltuximab, upifitamab (e.g., upifitamab rilsodotin), indatuximab, milatuzumab, rovalpituzumab (e.g., rov alpituzumiab tesirine), enfortumab (e.g., enfortumab vedotin), tisotumab (e.g., tisotumab vedotin), tusamitamab (e.g., tusamitamab ravtansine), disitamab (e.g., disitamab vedotin), telisotuzumab vedotin (ABBV-399), AGS-16C3F, ASG-22ME, AGS67E, AMG172, AMG575, BAY1129980, BAY1187982, BAY94-9343, GSK2857916, Humax-TF-ADC, IMGN289, IMGN151, IMGN529, IMGN632, IMGN853, IMGC936, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A, SYD985, DS-7300, XMT-1660, IMMU-130, and IMMU-140. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38). In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments the conjugated immune checkpoint inhibitor is a conjugated small molecule inhibitor of CD274 (PDL1, PD-L1), programmed cell death 1 (PDCD1, PD1, PD-1) or CTLA4. In some embodiments the conjugated small molecule inhibitor of CD274 or PDCD1 is selected from the group consisting of GS-4224, GS-4416, INCB086550 and MAX10181. In some embodiments the conjugated small molecule inhibitor of CTLA4 comprises BPI-002.

In some embodiments the ADCs that can be co-administered include an antibody targeting tumor-associated calcium signal transducer 2 (TROP-2; TACSTD2; EGP-1; NCBI Gene ID: 4070). Illustrative anti-TROP-2 antibodies include without limitation TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Klus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (Mediterranea Theranostic, LegoChem Biosciences), KD-065 (Nanjing KAEDI Biotech), and those described in WO2020016662 (Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585 (Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464 (LivTech/Chiome), U.S. Ser. No. 10/501,555 (Abruzzo Theranostic/Oncoxx), WO2018036428 (Sichuan Kelun Pharma), WO2013068946 (Pfizer), WO2007095749 (Roche), and WO2020094670 (SynAffix). In some embodiments, the anti-Trop-2 antibody is selected from hRS7, Trop-2-XPAT, and BAT-8003. In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. In some embodiments, the antibody-drug conjugate comprises an anti-Trop-2 antibody and an anticancer agent linked by a linker. In some embodiments, the linker includes the linkers disclosed in U.S. Pat. No. 7,999,083.

In some embodiments, the linker is CL2A. In some embodiments, the drug moiety of antibody-drug conjugate is a chemotherapeutic agent. In some embodiments, the chemotherapeutic agent is selected from doxorubcin (DOX), epirubicin, morpholinodoxorubicin (morpholino-DOX), cyanomorpholino-doxorubicin (cyanomorpholinoDOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38. In some embodiments the Compound provided herein is administered with sacituzumab govitecan.

In some embodiments the ADCs that can be co-administered include an antibody targeting carcinoembryonic antigen-related cell adhesion molecule 1 (CEACAM1; CD66a; NCBI Gene ID: 634). In some embodiments the CEACAM1 antibody is hMN-14 (e.g., as described in WO1996011013). In some embodiments the CEACAM1-ADC is as described in WO2010093395 (anti-CEACAM-1-CL2A-SN38). In some embodiments the Compound provided herein is administered with the CEACAM1-ADC IMMU-130.

In some embodiments the ADCs that can be co-administered include an antibody targeting MHC class II cell surface receptor encoded by the human leukocyte antigen complex (HLA-DR). In some embodiments the HLA-DR antibody is hL243 (e.g., as described in WO2006094192). In some embodiments the HLA-DR-ADC is as described in WO2010093395 (anti-HLA-DR-CL2A-SN38). In some embodiments the Compound provided herein is administered with the HLA-DR-ADC IMMU-140.

Cancer Gene Therapy and Cell Therapy

In some embodiments a compound provided herein is administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments the Compound provided herein is administered with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvlll); ganglioside G2 (GD2); ganglioside GD3 (αNeuSAc(2-8)αNeuSAc(2-3)βDGaip(1-4)bDGIcp(1-1) Cer); ganglioside GM3 (αNeuSAc(2-3)βDGalp(1-4) βDGlcp(1-1)Cer); TNF receptor superfamily member 17 (TNFRSF17, BCMA); Tn antigen ((Tn Ag) or (GalNAcu-Ser/Thr)); prostate-specific membrane antigen (PSMA); receptor tyrosine kinase-like orphan receptor 1 (RORI); tumor-associated glycoprotein 72 (TAG72); CD38; CD44v6; Carcinoembryonic antigen (CEA); epithelial cell adhesion molecule (EPCAM); B7H3 (CD276); KIT (CD117); interleukin-13 receptor subunit alpha-2 (IL-13Ra2 or CD213A2); mesothelin; interleukin 11 receptor alpha (IL-11Ra); prostate stem cell antigen (PSCA); protease serine 21 (Testisin or PRSS21); vascular endothelial growth factor receptor 2 (VEGFR2); Lewis(Y)antigen; CD24; platelet-derived growth factor receptor beta (PDGFR-beta); stage-specific embryonic antigen-4 (SSEA-4); CD20; delta like 3 (DLL3); folate receptor alpha; receptor tyrosine-protein kinase, ERBB2 (Her2/neu); mucin 1, cell surface associated (MUC1); epidermal growth factor receptor (EGFR); neural cell adhesion molecule (NCAM); prostase; prostatic acid phosphatase (PAP); elongation factor 2 mutated (ELF2M); ephrin B2; fibroblast activation protein alpha (FAP); insulin-like growth factor 1 receptor (IGF-I receptor), carbonic anhydrase IX (CAIX); proteasome (Prosome, Macropain) subunit, beta type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); fucosyl GM1; sialyl Lewis adhesion molecule (sLe); transglutaminase 5 (TGS5); high molecular weight-melanomaassociatedantigen (HMW-MAA); o-acetyl-GD2 ganglioside (OAcGD2); folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CX-ORF61); CD97; CD179a; anaplastic lymphoma kinase (ALK); polysialic acid; placenta-specific 1 (PLAC1); hexasaccharide portion of globoH glycoceramide (GloboH); mammary gland differentiation antigen (NY-BR-1); uroplakin 2 (UPK2); hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); olfactory receptor 51E2 (ORS IE2); TCR Gamma Alternate Reading Frame Protein (TARP); Wilms tumor protein (WT1); cancer/testis antigen 1 (NY-ESO-1); cancer/testis antigen 2 (LAGE-1a); melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); fos-related antigen 1; tumor protein p53, (p53); p53 mutant; prostein; survivin; telomerase; prostate carcinoma tumor antigen-I (PCTA-1 or Galectin 8), melanoma antigen recognized by T cells 1 (MelanA or MARTI); rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TM-PRSS2) ETS fusion gene); N-Acetyl glucosaminyl-transferase V (NA17); paired box protein Pax-3 (PAX3); androgen receptor; cyclin B1; v-myc avian myelocytomatosis viral oncogene neuroblastoma derived homolog (MYCN); ras homolog family member C (RhoC); tyrosinase-related protein 2 (TRP-2); cytochrome P450 1B1(CYP IBI); CCCTC-Binding Factor (Zinc Finger Protein)-Like (BORIS or Brother of the Regulator of Imprinted Sites), squamous cell carcinoma antigen recognized by T-cells 3 (SART3); paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); receptor for advanced glycation endproducts (RAGE-I); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; leukocyte-associated immunoglobulin-like receptor 1 (LAIRI); Fc fragment of IgA receptor (FCAR or CD89); leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PR02000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen 1A (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGBIL1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; CORI, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPSIL1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Natl Acad Sci USA*. 2009 Apr. 7; 106(14): 5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Examples of cell therapies include: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H111-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments the one or more additional co-administered therapeutic agents can be categorized by their mechanism of action, e.g., into the following groups:

agents targeting adenosine deaminase, such as pentostatin or cladribine;

agents targeting ATM, such as AZD1390;

agents targeting MET, such as savolitinib, capmatinib, tepotinib, ABT-700, AG213, JNJ-38877618 (OMO-1), merestinib, HQP-8361, BMS-817378, or TAS-115;

agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4): 558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;

agents targeting thymidine kinase, such as aglatimagene besadenovec (ProstAtak, PancAtak, GliAtak, GMCI, or AdV-tk);

agents targeting an interleukin pathway, such as pegilodecakin (AM-0010) (pegylated IL10), CA-4948 (IRAK4 inhibitor);

agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);

agents targeting CD73, such as a CD73 inhibitor (e.g., quemliclustat (AB680)) or an anti-CD73 antibody (e.g., oleclumab);

agents targeting DKK3, such as MTG-201;

agents targeting EEF1A2, such as plitidepsin;

agents targeting EIF4A1, such as rohinitib;

agents targeting endoglin, such as TRC105 (carotuximab);

agents targeting exportin-1, such as eltanexor;

agents targeting fatty acid amide hydrolase, such as compounds disclosed in WO2017160861;

agents targeting heat shock protein 90 beta family member 1, such as anlotinib;

agents targeting lactotransferrin, such as ruxotemitide (LTX-315);

agents targeting lysyl oxidase, such as compounds disclosed in U.S. Pat. Nos. 4,965,288, 4,997,854, 4,943,593, 5,021,456, 5,059,714, 5,120,764, 5,182,297, 5,252,608, or US20040248871;

agents targeting MAGE family members, such as KITE-718, MAGE-A10C796T, or MAGE-A10TCR;

agents targeting MDM2, such as ALRN-6924, CMG-097, milademetan monotosylate monohydrate (DS-3032b), or AMG-232;

agents targeting MDM4, such as ALRN-6924;

agents targeting melan-A, such as MART-1 F5 TCR engineered PBMCs;

agents targeting mesothelin, such as CSG-MESO or TC-210;

agents targeting METAP2, such as M8891 or APL-1202;

agents targeting NLRP3, such as BMS-986299;

agents targeting oxoglutarate dehydrogenase, such as devimistat (CPI-613);

agents targeting placenta growth factor, such as aflibercept;

agents targeting SLC10A3, such as compounds disclosed in WO2015148954, WO2012082647, or WO2017160861;

agents targeting transforming growth factor alpha (TGFa), such as compounds disclosed in WO2019103203;

agents targeting tumor protein p53, such as kevetrin (stimulator);

agents targeting vascular endothelial growth factor A, such as aflibercept;

agents targeting vascular endothelial growth factor receptor, such as fruquintinib or MP0250;

agents targeting VISTA, such as CA-170, or HMBD-002;

agents targeting WEE1, such as adavosertib (AZD-1775);

small molecule inhibitors targeting ABL1, such as imatinib, rebastinib, asciminib, or ponatinib (ICLUSIG®);

small molecule antagonists targeting adenosine receptor, such as CPI-444, AZD-4635, preladenant, etrumadenant (AB928), or PBF-509;

small molecule inhibitors targeting arachidonate 5-lipoxygenase, such as meclofenamate sodium or zileuton;

small molecule inhibitors targeting ATR serine/threonine kinase, such as BAY-937, ceralasertib (AZD6738), AZD6783, VX-803, or VX-970 (berzosertib);

small molecule inhibitors targeting AXL receptor tyrosine kinase, such as bemcentinib (BGB-324), SLC-0211, or gilteritinib (Axl/Flt3);

small molecule inhibitors targeting Bruton's tyrosine kinase (BTK), such as (S)-6-amino-9-(1-(but-2-ynoyl)pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;

small molecule inhibitors targeting neurotrophic receptor tyrosine kinase such as larotrectinib, entrectinib, or selitrectinib (LOXO-195);

small molecule inhibitors targeting ROS proto-oncogene 1, receptor tyrosine kinase, such as entrectinib, repotrectinib (TPX-0005), or lorlatinib;

small molecule inhibitors targeting SRC proto-oncogene, non-receptor tyrosine kinase, such as VAL-201, tirbanibulin (KX2-391), or ilginatinib maleate (NS-018);

small molecule inhibitors targeting B-cell lymphoma 2, such as navitoclax (ABT-263), venetoclax (ABT-199, RG-7601), or AT-101 (gossypol);

small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;

small molecule inhibitors targeting carbohydrate sulfotransferase 15, such as STNM-01;

small molecule inhibitors targeting carbonic anhydrase, such as polmacoxib, acetazolamide, or methazolamide;

small molecule inhibitors targeting catenin beta 1, such as CWP-291, or PRI-724;

small molecule antagonists targeting a C-C motif chemokine receptor, such as CCX-872, BMS-813160 (CCR2/CCR5) or MK-7690 (vicriviroc);

small molecule antagonists targeting a C-X-C motif chemokine receptor (e.g., CXCR4), blixafortide;

small molecule inhibitors targeting cereblon, such as avadomide (CC-122), CC-92480, CC-90009, or iberdomide;

small molecule inhibitors targeting checkpoint kinase 1, such as SRA737;

small molecule inhibitors targeting a complement component, such as Imprime PGG (Biothera Pharmaceuticals);

small molecule inhibitor targeting a C-X-C motif chemokine ligand (e.g., CXCL12), such as olaptesed pegol (NOX-A12);

small molecule inhibitors targeting cytochrome P450 family, such as ODM-209, LAE-201, seviteronel (VT-464), CFG920, abiraterone, or abiraterone acetate;

small molecule inhibitors targeting DEAD-box helicase 5, such as supinoxin (RX-5902);

small molecule inhibitors targeting DGKa, e.g., such as described in WO2021130638;

small molecule inhibitors targeting diablo IAP-binding mitochondrial protein, such as BI-891065;

small molecule inhibitors targeting dihydrofolate reductase, such as pralatrexate or pemetrexed disodium;

small molecule inhibitors targeting DNA dependent protein kinase, such as MSC2490484A (nedisertib), VX-984, AsiDNA (DT-01), LXS-196, or sotrastaurin;

small molecule inhibitors targeting MARCKS, such as BJO-11006;

small molecule inhibitors targeting RIPK1, such as GSK-3145094;

small molecule inhibitors targeting Rho associated coiled-coil containing protein kinase, such as AT13148 or KD025;

small molecule inhibitors targeting DNA topoisomerase, such as irinotecan, firtecan pegol, or amrubicin;

small molecule inhibitors targeting dopamine receptor D2, such as ONC-201;

small molecule inhibitors targeting DOT1 like histone lysine methyltransferase, such as pinometostat (EPZ-5676);

small molecule inhibitors targeting EZH2, such as tazemetostat, CPI-1205, or PF-06821497;

small molecule inhibitors targeting fatty acid synthase, such as TVB-2640 (Sagimet Biosciences);

small molecule inhibitors targeting fibroblast growth factor receptor 2 (FGFR2), such as bemarituzumab (FPA144);

small molecule inhibitors targeting focal adhesion kinase (FAK, PTK2), such as VS-4718, defactinib, or GSK2256098;

small molecule inhibitors targeting folate receptor 1, such as pralatrexate;

small molecule inhibitors targeting FOXM1, such as thiostrepton;

small molecule inhibitors targeting galectin 3, such as belapectin (GR-MD-02);

small molecule antagonists targeting glucocorticoid receptor, such as relacorilant (CORT-125134);

small molecule inhibitors targeting glutaminase include without limitation CB-839 (telaglenastat), or bis-2-(5-phenylacetamido-1,3,4-thiadiazol-2-yl)ethyl sulfide (BPTES);

small molecule inhibitors targeting GNRHR, such as elagolix, relugolix, or degarelix;

small molecule inhibitors targeting EPAS1, such as belzutifan (PT-2977 (Merck & Co.));

small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);

small molecule inhibitors targeting lysine demethylase 1A, such as CC-90011;

small molecule inhibitors targeting MAPK interacting serine/threonine kinase, such as tomivosertib (eFT-508);

small molecule inhibitors targeting notch receptor, such as AL-101 (BMS-906024);

small molecule inhibitors targeting polo like kinase 1 (PLK1), such as volasertib or onvansertib;

small molecule inhibitors targeting poly(ADP-ribose) polymerase (PARP), such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, CEP 9722, CEP-8983, E7016, 3-aminobenzamide, or CK-102;

small molecule inhibitors targeting polycomb protein EED, such as MAK683;

small molecule inhibitors targeting porcupine O-acyltransferase, such as WNT-974;

small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;

small molecule inhibitors targeting protein arginine N methyltransferase, such as MS203, PF-06939999, GSK3368715, or GSK3326595;

small molecule inhibitors targeting PTPN11, such as TNO155 (SHP-099), RMC-4550, JAB-3068, RMC-4630 (SAR442720), or compounds disclosed in WO2018172984 or WO2017211303;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S (DSP-7888);

small molecule agonists targeting adenosine receptor, such as namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cytochrome P450 family, such as mitotane;

small molecule agonists targeting DExD/H-box helicase 58, such as RGT-100;

small molecule agonists targeting GNRHR, such as leuprorelin acetate, leuprorelin acetate sustained release depot (ATRIGEL), triptorelin pamoate, or goserelin acetate;

small molecule agonists targeting GRB2, such as prexigebersen (BP1001);

small molecule agonists targeting NFE2L2, such as omaveloxolone (RTA-408);

small molecule agonists targeting NOD2, such as mifamurtide (liposomal);

small molecule agonists targeting RAR-related orphan receptor gamma, such as cintirorgon (LYC-55716);

small molecule agonists targeting retinoic acid receptor (RAR), such as tretinoin;

small molecule agonists targeting STING1, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;

small molecule agonists targeting thyroid hormone receptor beta, such as levothyroxine sodium;

small molecule agonists targeting tumor necrosis factor, such as tasonermin;

antisense agents targeting baculoviral IAP repeat containing 5, such as EZN-3042;

antisense agents targeting GRB2, such as prexigebersen;

antisense agents targeting heat shock protein 27, such as apatorsen;

antisense agents targeting STAT3, such as danvatirsen (IONIS-STAT3-2.5Rx);

gene therapies targeting a C-C motif chemokine receptor, such as SB-728-T;

gene therapies targeting an interleukin, such as EGENE-001, tavokinogene telseplasmid, nogapendekin alfa (ALT-803), NKTR-255, NIZ-985 (hetIL-15), SAR441000, or MDNA-55;

antibodies targeting claudin 18, such as claudiximab;

antibodies targeting clusterin, such as AB-16B5;

antibodies targeting a complement component, such as ravulizumab (ALXN-1210);

antibodies targeting a C-X-C motif chemokine ligand, such as BMS-986253 (HuMax-Inflam);

antibodies targeting delta like canonical Notch ligand 4 (DLL4), such as demcizumab, navicixizumab (DLL4/VEGF);

antibodies targeting EPH receptor A3, such as fibatuzumab (KB-004);

antibodies targeting epithelial cell adhesion molecule, such as oportuzumab monatox (VB4-845);

antibodies targeting fibroblast growth factor, such as GAL-F2, B-701 (vofatamab);

antibodies targeting hepatocyte growth factor, such as MP-0250;

antibodies targeting an interleukin, such as canakinumab (ACZ885), gevokizumab (VPM087), CJM-112, guselkumab, talacotuzumab (JNJ-56022473), siltuximab, or tocilizumab;

antibodies targeting LRRC15, such as ABBV-085 or cusatuzumab (ARGX-110);

antibodies targeting mesothelin, such as BMS-986148, SEL-403, or anti-MSLN-MMAE;

antibodies targeting myostatin, such as landogrozumab;

antibodies targeting notch receptor, such as tarextumab;

antibodies targeting TGFB1 (TGFb1), such as SAR439459, ABBV-151, NIS793, SRK-181, XOMA089, or compounds disclosed in WO2019103203;

vaccines targeting fms related receptor tyrosine kinase, such as HLA-A2402/HLA-A0201 restricted epitope peptide vaccine;

vaccines targeting heat shock protein 27, such as PSV-AML (PhosphoSynVax);

vaccines targeting PD-L1, such as IO-120+IO-103 (PD-L1/PD-L2 vaccines) or IO-103;

vaccines targeting tumor protein p53, such as MVA-p53;

vaccines targeting WT1, such as WT-1 analog peptide vaccine (WT1-CTL);

cell therapies targeting baculoviral IAP repeat containing 5, such as tumor lysate/MUC1/survivin PepTivator-loaded dendritic cell vaccine;

cell therapies targeting carbonic anhydrase, such as DC-Ad-GMCAIX;

cell therapies targeting C-C motif chemokine receptor, such as CCR5-SBC-728-HSPC;

cell therapies targeting folate hydrolase 1, such as CIK-CAR.PSMA or CART-PSMA-TGFβRDN;

cell therapies targeting GSTP1, such as CPG3-CAR (GLYCAR);

cell therapies targeting HLA-A, such as FH-MCVA2TCR or NeoTCR-P1;

cell therapies targeting an interleukin, such as CST-101;

cell therapies targeting KRAS, such as anti-KRAS G12D mTCR PBL;

cell therapies targeting MET, such as anti-cMet RNA CAR T;

cell therapies targeting MUC16, such as JCAR-020;

cell therapies targeting PD-1, such as PD-1 knockout T cell therapy (esophageal cancer/NSCLC);

cell therapies targeting PRAME, such as BPX-701;

cell therapies targeting transforming protein E7, such as KITE-439;

cell therapies targeting WT1, such as WT1-CTL, ASP-7517, or JTCR-016.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCI-779), thalidomide, therapeutic allogeneic lymphocytes, thiotepa, tipifarnib, vincristine, vincristine sulfate, vinorelbine ditartrate, SAHA (sub-eranilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma (DLBCL) Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE. In some embodiments therapeutic agents used to treat DLBCL include rituximab (Rituxan®), cyclophosphamide, doxorubicin hydrochloride (hydroxydaunorubicin), vincristine sulfate (Oncovin®), prednisone, bendamustine, ifosfamide, carboplatin, etoposide, ibrutinib, polatuzumab vedotin piiq, bendamustine, copanlisib, lenalidomide (Revlimid®), dexamethasone, cytarabine, cisplatin, Yescarta®, Kymriah®, Polivy® (polatuzumab vedotin), BR (bendamustine (Treanda®), gemcitabine, oxiplatin, oxaliplatin, tafasitamab, polatuzumab, cyclophosphamide, or combinations thereof. In some embodiments therapeutic agents used to treat DLBCL include R-CHOP (rituximab+cyclophosphamide+doxorubicin hydrochloride (hydroxydaunorubicin)+vincristine sulfate (Oncovin®), +prednisone), rituximab+bendamustine, R-ICE (Rituximab+Ifosfamide+Carboplatin+Etoposide), rituximab+lenalomide, R-DHAP (rituximab+dexamethasone+high-dose cytarabine (Ara C)+cisplatin), Polivy® (polatuzumab vedotin)+BR (bendamustine (Treanda®) and rituximab (Rituxan®)), R-GemOx (Gemcitabine+oxaliplatin+rituximab), Tafa-Len (tafasitamab+lenalidomide), Tafasitamab+Revlimid®, polatuzumab+bendamustine, Gemcitabine+oxaliplatin, R-EPOCH (rituximab+etoposide phosphate+prednisone+vincristine sulfate (Oncovin®)+cyclophosphamide+doxorubicin hydrochloride (hydroxydaunorubicin)), or CHOP (cyclophosphamide+doxorubicin hydrochloride (hydroxydaunorubicin)+vincristine sulfate (Oncovin®)+prednisone). In some embodiments therapeutic agents used to treat DLBCL include tafasitamab, glofitamab, epcoritamab, Lonca-T (loncastuximab tesirine), Debio-1562, polatuzumab, Yescarta, JCAR017, ADCT-402, brentuximab vedotin, MT-3724, odronextamab, Auto-03, Allo-501A, or TAK-007.

Chronic Lymphocytic Leukemia Combination Therapy

Therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemo-immunotherapy, including the following common combination regimens: CVP, R-CVP, ICE, R-ICE, FCR, and FR.

High Risk Myelodysplastic Syndrome (HR MDS) Combination Therapy

Therapeutic agents used to treat HR MDS include azacitidine (Vidaza®), decitabine (Dacogen®), lenalidomide (Revlimid®), cytarabine, idarubicin, daunorubicin, and combinations thereof.

In some embodiments combinations include cytarabine+daunorubicin and cytarabine+idarubicin. In some embodiments therapeutic agents used to treat HR MDS include pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments therapeutic agents used to treat LR MDS include roxadustat, luspatercept, imetelstat, LB-100, or rigosertib.

Acute Myeloid Leukemia (AML) Combination Therapy

Therapeutic agents used to treat AML include cytarabine, idarubicin, daunorubicin, midostaurin (Rydapt®), venetoclax, azacitidine, ivasidenib, gilteritinib, enasidenib, low-dose cytarabine (LoDAC), mitoxantrone, fludarabine, granulocyte-colony stimulating factor, idarubicin, gilteritinib (Xospata®), enasidenib (Idhifa®), ivosidenib (Tibsovo®), decitabine (Dacogen®), mitoxantrone, etoposide, Gemtuzumab ozogamicin (Mylotarg®), glasdegib (Daurismo®), and combinations thereof. In some embodiments therapeutic agents used to treat AML include FLAG-Ida (fludarabine, cytarabine (Ara-C), granulocyte-colony stimulating factor (G-CSF) and idarubicin), cytarabine+idarubicin, cytarabine+daunorubicin+midostaurin, venetoclax+azacitidine, cytarabine+daunorubicin, or MEC (mitoxantrone, etoposide, and cytarabine). In some embodiments, therapeutic agents used to treat AML include pevonedistat, venetoclax, sabatolimab, eprenetapopt, or lemzoparlimab.

Multiple Myeloma (MM) Combination Therapy

Therapeutic agents used to treat MM include lenalidomide, bortezomib, dexamethasone, daratumumab (Darzalex®), pomalidomide, Cyclophosphamide, Carfilzomib (Kyprolis®), Elotuzumab (Empliciti), and combinations thereof. In some embodiments therapeutic agents used to treat MM include RVS (lenalidomide+bortezomib+dexamethasone), RevDex (lenalidomide plus dexamethasone), CYBORD (Cyclophosphamide+Bortezomib+Dexamethasone), Vel/Dex (bortezomib plus dexamethasone), or Pom-Dex (Pomalidomide+low-dose dexamethasone). In some embodiments therapeutic agents used to treat MM include JCARH125, TAK-573, belantamab-m, ide-cel (CAR-T).

Breast Cancer Combination Therapy

Therapeutic agents used to treat breast cancer include albumin-bound paclitaxel, anastrozole, atezolizumab, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, letrozole, methotrexate, mitoxantrone, paclitaxel, pegylated liposomal doxorubicin, pertuzumab, tamoxifen, toremifene, trastuzumab, vinorelbine, and any combinations thereof. In some embodiments therapeutic agents used to treat breast cancer (e.g., HR+/−/HER2+/−) include trastuzumab (Herceptin®), pertuzumab (Perjeta®), docetaxel, carboplatin, palbociclib (Ibrance®), letrozole, trastuzumab emtansine (Kadcyla©), fulvestrant (Faslodex®), olaparib (Lynparza®), eribulin, tucatinib, capecitabine, lapatinib, everolimus (Afinitor®), exemestane, eribulin mesylate (Halaven®), and combinations thereof. In some embodiments therapeutic agents used to treat breast cancer include trastuzumab+pertuzumab+docetaxel, trastuzumab+pertuzumab+docetaxel+carboplatin, palbociclib+letrozole, tucatinib+capecitabine, lapatinib+capecitabine, palbociclib+fulvestrant, or everolimus+exemestane. In some embodiments therapeutic agents used to treat breast cancer include trastuzumab deruxtecan (Enhertu®), datopotamab deruxtecan (DS-1062), enfortumab vedotin (Padcev®), balixafortide, elacestrant, or a combination thereof. In some embodiments therapeutic agents used to treat breast cancer include balixafortide+eribulin.

Triple Negative Breast Cancer (TNBC) Combination Therapy

Therapeutic agents used to treat TNBC include atezolizumab, cyclophosphamide, docetaxel, doxorubicin, epirubicin, fluorouracil, paclitaxel, and combinations thereof. In some embodiments therapeutic agents used to treat TNBC include olaparib (Lynparza®), atezolizumab (Tecentriq®), paclitaxel (Abraxane®), eribulin, bevacizumab (Avastin®), carboplatin, gemcitabine, eribulin mesylate (Halaven®), sacituzumab govitecan (Trodelvy®), pembrolizumab (Keytruda®), cisplatin, doxorubicin, epirubicin, or a combination thereof. In some embodiments therapeutic agents to treat TNBC include atezolizumab+paclitaxel, bevacizumab+paclitaxel, carboplatin+paclitaxel, carboplatin+gemcitabine, or paclitaxel+gemcitabine. In some embodiments therapeutic agents used to treat TNBC include eryaspase, capivasertib, alpelisib, rucaparib+nivolumab, atezolumab+paclitaxel+gemcitabine+capecitabine+carboplatin, ipatasertib+paclitaxel, ladiratuzumab vedotin+pembrolimab, durvalumab+DS-8201a, trilaciclib+gemcitabine+carboplatin. In some embodiments therapeutic agents used to treat TNBC include trastuzumab deruxtecan (Enhertu®), datopotamab deruxtecan (DS-1062), enfortumab vedotin (Padcev®), balixafortide, adagloxad simolenin, nelipepimut-s (NeuVax®), nivolumab (Opdivo®), rucaparib, toripalimab (Tuoyi®), camrelizumab, capivasertib, durvalumab (Imfinzi®), and combinations thereof. In some embodiments therapeutic agents use to treat TNBC include nivolumab+rucaparib, bevacizumab (Avastin®)+chemotherapy, toripalimab+paclitaxel, toripalimab+albumin-bound paclitaxel, camrelizumab+chemotherapy, pembrolizumab+chemotherapy, balixafortide+eribulin, durvalumab+trastuzumab deruxtecan, durvalumab+paclitaxel, or capivasertib+paclitaxel.

Bladder Cancer Combination Therapy

Therapeutic agents used to treat bladder cancer include datopotamab deruxtecan (DS-1062), trastuzumab deruxtecan (Enhertu®), erdafitinib, eganelisib, lenvatinib, bempegaldesleukin (NKTR-214), or a combination thereof. In some embodiments therapeutic agents used to treat bladder cancer include eganelisib+nivolumab, pembrolizumab (Keytruda®)+enfortumab vedotin (Padcev©), nivolumab+ipilimumab, duravalumab+tremelimumab, lenvatinib+pembrolizumab, enfortumab vedotin (Padcev©)+pembrolizumab, and bempegaldesleukin+nivolumab.

Colorectal Cancer (CRC) Combination Therapy

Therapeutic agents used to treat CRC include bevacizumab, capecitabine, cetuximab, fluorouracil, irinotecan, leucovorin, oxaliplatin, panitumumab, ziv-aflibercept, and any combinations thereof. In some embodiments therapeutic agents used to treat CRC include bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, or a combination thereof. In some embodiments therapeutic agents used to treat CRC include bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, bevacizumab+XELOX, and bevacizumab+FOLFOXIRI. In some embodiments therapeutic agents used to treat CRC include binimetinib+encorafenib+cetuximab, trametinib+dabrafenib+panitumumab, trastuzumab+pertuzumab, napabucasin+FOLFIRI+bevacizumab, nivolumab+ipilimumab.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof. In some embodiments therapeutic agents used to treat gastroesophageal junction cancer (GEJ) include herceptin, cisplatin, 5-FU, ramicurimab, or paclitaxel. In some embodiments therapeutic agents used to treat GEJ cancer include ALX-148, AO-176, or IBI-188.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Therapeutic agents used to treat head and neck squamous cell carcinoma (HNSCC) include pembrolizumab, carboplatin, 5-FU, docetaxel, cetuximab (Erbitux®), cisplatin, nivolumab (Opdivo®), and combinations thereof. In some embodiments therapeutic agents used to treat HNSCC include pembrolizumab+carboplatin+5-FU, cetuximab+cisplatin+5-FU, cetuximab+carboplatin+5-FU, cisplatin+5-FU, and carboplatin+5-FU. In some embodiments therapeutic agents used to treat HNSCC include durvalumab, durvalumab+tremelimumab, nivolumab+ipilimumab, rovaluecel, pembrolizumab, pembrolizumab+epacadostat, GSK3359609+pembrolizumab, lenvatinib+pembrolizumab, retifanlimab, retifanlimab+enobituzumab, ADU-S100+pembrolizumab, epacadostat+nivolumab+ipilimumab/lirilumab.

Non-Small Cell Lung Cancer Combination Therapy

Therapeutic agents used to treat non-small cell lung cancer (NSCLC) include afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof. In some embodiments therapeutic agents used to treat NSCLC include alectinib (Alecensa®), dabrafenib (Tafinlar®), trametinib (Mekinist®), osimertinib (Tagrisso®), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), and combinations thereof. In some embodiments therapeutic agents used to treat NSCLC include dabrafenib+trametinib, pembrolizumab+carboplatin+pemetrexed, pembrolizumab+carboplatin+nab-paclitaxel, ramucirumab+docetaxel, bevacizumab+carboplatin+pemetrexed, pembrolizumab+pemetrexed+carboplatin, cisplatin+pemetrexed, bevacizumab+carboplatin+nab-paclitaxel, cisplatin+gemcitabine, nivolumab+docetaxel, carboplatin+pemetrexed, carboplatin+nab-paclitaxel, or pemetrexed+cisplatin+carboplatin. In some embodiments therapeutic agents used to NSCLC include datopotamab deruxtecan (DS-1062), trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, or a combination thereof. In some embodiments therapeutic agents used to treat NSCLC include datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

Small Cell Lung Cancer Combination Therapy

Therapeutic agents used to treat small cell lung cancer (SCLC) include atezolizumab, bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof. In some embodiments therapeutic agents used to treat SCLC include atezolizumab, carboplatin, cisplatin, etoposide, paclitaxel, topotecan, nivolumab, durvalumab, trilaciclib, or combinations thereof. In some embodiments therapeutic agents used to treat SCLC include atezolizumab+carboplatin+etoposide, atezolizumab+carboplatin, atezolizumab+etoposide, or carboplatin+paclitaxel.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, pazopanib, pemetrexed, tamoxifen, topotecan, vinorelbine, and any combinations thereof.

Pancreatic Cancer Combination Therapies

Therapeutic agents used to treat pancreatic cancer include 5-FU, leucovorin, oxaliplatin, irinotecan, gemcitabine, nab-paclitaxel (Abraxane®), FOLFIRINOX, and combinations thereof. In some embodiments therapeutic agents used to treat pancreatic cancer include 5-FU+leucovorin+oxaliplatin+irinotecan, 5-FU+nanoliposomal irinotecan, leucovorin+nanoliposomal irinotecan, and gemcitabine+nab-paclitaxel.

Prostate Cancer Combination Therapies

Therapeutic agents used to treat prostate cancer include enzalutamide (Xtandi®), leuprolide, trifluridine, tipiracil (Lonsurf), cabazitaxel, prednisone, abiraterone (Zytiga®), docetaxel, mitoxantrone, bicalutamide, LHRH, flutamide, ADT, sabizabulin (Veru-111), and combinations thereof. In some embodiments therapeutic agents used to treat prostate cancer include enzalutamide+leuprolide, trifluridine+tipiracil (Lonsurf), cabazitaxel+prednisone, abiraterone+prednisone, docetaxel+prednisone, mitoxantrone+prednisone, bicalutamide+LHRH, flutamide+LHRH, leuprolide+flutamide, and abiraterone+prednisone+ADT.

Additional Exemplified Combination Therapies

In some embodiments the Compound provided herein is administered with one or more therapeutic agents selected from a PI3K inhibitor, a Trop-2 binding agent, CD47 antagonist, a SIRPα antagonist, a FLT3R agonist, a PD-1 antagonist, a PD-L1 antagonist, an MCL1 inhibitor, a CCR8 binding agent, an HPK1 antagonist, a DGKa inhibitor, a CISH inhibitor, a PARP-7 inhibitor, a Cbl-b inhibitor, a KRAS inhibitor (e.g., a KRAS G12C or G12D inhibitor), a KRAS degrader, a beta-catenin degrader, a helios degrader, a CD73 inhibitor, an adenosine receptor antagonist, a TIGIT antagonist, a TREM1 binding agent, a TREM2 binding agent, a CD137 agonist, a GITR binding agent, an OX40 binding agent, and a CAR-T cell therapy.

In some embodiments the Compound provided herein is administered with one or more therapeutic agents selected from a PI3Kd inhibitor (e.g., idealisib), an anti-Trop-2 antibody drug conjugate (e.g., sacituzumab govitecan, datopotamab deruxtecan (DS-1062)), an anti-CD47 antibody or a CD47-blocking agent (e.g., magrolimab, DSP-107, AO-176, ALX-148, letaplimab (IBI-188), lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab, avelumab), a small molecule MCL1 inhibitor (e.g., GS-9716), a small molecule HPK1 inhibitor (e.g., GS-6451), a HPK1 degrader (PROTAC; e.g., ARV-766), a small molecule DGKa inhibitor, a small molecule CD73 inhibitor (e.g., quemliclustat (AB680)), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a CD137 agonist (e.g., AGEN-2373), a GITR/OX40 binding agent (e.g., AGEN-1223) and a CAR-T cell therapy (e.g., axicabtagene ciloleucel, brexucabtagene autoleucel, tisagenlecleucel).

In some embodiments the Compound provided herein is administered with one or more therapeutic agents selected from idealisib, sacituzumab govitecan, magrolimab, GS-0189, GS-3583, zimberelimab, GS-4224, GS-9716, GS-6451, quemliclustat (AB680), etrumadenant (AB928), domvanalimab, AB308, PY159, PY314, AGEN-1223, AGEN-2373, axicabtagene ciloleucel and brexucabtagene autoleucel.

VI. Examples

Abbreviations

Certain abbreviations and acronyms are used in describing the experimental details. Although most of these would be understood by one skilled in the art, Table 1 contains a list of many of these abbreviations and acronyms.

TABLE 1

List of abbreviations and acronyms

| Abbreviation | Definition |
|---|---|
| Ac | acetate |
| Ar | argon |
| ACN | acetonitrile |
| cat | catalyst |
| DCM | dichloromethane |
| DIPEA | N,N-diisopropylethylamine |
| DMSO | dimethylsulfoxide |
| DMF | dimethylformamide |
| ES/MS | electrospray mass spectrometry |
| Et | ethyl |
| EtOAc | ethyl acetate |
| HPLC | high performance liquid chromatography |
| LC | liquid chromatography |
| Me | methyl |
| MeCN | acetonitrile |
| m/z | mass to charge ratio |
| NMP | N-methyl-2-pyrrolidone |
| NMR | Nuclear Magnetic Resonance |
| Ph | phenyl |
| Pd(dppf)Cl$_2$ or PdCl$_2$(dppf) | [1,1'-Bis(diphenylphosphino)ferrocene]dichloropalladium(II) |
| Pr | propyl |
| RP | reverse phase |
| TFA | trifluoroacetic acid |
| THF | tetrahydrofuran |
| TBHP | tert-butyl hydroperoxide |
| δ | parts per million referenced to residual non-deuterated solvent peak |

TABLE 2

Compounds

| Structure | Example Number | IUPAC Name |
|---|---|---|
| 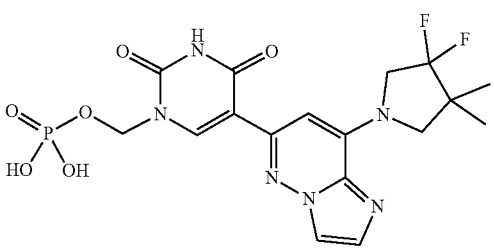 [SMILES: CC1(C)CN(c2cc(-c3cn(COP(=O)(O)O)c(=O)[nH]c3=O)nn3ccnc23)CC1(F)F] | Ex. 1 | (5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl dihydrogen phosphate |
| 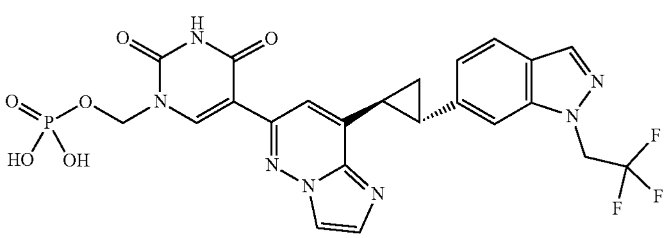 [SMILES: O=c1[nH]c(=O)n(COP(=O)(O)O)cc1-c1cc([C@H]2C[C@@H]2c2ccc3cnn(CC(F)(F)F)c3c2)c2nccn2n1] | Ex. 2 | (2,4-dioxo-5-(8-((1S,2S)-2-(1-(2,2,2-trifluoroethyl)-1H-indazol-6-yl)cyclopropyl)imidazo[1,2-b]pyridazin-6-yl)-3,4-dihydropyrimidin-1(2H)-yl)methyl dihydrogen phosphate |
| 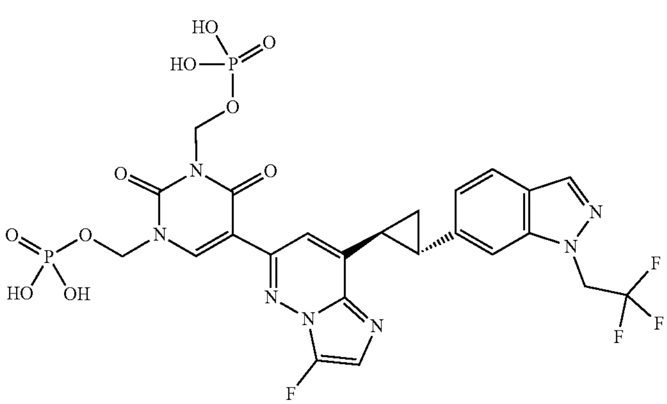 [SMILES: O=c1c(-c2cc([C@H]3C[C@@H]3c3ccc4cnn(CC(F)(F)F)c4c3)c3ncc(F)n3n2)cn(COP(=O)(O)O)c(=O)n1COP(=O)(O)O] | Ex. 3 | (5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxopyrimidine-1,3(2H,4H)-diyl)bis(methylene) bis(dihydrogen phosphate) |

TABLE 2-continued

Compounds

| Structure | Example Number | IUPAC Name |
|---|---|---|
| 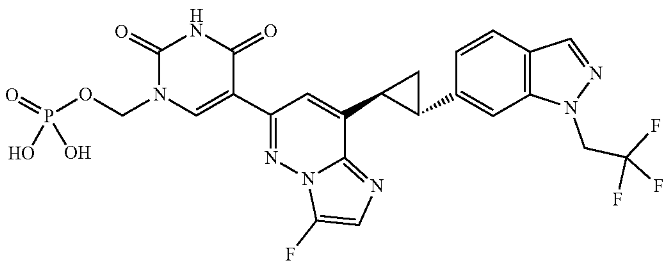 [SMILES: O=c1[nH]c(=O)n(COP(=O)(O)O)cc1-c1cc([C@H]2C[C@@H]2c2ccc3cnn(CC(F)(F)F)c3c2)c2ncc(F)n2n1] | Ex. 4 | (5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl dihydrogen phosphate |
| 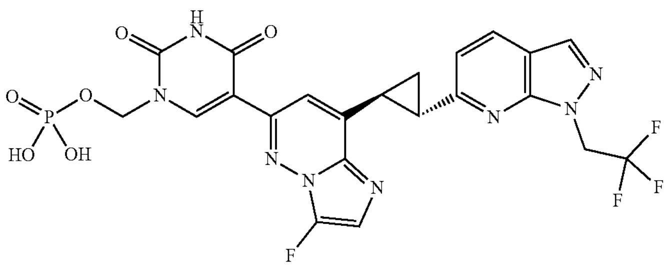 [SMILES: O=c1[nH]c(=O)n(COP(=O)(O)O)cc1-c1cc([C@H]2C[C@@H]2c2ccc3cnn(CC(F)(F)F)c3n2)c2ncc(F)n2n1] | Ex. 5 | (5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)-2,4-dioxo-3,4-dihydropyrimidin-1(2H)-yl)methyl dihydrogen phosphate |
| 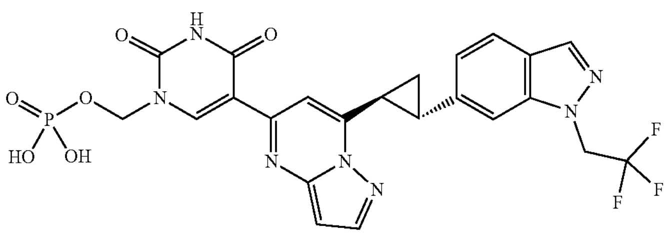 [SMILES: O=c1[nH]c(=O)n(COP(=O)(O)O)cc1-c1cc([C@H]2C[C@@H]2c2ccc3cnn(CC(F)(F)F)c3c2)n2nccc2n1] | Ex. 6 | (2,4-dioxo-5-(7-((1S,2S)-2-(1-(2,2,2-trifluoroethyl)-1H-indazol-6-yl)cyclopropyl)pyrazolo[1,5-a]pyrimidin-5-yl)-3,4-dihydropyrimidin-1(2H)-yl)methyl dihydrogen phosphate |
| 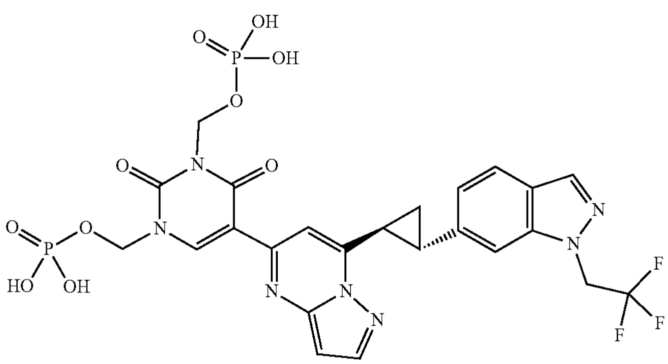 [SMILES: O=c1c(-c2cc([C@H]3C[C@@H]3c3ccc4cnn(CC(F)(F)F)c4c3)n3nccc3n2)cn(COP(=O)(O)O)c(=O)n1COP(=O)(O)O] | Ex. 7 | (2,4-dioxo-5-(7-((1S,2S)-2-(1-(2,2,2-trifluoroethyl)-1H-indazol-6-yl)cyclopropyl)pyrazolo[1,5-a]pyrimidin-5-yl)pyrimidine-1,3(2H,4H)-diyl)bis(methylene) bis(dihydrogen phosphate) |
| 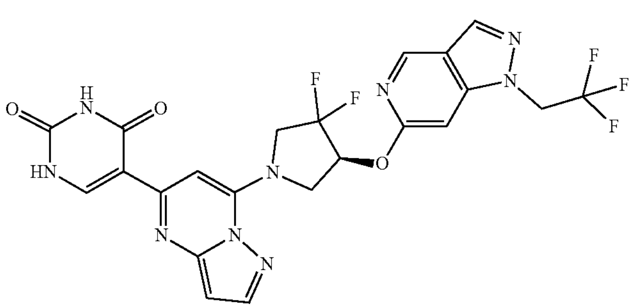 [SMILES: O=c1[nH]cc(-c2cc(N3C[C@H](Oc4cc5c(cn4)cnn5CC(F)(F)F)C(F)(F)C3)n3nccc3n2)c(=O)[nH]1] | Ex. 8 | (S)-5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)pyrimidine-2,4(1H,3H)-dione |

TABLE 2-continued

Compounds

| Structure | Example Number | IUPAC Name |
|---|---|---|
| 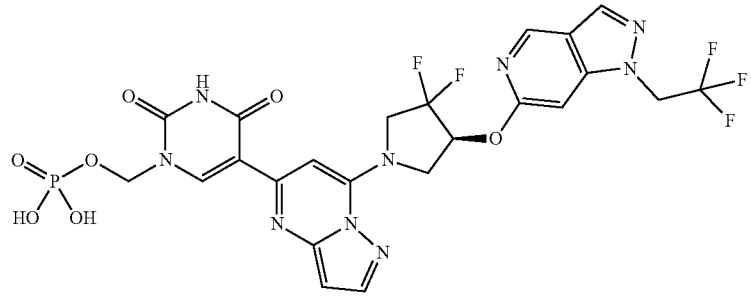 [SMILES: O=c1[nH]c(=O)n(COP(=O)(O)O)cc1-c1cc(N2C[C@H](Oc3cc4c(cn3)cnn4CC(F)(F)F)C(F)(F)C2)n2nccc2n1] | Ex 9 | (S)-(5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl dihydrogen phosphate |
| 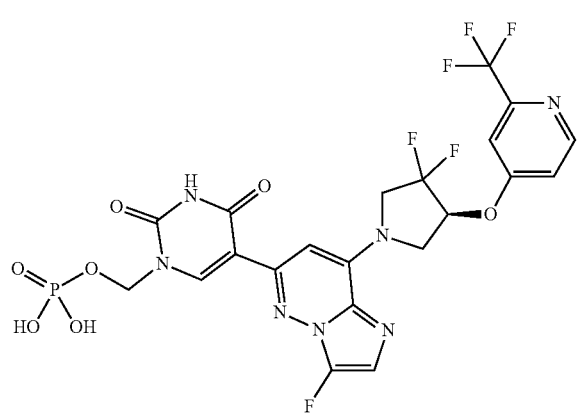 [SMILES: O=c1[nH]c(=O)n(COP(=O)(O)O)cc1-c1cc(N2C[C@H](Oc3ccnc(C(F)(F)F)c3)C(F)(F)C2)c2ncc(F)n2n1] | Ex 10 | (S)-(5-(8-(3,3-difluoro-4-((2-(trifluoromethyl)pyridin-4-yl)oxy)pyrrolidin-1-yl)-3-fluoroimidazo[1,2-b]pyridazin-6-yl)-2,4-dioxo-3,4-dihydropyrimidin-1(2H)-yl)methyl dihydrogen phosphate |
| 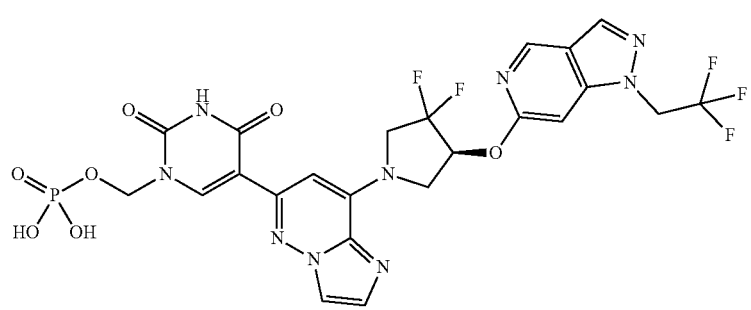 [SMILES: O=c1[nH]c(=O)n(COP(=O)(O)O)cc1-c1cc(N2C[C@H](Oc3cc4c(cn3)cnn4CC(F)(F)F)C(F)(F)C2)c2nccn2n1] | Ex. 11 | (S)-(5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)-2,4-dioxo-3,4-dihydropyrimidin-1(2H)-yl)methyl dihydrogen phosphate |

General Procedure 1

Preparation of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl) methyl) phosphate

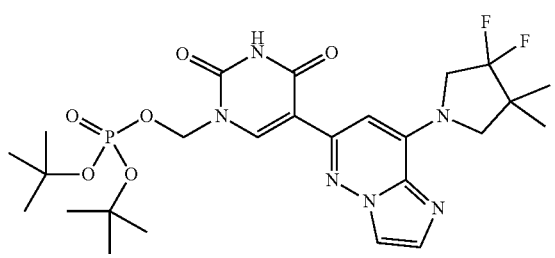 [SMILES: CC(C)(C)OP(=O)(OCn1cc(-c2cc(N3CC(C)(C)C(F)(F)C3)c3nccn3n2)c(=O)[nH]c1=O)OC(C)(C)C]

To a solution of 5-(8-(3,3-difluoro-4,4-dimethylpyrrolidin-1-yl)imidazo[1,2-b]pyridazin-6-yl)pyrimidine-2,4(1H,3H)-dione (500 mg, 1.38 mmol, 1 equiv) and triethylamine (0.67 mL, 4.83 mmol, 3.5 equiv) in DMF (16 mL) was added di-tert-butyl (chloromethyl) phosphate (1.07 g, 4.14 mmol, 3 equiv). The reaction mixture was heated to 60° C. and stirred for 16 h. Another aliquot of di-tert-butyl (chloromethyl) phosphate (1.07 g, 4.14 mmol, 3 equiv) and triethylamine (0.67 mL, 4.83 mmol, 3.5 equiv) were added and the reaction stirred for another 16 hours. The reaction mixture was subsequently diluted with EtOAc/water, extracted twice with EtOAc. The combined organic layers were dried over MgSO4, filtered and concentrated in vacuo. The crude product was purified by silica chromatography (100% EtOAc) to provide di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate

Example 1

Preparation of (5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl dihydrogen phosphate

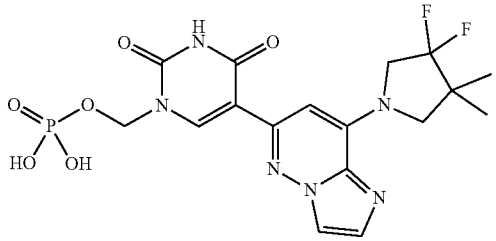 [SMILES: CC1(C)CN(c2cc(-c3cn(COP(=O)(O)O)c(=O)[nH]c3=O)nn3ccnc23)CC1(F)F]

To a solution of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate (671 mg, 1.15 mmol, 1 equiv) in DCM (15 mL) was added TFA (5 mL). The reaction mixture was stirred at room temperature for 15 min before being concentrated in vacuo and purified by HPLC (10-80% MeCN/water with TFA). LC-MS m/z: 473.1 (M+1). 1H NMR (400 MHz, DMSO-d6) δ 11.79 (s, 1H), 8.25 (s, 1H), 8.08 (d, J=1.2 Hz, 1H), 7.59 (d, J=1.2 Hz, 1H), 6.54 (s, 1H), 5.53 (d, J=10.7 Hz, 2H), 4.41 (s, 2H), 3.86 (s, 2H), 1.21 (s, 6H). 19F NMR (376 MHz, DMSO-d6) δ −115.33 (m, 2F). 31P NMR (162 MHz, DMSO-d6) δ −2.24 (t, J=10.6 Hz, 1P).

The following compounds were prepared in an analogous manner to (5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl dihydrogen phosphate using the modifications listed below:

Example 2 di-tert-butyl ((2,4-dioxo-5-(8-((1S,2S)-2-(1-(2,2,2-trifluoroethyl)-1H-indazol-6-yl)cyclopropyl)imidazo[1,2-b]pyridazin-6-yl)-3,4-dihydropyrimidin-1(2H)-yl)methyl) phosphate was prepared using 5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride in place of 5-(8-(3,3-difluoro-4,4-dimethylpyrrolidin-1-yl)imidazo[1,2-b]pyridazin-6-yl)pyrimidine-2,4(1H,3H)-dione

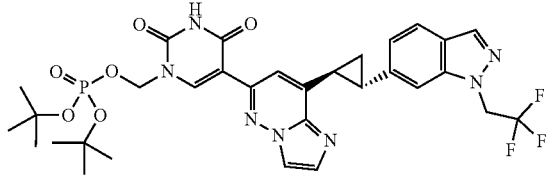 [SMILES: CC(C)(C)OP(=O)(OCn1cc(-c2cc([C@H]3C[C@@H]3c3ccc4cnn(CC(F)(F)F)c4c3)c3nccn3n2)c(=O)[nH]c1=O)OC(C)(C)C]

5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione was prepared using di-tert-butyl ((2,4-dioxo-5-(8-((1S,2S)-2-(1-(2,2,2-trifluoroethyl)-1H-indazol-6-yl)cyclopropyl)imidazo[1,2-b]pyridazin-6-yl)-3,4-dihydropyrimidin-1(2H)-yl)methyl) phosphate in place of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate

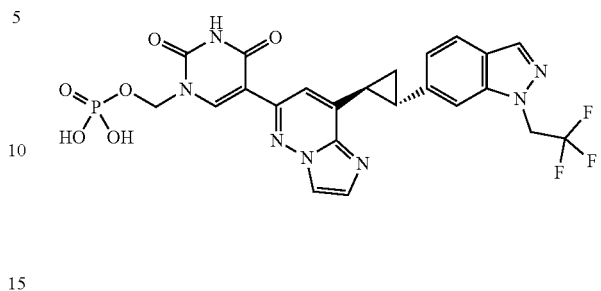

LC-MS m/z: 578.1 (M+1). 1H NMR (400 MHz, DMSO-d6) δ 11.90 (s, 1H), 8.33 (s, 1H), 8.28 (d, J=1.3 Hz, 1H), 8.16 (d, J=0.9 Hz, 1H), 7.77-7.66 (m, 3H), 7.49 (s, 1H), 7.13 (dd, J=8.6, 1.2 Hz, 1H), 5.56 (d, J=10.8 Hz, 2H), 5.41 (q, J=9.1 Hz, 2H), 3.09-3.00 (m, 1H), 2.81 (dt, J=9.6, 5.2 Hz, 1H), 2.19 (dt, J=9.4, 5.1 Hz, 1H), 1.89 (dt, J=9.4, 5.3 Hz, 1H). 19F NMR (376 MHz, DMSO-d6) δ −70.08 (t, J=9.1 Hz, 3F). 31P NMR (162 MHz, DMSO-d6) δ −2.22 (t, J=11.0 Hz, 1P).

Example 3 tetra-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxopyrimidine-1,3(2H,4H)-diyl)bis(methylene)) bis(phosphate) was prepared using 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione in place of 5-(8-(3,3-difluoro-4,4-dimethylpyrrolidin-1-yl)imidazo[1,2-b]pyridazin-6-yl)pyrimidine-2,4(1H,3H)-dione

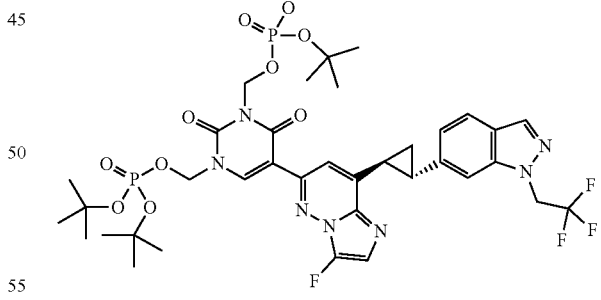

(5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxopyrimidine-1,3(2H,4H)-diyl)bis(methylene) bis(dihydrogen phosphate) was prepared using tetra-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxopyrimidine-1,3(2H,4H)-diyl)bis(methylene)) bis(phosphate) in place of di-tert-butyl ((5-(8-(3,3-difluoro-4,4-dimethylpyrrolidin-1-yl)imidazo[1,2-b]pyridazin-6-yl)-2,4-dioxo-3,4-dihydropyrimidin-1(2H)-yl)methyl) phosphate

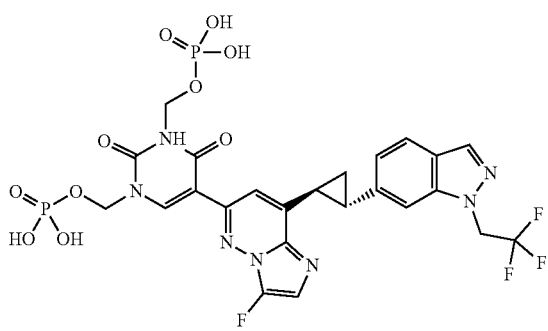 [SMILES: O=c1c(-c2cc([C@H]3C[C@@H]3c3ccc4cnn(CC(F)(F)F)c4c3)c3ncc(F)n3n2)cn(COP(=O)(O)O)c(=O)n1COP(=O)(O)O]

LC-MS m/z: 706.1 (M+1). 1H NMR (400 MHz, DMSO-d6) δ 8.45 (s, 1H), 8.15 (d, J=0.8 Hz, 1H), 7.73 (d, J=8.2 Hz, 2H), 7.60 (d, J=7.1 Hz, 1H), 7.43 (s, 1H), 7.13 (dd, J=8.4, 1.4 Hz, 1H), 5.69 (d, J=6.5 Hz, 2H), 5.64 (d, J=10.8 Hz, 2H), 5.41 (q, J=9.2 Hz, 2H), 3.02 (ddd, J=8.9, 6.3, 4.3 Hz, 1H), 2.83 (ddd, J=8.8, 5.9, 4.3 Hz, 1H), 2.21-2.09 (m, 1H), 1.91 (dt, J=8.7, 5.5 Hz, 1H). 19F NMR (376 MHz, DMSO-d6) δ −70.08 (t, J=9.1 Hz, 3F), −155.02 (d, J=7.2 Hz, 1F). 31P NMR (162 MHz, DMSO-d6) δ −2.18 (t, J=11.0 Hz, 1P), −3.44 (t, J=6.5 Hz, 1P).

General Procedure 2

Preparation of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate

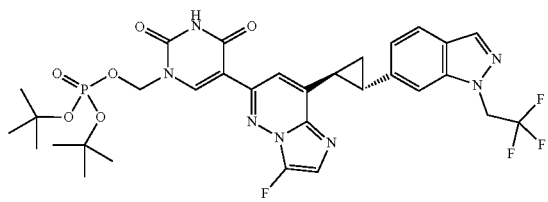 [SMILES: CC(C)(C)OP(=O)(OCn1cc(-c2cc([C@H]3C[C@@H]3c3ccc4cnn(CC(F)(F)F)c4c3)c3ncc(F)n3n2)c(=O)[nH]c1=O)OC(C)(C)C]

To a solution of 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride (100 mg, 0.192 mmol, 1 equiv) in DMAc (1 mL) was added KHCO₃ (48 mg, 0.479 mmol, 2.5 equiv) and di-tert-butyl (chloromethyl) phosphate (59.5 mg, 0.23 mmol, 1.2 equiv). The reaction mixture was heated to 60° C. and stirred for 16 h. The reaction mixture was subsequently diluted with EtOAc/water, extracted twice with EtOAc. The combined organic layers were dried over MgSO4, filtered and concentrated in vacuo. The crude product was purified by silica chromatography (100% EtOAc) to provide di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate.

Example 4

Preparation of (5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl dihydrogen phosphate

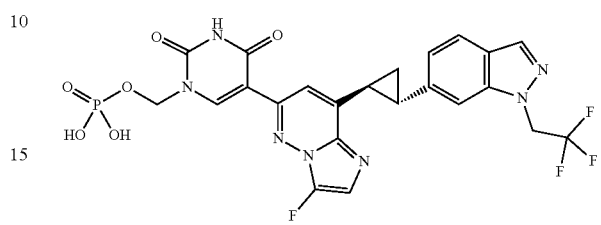

To a solution of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate (90 mg, 0.127 mmol, 1 equiv) in DCM (2.5 mL) was added TFA (0.25 mL). The reaction mixture was stirred at room temperature for 15 min before being concentrated in vacuo and purified by HPLC (10-80% MeCN/water with TFA). LC-MS m/z: 596.1 (M+1). 1H NMR (400 MHz, DMSO-d6) δ 11.92 (s, 1H), 8.36 (s, 1H), 8.15 (s, 1H), 7.78-7.68 (m, 2H), 7.58 (d, J=7.0 Hz, 1H), 7.49 (s, 1H), 7.12 (d, J=8.5 Hz, 1H), 5.57 (d, J=10.8 Hz, 2H), 5.40 (q, J=9.1 Hz, 2H), 3.04 (ddd, J=9.3, 6.3, 4.4 Hz, 1H), 2.79 (dt, J=9.4, 5.2 Hz, 1H), 2.18 (dt, J=8.8, 5.2 Hz, 1H), 1.90 (dt, J=8.6, 5.2 Hz, 1H). 19F NMR (376 MHz, DMSO-d6) δ −70.08 (t, J=9.2 Hz, 3F), −155.18 (d, J=7.0 Hz, 1F).

The following compounds were prepared in an analogous manner to (5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl) methyl dihydrogen phosphate using the modifications listed below:

Example 5 di-tert-butyl ((5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)-2,4-dioxo-3,4-dihydropyrimidin-1(2H)-yl)methyl) phosphate was prepared using 5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione in place of 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride.

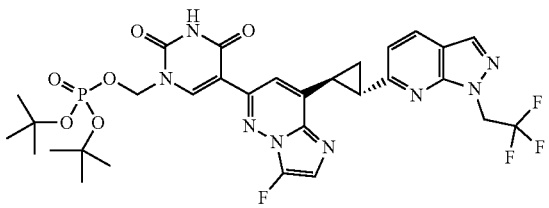 [SMILES: CC(C)(C)OP(=O)(OCn1cc(-c2cc([C@H]3C[C@@H]3c3ccc4cnn(CC(F)(F)F)c4n3)c3ncc(F)n3n2)c(=O)[nH]c1=O)OC(C)(C)C]

(5-(3-fluoro-8-((1S,2S)-2-(1-(2,2,2-trifluoroethyl)-1H-pyrazolo[3,4-b]pyridin-6-yl)cyclopropyl)imidazo[1,2-b]

pyridazin-6-yl)-2,4-dioxo-3,4-dihydropyrimidin-1(2H)-yl)methyl dihydrogen phosphate was prepared using di-tert-butyl ((5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)-2,4-dioxo-3,4-dihydropyrimidin-1(2H)-yl)methyl) phosphate in place of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate.

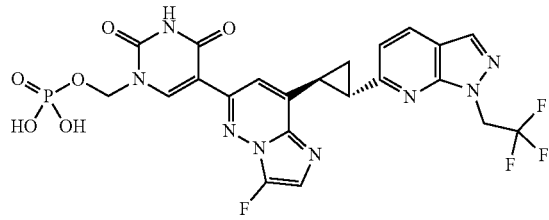 [SMILES: O=c1[nH]c(=O)n(COP(=O)(O)O)cc1-c1cc([C@H]2C[C@@H]2c2ccc3cnn(CC(F)(F)F)c3n2)c2ncc(F)n2n1]

LC-MS m/z: 597.1 (M+1). 1H NMR (400 MHz, DMSO-d6) δ 11.93 (s, 1H), 8.36 (s, 1H), 8.25 (s, 1H), 8.20 (d, J=8.3 Hz, 1H), 7.58 (d, J=7.1 Hz, 1H), 7.51 (s, 1H), 7.38 (d, J=8.3 Hz, 1H), 5.57 (d, J=10.8 Hz, 2H), 5.34 (tt, J=9.3, 4.8 Hz, 2H), 3.24 (ddd, J=8.6, 5.9, 4.1 Hz, 2H), 3.07 (ddd, J=8.9, 6.1, 4.0 Hz, 1H), 2.22 (ddd, J=8.6, 6.2, 3.9 Hz, 1H), 2.06 (ddd, J=9.4, 5.8, 3.9 Hz, 1H). 19F NMR (376 MHz, DMSO-d6) δ −69.89 (t, J=9.1 Hz, 3F), −155.18 (d, J=7.1 Hz, 1F). 31P NMR (162 MHz, DMSO-d6) δ −2.18 (t, J=10.8 Hz, 1P).

Examples 6 and 7 di-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)-3,4-dihydropyrimidin-1(2H)-yl)methyl) phosphate and tetra-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)pyrimidine-1,3(2H,4H)-diyl)bis(methylene)) bis(phosphate) were prepared using 5-(7-((1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione; trifluoroacetic acid in place of 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione; hydrochloride.

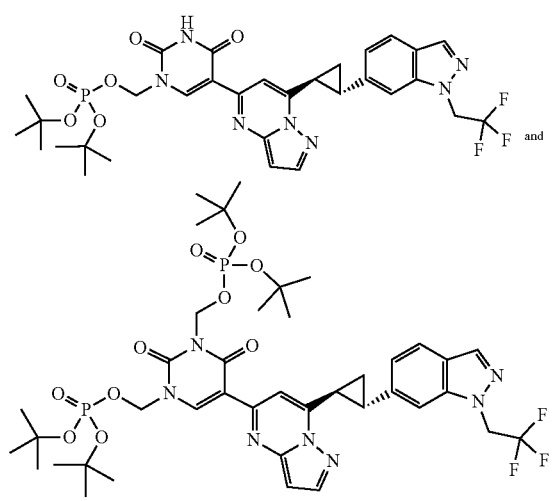

(2,4-dioxo-5-(7-((1S,2S)-2-(1-(2,2,2-trifluoroethyl)-1H-indazol-6-yl)cyclopropyl)pyrazolo[1,5-a]pyrimidin-5-yl)-3,4-dihydropyrimidin-1(2H)-yl)methyl dihydrogen phosphate was prepared using di-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)-3,4-dihydropyrimidin-1(2H)-yl)methyl) phosphate in place of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate

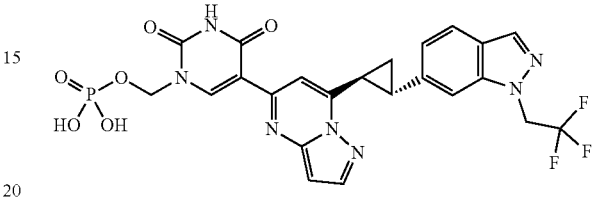

LC-MS m/z: 578.1 (M+1). 1H NMR (400 MHz, DMSO-d6) δ 11.91 (s, 1H), 8.68 (s, 1H), 8.21 (d, J=2.3 Hz, 1H), 8.17 (s, 1H), 7.78 (s, 1H), 7.75 (d, J=8.4 Hz, 1H), 7.68 (s, 1H), 7.20 (dd, J=8.4, 1.3 Hz, 1H), 6.70 (d, J=2.3 Hz, 1H), 5.61 (d, J=11.1 Hz, 2H), 5.42 (q, J=9.1 Hz, 2H), 3.17 (ddd, J=8.5, 6.4, 4.4 Hz, 1H), 2.82 (td, J=7.1, 4.5 Hz, 1H), 1.97 (t, J=8.2 Hz, 2H). 19F NMR (376 MHz, DMSO-d6) δ −70.06 (t, J=9.1 Hz, 3F). 31P NMR (162 MHz, DMSO-d6) δ −2.17 (t, J=11.1 Hz, 1P).

(2,4-dioxo-5-(7-((1S,2S)-2-(1-(2,2,2-trifluoroethyl)-1H-indazol-6-yl)cyclopropyl)pyrazolo[1,5-a]pyrimidin-5-yl)pyrimidine-1,3(2H,4H)-diyl)bis(methylene) bis(dihydrogen phosphate) was prepared using tetra-tert-butyl ((2,4-dioxo-5-(7-((1S,2S)-2-(1-(2,2,2-trifluoroethyl)-1H-indazol-6-yl)cyclopropyl)pyrazolo[1,5-a]pyrimidin-5-yl)pyrimidine-1,3(2H,4H)-diyl)bis(methylene)) bis(phosphate) in place of di-tert-butyl ((5-(3-fluoro-8-((1S,2S)-2-(1-(2,2,2-trifluoroethyl)-1H-indazol-6-yl)cyclopropyl)imidazo[1,2-b]pyridazin-6-yl)-2,4-dioxo-3,4-dihydropyrimidin-1(2H)-yl)methyl) phosphate.

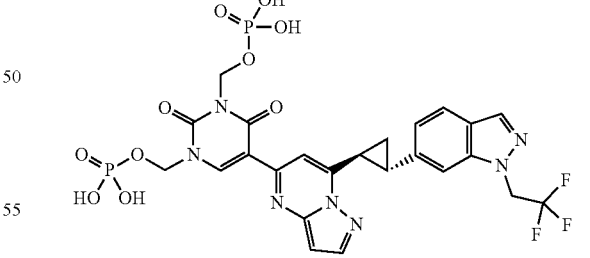

LC-MS m/z: 688.1 (M+1). 1H NMR (400 MHz, DMSO-d6) δ 8.77 (s, 1H), 8.23 (d, J=2.4 Hz, 1H), 8.17 (s, 1H), 7.79 (s, 1H), 7.76 (d, J=8.3 Hz, 1H), 7.63 (s, 1H), 7.21 (dd, J=8.4, 1.3 Hz, 1H), 6.73 (d, J=2.4 Hz, 1H), 5.73 (d, J=6.3 Hz, 2H), 5.69 (d, J=11.1 Hz, 2H), 5.42 (q, J=9.1 Hz, 2H), 3.21 (td, J=7.4, 4.5 Hz, 3H), 2.83 (td, J=7.8, 4.5 Hz, 1H), 2.00 (t, J=7.6 Hz, 2H). 19F NMR (376 MHz, DMSO-d6) δ −70.06 (t, J=9.1 Hz, 3F). 31P NMR (162 MHz, DMSO-d6) δ −2.15 (t, J=11.1 Hz), −3.45 (t, J=6.5 Hz).

Example 8

Preparation of (S)-6-((1-(5-(2,4-dimethoxypyrimidin-5-yl)pyrazolo[1,5-a]pyrimidin-7-yl)-4,4-difluoropyrrolidin-3-yl)oxy)-1-(2,2,2-trifluoroethyl)-1H-pyrazolo[4,3-c]pyridine

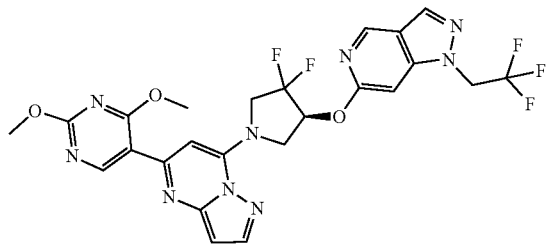 [SMILES: COc1ncc(-c2cc(N3C[C@H](Oc4cc5c(cn4)cnn5CC(F)(F)F)C(F)(F)C3)n3nccc3n2)c(OC)n1]

To (S)-1-(5-(2,4-dimethoxypyrimidin-5-yl)pyrazolo[1,5-a]pyrimidin-7-yl)-4,4-difluoropyrrolidin-3-ol (99 mg, 0.26 mmol), 6-bromo-1-(2,2,2-trifluoroethyl)-1H-pyrazolo[4,3-c]pyridine (82 mg, 0.29 mmol), copper(I) iodide (28 mg, 0.15 mmol), 3,4,7,8-tetramethyl-1,10-phenanthroline (13 mg, 0.06 mmol), and cesium carbonate (132 mg, 0.41 mmol) in a sealed vessel was added toluene (2.6 mL). The mixture was heated to 110° C. for 14 h and then to 135° C. for 24 h. Copper(I) iodide (25 mg, 0.13 mmol), 3,4,7,8-tetramethyl-1,10-phenanthroline (12 mg, 0.05 mmol), cesium carbonate (131 mg, 0.4 mmol), and toluene (0.5 mL) were then added to the mixture and continued to stir at 135° C. After 24 h, the mixture was cooled to ambient temperature and filtered through celite. The cake was rinsed with EtOAc and the combined filtrate was concentrated in vacuo. Purification by column chromatography (EtOAc/hexanes) afforded (S)-6-((1-(5-(2,4-dimethoxypyrimidin-5-yl)pyrazolo[1,5-a]pyrimidin-7-yl)-4,4-difluoropyrrolidin-3-yl)oxy)-1-(2,2,2-trifluoroethyl)-1H-pyrazolo[4,3-c]pyridine.

LC-MS m/z: 578.1 (M+1).

Preparation of (S)-5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)pyrimidine-2,4(1H,3H)-dione

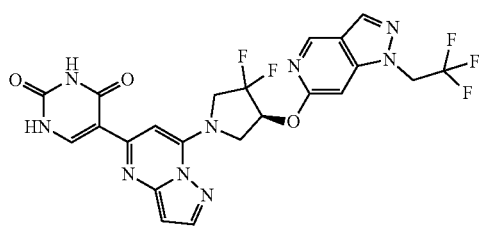 [SMILES: O=c1[nH]cc(-c2cc(N3C[C@H](Oc4cc5c(cn4)cnn5CC(F)(F)F)C(F)(F)C3)n3nccc3n2)c(=O)[nH]1]

To (S)-6-((1-(5-(2,4-dimethoxypyrimidin-5-yl)pyrazolo[1,5-a]pyrimidin-7-yl)-4,4-difluoropyrrolidin-3-yl)oxy)-1-(2,2,2-trifluoroethyl)-1H-pyrazolo[4,3-c]pyridine (104 mg, 0.18 mmol) was added MeOH (1 mL) and 1 M HCl(aq) (1 mL). The mixture was heated to 70° C. for 5 h. Purification by Prep HPLC (water/MeCN with 0.1% TFA) afforded (S)-5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)pyrimidine-2,4(1H,3H)-dione (92 mg, 77%) as a TFA salt.

LC-MS m/z: 550.0 (M+1). 1H NMR (400 MHz, DMSO-d6) δ 11.75 (d, J=3.7 Hz, 1H), 11.59 (s, 1H), 8.88 (d, J=1.0 Hz, 1H), 8.43 (d, J=6.1 Hz, 1H), 8.40 (d, J=0.9 Hz, 1H), 8.12 (d, J=2.3 Hz, 1H), 7.36 (s, 1H), 7.04 (s, 1H), 6.48 (d, J=2.2 Hz, 1H), 6.03 (dq, J=9.3, 4.7 Hz, 1H), 5.41 (qd, J=9.2, 2.5 Hz, 2H), 4.79-4.58 (m, 3H), 4.29 (d, J=12.5 Hz, 1H). 19F NMR (377 MHz, DMSO-d6) δ −70.16 (t, J=9.2 Hz), −75.26, −108.37 (d, J=238.3 Hz), −119.70 (d, J=237.7 Hz).

Example 9

Preparation of (S)-di-tert-butyl ((5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl) phosphate

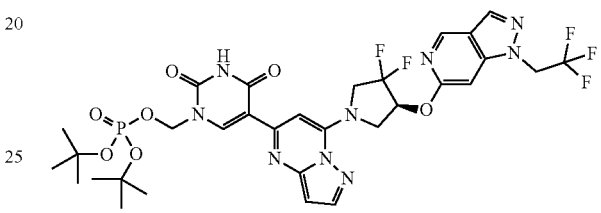

To (S)-5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)pyrimidine-2,4(1H,3H)-dione 2,2,2-trifluoroacetate (60 mg, 0.09 mmol) in EtOAc (30 mL) was washed with saturated NaHCO3(aq) (20 mL). The organics were dried over Na2SO4, concentrated in vacuo, and used without further purification. To crude material was added KHCO3 (14 mg, 0.14 mmol, 1.5 equiv) and DMAc (0.35 mL) followed by di-tert-butyl (chloromethyl) phosphate (30 mg, 0.11 mmol, 1.2 equiv) in DMAc (0.2 mL). The reaction mixture was heated to 60° C. and stirred for 17 h. The reaction mixture was subsequently diluted with EtOAc (30 mL), washed with brine (25 mL). The organic layer was dried over Na2SO4, filtered, and concentrated in vacuo to provide crude (S)-di-tert-butyl ((5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl) phosphate that was used without further purification.

LC-MS m/z: 716.0 (M-[t-Bu]+2).

Preparation of (S)-(5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl dihydrogen phosphate

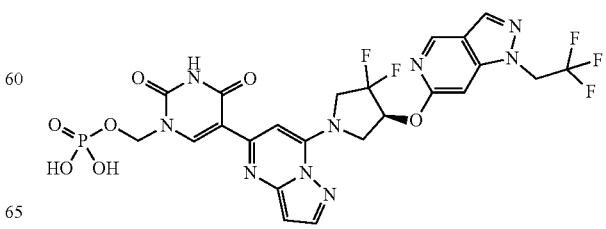

To crude (S)-di-tert-butyl ((5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl) phosphate in DCM (1 mL) was added TFA (0.1 mL). After 30 min, more TFA (0.4 mL) was added. After 30 min, the mixture was concentrated in vacuo. Purification by Prep HPLC (water/MeCN with 0.1% TFA) afforded (S)-(5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl dihydrogen phosphate (39 mg, 56% overall) as a TFA salt.

LC-MS m/z: 660.0 (M+1). 1H NMR (400 MHz, DMSO-d6) δ 11.84 (s, 1H), 8.87 (s, 1H), 8.67 (s, 1H), 8.40 (s, 1H), 8.11 (d, J=2.3 Hz, 1H), 7.36 (s, 1H), 7.10 (s, 1H), 6.46 (d, J=2.3 Hz, 1H), 6.02 (h, J=4.7 Hz, 1H), 5.57 (d, J=10.9 Hz, 2H), 5.40 (q, J=8.8 Hz, 2H), 4.78-4.54 (m, 3H), 4.23 (d, J=12.2 Hz, 1H). 19F NMR (377 MHz, DMSO-d6) δ −70.17 (t, J=9.1 Hz), −75.37, −108.21 (d, J=237.8 Hz), −119.50 (d, J=237.6 Hz). 31P NMR (162 MHz, DMSO-d6) δ −2.27 (t, J=10.9 Hz).

Example 10

Preparation of (S)-di-tert-butyl ((5-(8-(3,3-difluoro-4-((2-(trifluoromethyl)pyridin-4-yl)oxy)pyrrolidin-1-yl)-3-fluoroimidazo[1,2-b]pyridazin-6-yl)-2,4-dioxo-3,4-dihydropyrimidin-1(2H)-yl)methyl) phosphate

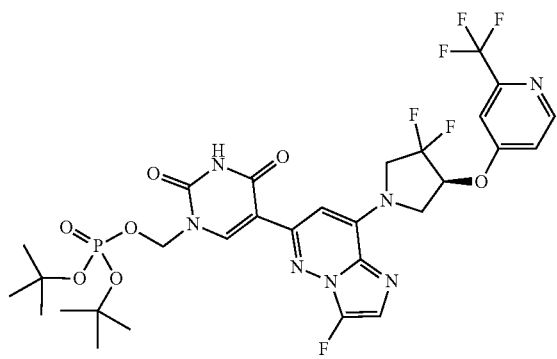 [SMILES: CC(C)(C)OP(=O)(OCn1cc(-c2cc(N3C[C@H](Oc4ccnc(C(F)(F)F)c4)C(F)(F)C3)c3ncc(F)n3n2)c(=O)[nH]c1=O)OC(C)(C)C]

To (S)-5-(8-(3,3-difluoro-4-((2-(trifluoromethyl)pyridin-4-yl)oxy)pyrrolidin-1-yl)-3-fluoroimidazo[1,2-b]pyridazin-6-yl)pyrimidine-2,4(1H,3H)-dione; TFA salt (81 mg, 0.13 mmol) in EtOAc (60 mL) was washed with sat NaHCO₃ (aq) (20 mL). The organics were concentrated in vacuo and used without further purification. To the crude material was added KHCO₃ (20 mg, 0.19 mmol, 1.5 equiv) and DMAc (0.75 mL) followed by di-tert-butyl (chloromethyl) phosphate (41 mg, 0.16 mmol, 1.2 equiv) in DMAc (0.25 mL). The reaction mixture was heated to 60° C. and stirred for 17 h. The reaction mixture was subsequently diluted with EtOAc (30 mL), washed with brine (2×20 mL). The organic layer was dried over Na2SO4, filtered, and concentrated in vacuo to provide crude (S)-di-tert-butyl ((5-(8-(3,3-difluoro-4-((2-(trifluoromethyl)pyridin-4-yl)oxy)pyrrolidin-1-yl)-3-fluoroimidazo[1,2-b]pyridazin-6-yl)-2,4-dioxo-3,4-dihydropyrimidin-1(2H)-yl)methyl) phosphate that was used without further purification.

LC-MS m/z: 736.08 (M+1).

Preparation of (S)-(5-(8-(3,3-difluoro-4-((2-(trifluoromethyl)pyridin-4-yl)oxy)pyrrolidin-1-yl)-3-fluoroimidazo[1,2-b]pyridazin-6-yl)-2,4-dioxo-3,4-dihydropyrimidin-1(2H)-yl)methyl dihydrogen phosphate

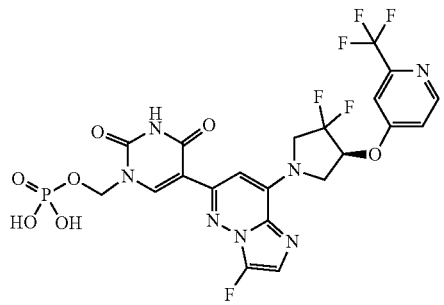 [SMILES: O=c1[nH]c(=O)n(COP(=O)(O)O)cc1-c1cc(N2C[C@H](Oc3ccnc(C(F)(F)F)c3)C(F)(F)C2)c2ncc(F)n2n1]

To crude (S)-di-tert-butyl ((5-(8-(3,3-difluoro-4-((2-(trifluoromethyl)pyridin-4-yl)oxy)pyrrolidin-1-yl)-3-fluoroimidazo[1,2-b]pyridazin-6-yl)-2,4-dioxo-3,4-dihydropyrimidin-1(2H)-yl)methyl) phosphate in DCM (1 mL) was added TFA (0.5 mL). After 1 h, more TFA (0.5 mL) was added. After 30 min, the mixture was concentrated in vacuo. Purification by Prep HPLC (water/MeCN with 0.1% TFA) afforded (S)-(5-(8-(3,3-difluoro-4-((2-(trifluoromethyl)pyridin-4-yl)oxy)pyrrolidin-1-yl)-3-fluoroimidazo[1,2-b]pyridazin-6-yl)-2,4-dioxo-3,4-dihydropyrimidin-1(2H)-yl) methyl dihydrogen phosphate (42 mg, 63% overall) as a TFA salt.

LC-MS m/z: 624.0 (M+1). 1H NMR (400 MHz, DMSO-d6) δ 11.83 (s, 1H), 8.66 (d, J=5.7 Hz, 1H), 8.28 (s, 1H), 7.68 (d, J=2.4 Hz, 1H), 7.49 (dd, J=5.8, 2.4 Hz, 1H), 7.46 (d, J=7.2 Hz, 1H), 6.62 (s, 1H), 5.86-5.78 (m, 1H), 5.55 (d, J=10.8 Hz, 2H), 4.70-4.53 (m, 1H), 4.53-4.34 (m, 2H), 4.34-4.15 (m, 1H). 19F NMR (377 MHz, DMSO-d6) δ −67.17, −75.35, −106.97 (d, J=242.2 Hz), −120.71 (d, J=240.3 Hz), −154.97 (d, J=7.1 Hz). 31P NMR (162 MHz, DMSO-d6) δ −2.20 (t, J=10.6 Hz).

Example 11

Preparation of (S)-di-tert-butyl ((5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)-2,4-dioxo-3,4-dihydropyrimidin-1(2H)-yl)methyl) phosphate

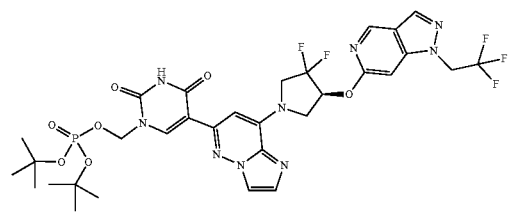

To (S)-5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)pyrimidine-2,4(1H,3H)-dione; TFA salt (52 mg, 0.078 mmol) in NMP (0.5 mL) was added imidazole (14 mg, 0.206 mmol). The mixture was stirred for 3 h, after which water (5 mL) was added. The resulting white precipitate was isolated by filtration, washing twice with water, and dried overnight to afford (S)-5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)pyrimidine-2,4(1H,3H)-dione.

(S)-di-tert-butyl ((5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)-2,4-dioxo-3,4-dihydropyrimidin-1(2H)-yl)methyl) phosphate was then prepared in the manner described for (S)-di-tert-butyl ((5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl) phosphate, using (S)-5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)pyrimidine-2,4(1H,3H)-dione in place of (S)-5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)pyrimidine-2,4(1H,3H)-dione. LC-MS m/z: 771.6 (M+1).

Preparation of (S)-(5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)-2,4-dioxo-3,4-dihydropyrimidin-1(2H)-yl)methyl dihydrogen phosphate

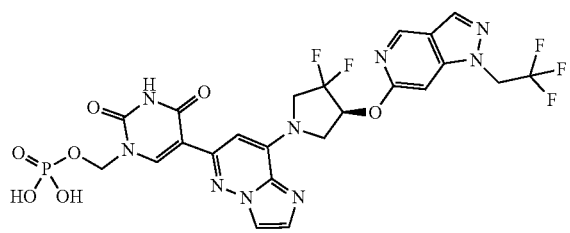 [SMILES: O=c1[nH]c(=O)n(COP(=O)(O)O)cc1-c1cc(N2C[C@H](Oc3cc4c(cn3)cnn4CC(F)(F)F)C(F)(F)C2)c2nccn2n1]

(S)-(5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)-2,4-dioxo-3,4-dihydropyrimidin-1(2H)-yl)methyl dihydrogen phosphate was prepared in the manner described for (S)-(5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl dihydrogen phosphate, using (S)-di-tert-butyl ((5-(8-(3,3-difluoro-4-((1-(2,2,2-trifluoroethyl)-1H-pyrazolo[4,3-c]pyridin-6-yl)oxy)pyrrolidin-1-yl)imidazo[1,2-b]pyridazin-6-yl)-2,4-dioxo-3,4-dihydropyrimidin-1(2H)-yl)methyl) phosphate in place of (S)-di-tert-butyl ((5-(7-(3,3-difluoro-4-((1-(2,2,2-trifluoroethyl)-1H-pyrazolo[4,3-c]pyridin-6-yl)oxy)pyrrolidin-1-yl)pyrazolo[1,5-a]pyrimidin-5-yl)-2,4-dioxo-3,4-dihydropyrimidin-1(2H)-yl)methyl) phosphate.

LC-MS m/z: 659.6 (M+1). 1H NMR (400 MHz, DMSO-d6) δ 11.78 (s, 1H), 8.88 (d, J=1.1 Hz, 1H), 8.40 (d, J=1.0 Hz, 1H), 8.25 (s, 1H), 8.10 (d, J=1.2 Hz, 1H), 7.62-7.56 (m, 1H), 7.35 (s, 1H), 6.61 (s, 1H), 6.00 (s, 1H), 5.53 (d, J=10.7 Hz, 2H), 5.39 (q, J=9.0 Hz, 2H), 4.71-4.38 (m, 3H), 4.20 (s, 1H). 19F NMR (376 MHz, DMSO-d6) δ −70.15 (t, J=9.1 Hz), −108.33 (d, J=242.5 Hz), −119.76 (d, J=237.7 Hz). 31P NMR (162 MHz, DMSO-d6) δ −2.25 (t, J=10.9 Hz).

Biological Data

Comparative Examples

Comparative Examples may be found in U.S. patent application Ser. No. 17/243,911, filed 29 Apr. 2021, the contents of which are hereby incorporated by reference in its entirety.

Briefly, the compounds may be synthesized in the following manner:

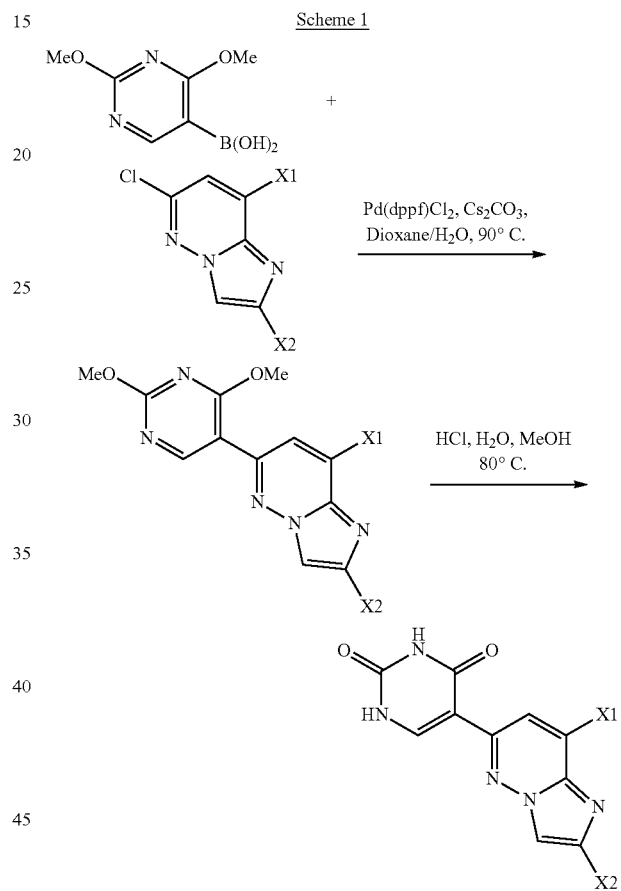

Scheme 1

Representative synthetic Scheme 1 shows a general synthesis of compounds of the disclosure. The methodology is compatible with a wide variety of functionalities. In Representative Synthesis 1, a suitably substituted chloroimidazopyridazine (or the corresponding bromo- or iodo-compound) is combined with (2,4-dimethoxypyrimidin-5-yl)boronic acid in a suitable solvent system (e.g. water+dioxane, THF, DME, toluene etc.) in the presence of a palladium catalyst (e.g. Pd(dppf)Cl$_2$, Pd(PPh$_3$)$_4$ etc.) and base (e.g. Cs$_2$CO$_3$, K$_2$CO$_3$, K$_3$PO$_4$ etc.) at elevated temperature (e.g., ranging from about 80-120° C.), which can be performed, for example, in a microwave reactor or with conventional heating. Subsequently, the resultant suitably substituted 2,4-dimethoxypyrimidine can be treated with an acid (e.g hydrochloric acid) in a suitable solvent system (e.g. water+methanol, ethanol etc.) at elevated temperature (e.g., ranging from about 50-80° C.).

Scheme 2

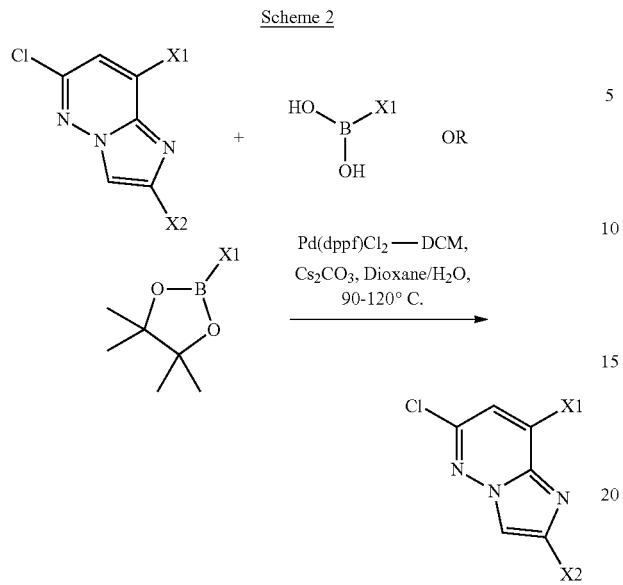

Representative synthetic Scheme 2 shows a general synthesis of the compounds of the embodiments. The methodology is compatible with a wide variety of functionalities. In Representative synthetic Scheme 2, a suitably substituted bromoimidazopyridazine (or the corresponding chloro- or iodo-compound) is combined with an alkyl boronic acid or boronic acid derivate (e.g. boronate ester or trifluoroborate salt) in a suitable solvent system (e.g. water+dioxane, THF, DME, toluene etc.) in the presence of a palladium catalyst (e.g. Pd(dppf)Cl$_2$, cataCXium-A-Pd G3 etc.) and base (e.g. Cs$_2$CO$_3$, K$_2$CO$_3$, K$_3$PO$_4$ etc.) at elevated temperature (e.g., ranging from about 90-150° C.), which can be performed in microwave reactor or with conventional heating).

Scheme 3

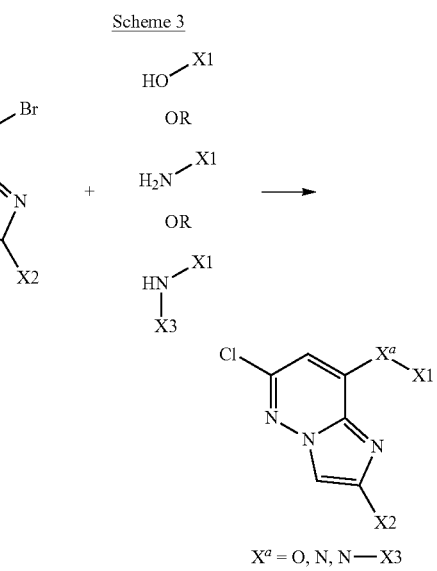

$X^a$ = O, N, N—X3

Representative synthetic Scheme 3 shows a general synthesis of the compounds of the embodiments. The methodology is compatible with a wide variety of functionalities. In representative synthetic Scheme 3, a suitably substituted bromoimidazopyridazine (or the corresponding chloro- or fluoro-compound) is combined with a nucleophile (e.g. amine, alcohol, heterocycle etc.) in a suitable solvent system (e.g. acetonitrile, EtOH, THF, NMP etc.) in the presence of a base (e.g. Cs$_2$CO$_3$, K$_2$CO$_3$ triethylamine, DIPEA, NaH etc.) at ambient or elevated temperature (e.g., ranging from about 20-90° C.).

Scheme 4

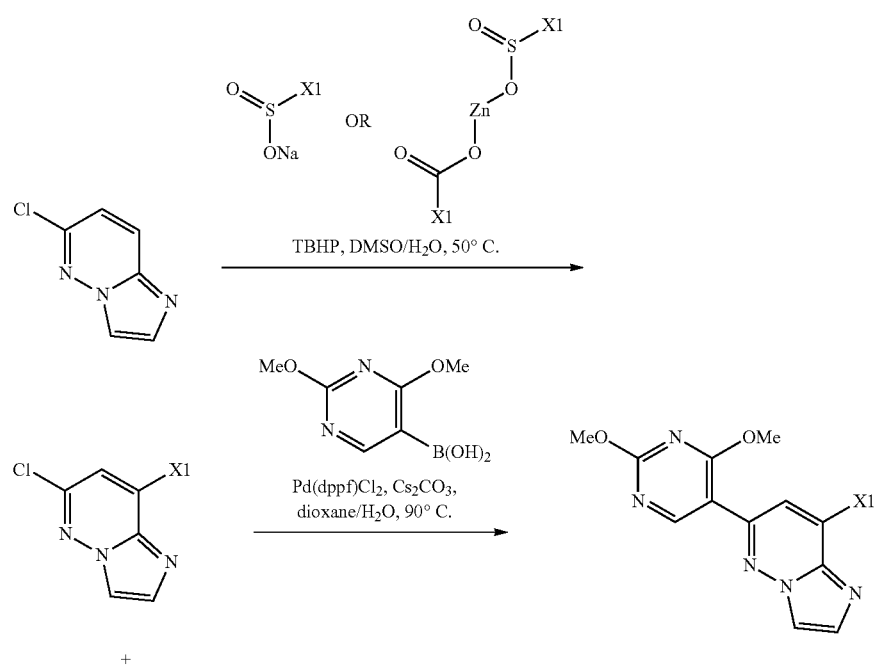

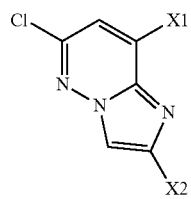  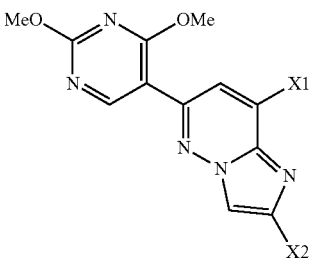

Representative synthetic Scheme 4 shows a general synthesis of the compounds of the embodiments. The methodology is compatible with a wide variety of functionalities. In representative synthetic Scheme 4, a suitably substituted chloroimidazopyridazine is combined with a radical precursor, such as a sodium or zinc alkyl sulfinate, in a suitable solvent system (e.g. DMSO/H$_2$O, DCE/H$_2$O etc.) in the presence of an oxidant (e.g. TBHP) at ambient or elevated temperature (e.g., ranging from about 20-60° C.). A variety of radical precursor and reaction conditions can be used to generate the appropriate alkyl radical intermediate, including Minisci conditions (i.e. alkyl carboxylic acid, (NH$_4$)$_2$S$_2$O$_9$, AgNO$_3$, TFA).

Scheme 5

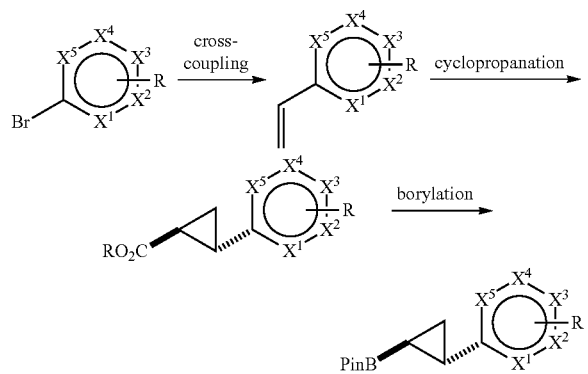

X$^1$, X$^2$, X$^3$, X$^4$, and X$^5$ are independently N or C.

Representative synthetic Scheme 5 shows a general synthesis of the compounds of the embodiments. The methodology is compatible with a wide variety of functionalities. In representative synthetic Scheme 5, a suitably substituted aryl or heteroaryl halide is combined with potassium vinyltrifluoroborate (or the analogous -Bpin, -BMIDA or —B(OH)$_2$ reagent) in a suitable solvent system (e.g. water+ THF, dioxane, DME, toluene etc.) in the presence of a palladium catalyst (e.g. Pd(dppf)Cl$_2$, Pd(PPh$_3$)$_4$ etc.) and base (e.g. K$_2$CO$_3$, Cs$_2$CO$_3$, K$_3$PO$_4$ etc.) at elevated temperature (e.g., ranging from about 80-120° C., can be performed in microwave reactor or with conventional heating). Subsequently, the suitably substituted alkene, in a suitable solvent system (e. g. DCM), is treated with tetrakis (acetonitrile)[2-[(4R)-4,5-dihydro-4-phenyl-2-oxazolyl-N] phenyl]ruthenium(II) hexafluorophosphate (or another suitable transition metal catalyst) and 1,3-dioxoisoindolin-2-yl 2-diazoacetate at low temperature (e.g., ranging from about −20° C.-5° C.). The resulting, suitably substituted, N-hydroxyphthalimide ester is combined with methyl isonicotinate (or another suitable isonicotinate derivative, e.g. isonicotinate t-butyl ester, etc.) and bis(pinacolato)diboron in a suitable solvent (e. g. EtOAc, CF$_3$Ph, etc. isonicotinate t-butyl ester) at elevated temperature (e.g., ranging from about 60-100° C.). Alternatively, the borylation reaction can be performed by combining a suitably substituted, N-hydroxyphthalimide ester with bis(catecholato)diboron in a suitable solvent system (e. g. DMF) under blue LED lights, and the resulting boronate ester combined with pinacol and triethylamine.

Alternatively, this reaction sequence can provide racemic mixtures of the compounds by combining a suitably substituted alkene with ethyl diazoacetate in a suitable solvent system (i.e. Toluene) at elevated temperature (e.g. ranging from about 80-120° C.). Subsequently, the ethyl ester can be hydrolyzed under basic aqueous conditions (e.g. LiOH or NaOMe), and the resulting acid can be combined with N-hydroxyphthalmide with a suitable coupling reagent (e.g. DIC, EDC). The final borylation step can be performed as above.

Comparative Example A: 5-(8-((1S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione Intermediate A: 6-(2,4-dimethoxypyrimidin-5-yl)-8-((1S,2S)-2-(1-(2,2,2-trifluoroethyl)-1H-indazol-5-yl) cyclopropyl)imidazo[1,2-b]pyridazine

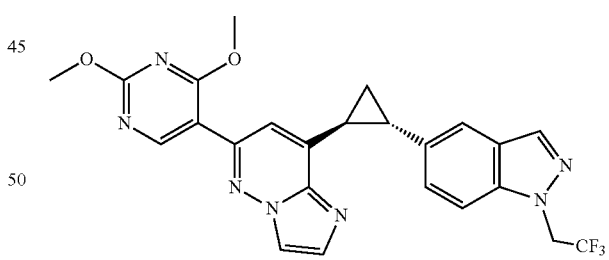

6-(2,4-dimethoxypyrimidin-5-yl)-8-((1S,2S)-2-(1-(2,2,2-trifluoroethyl)-1H-indazol-5-yl)cyclopropyl)imidazo[1,2-b] pyridazine was prepared as follows: 8-cyclopropyl-6-(2,4-dimethoxypyrimidin-5-yl)-2-methyl-imidazo[1,2-b] pyridazine was prepared as follows: A microwave vial was charged with (2,4-dimethoxypyrimidin-5-yl)boronic acid (59.4 mg, 0.323 mmol, 1.0 equiv), Pd(dppf)Cl$_2$—CH$_2$Cl$_2$ (23.6 mg, 0.032 mmol, 10 mol %), Cs$_2$CO$_3$ (210 mg, 0.645 mmol, 2 equiv) and 6-chloro-8-((1S,2S)-2-(1-(2,2,2-trifluoroethyl)-1H-indazol-5-yl)cyclopropyl)imidazo[1,2-b] pyridazine (1 equiv). The reaction mixture was dissolved in 3:1 dioxane/H$_2$O (4 mL), purged with argon, and was stirred at 80° C. for 5 h. The reaction mixture was directly purified by silica gel chromatography (0-15% MeOH/CH₂Cl₂). Compound was repurified by SiO₂ chromatography (0-100% EtOAc/Hexanes), affording 8-cyclopropyl-6-(2,4-dimethoxypyrimidin-5-yl)-2-methyl-imidazo[1,2-b]pyridazine. ES/MS m/z: 496.05 [M+H].

trifluoroethyl)-1H-indazol-5-yl)cyclopropyl)imidazo[1,2-b]pyridazine (1 equiv). The reaction mixture was dissolved in 3:1 dioxane/H₂O (4 mL), purged with argon, and was stirred at 80° C. for 5 h. The reaction mixture was directly purified by silica gel chromatography (0-15% MeOH/CH₂Cl₂). Compound was repurified by SiO₂ chromatography (0-100% EtOAc/Hexanes), affording 8-cyclopropyl-6-(2,4-dimethoxypyrimidin-5-yl)-2-methyl-imidazo[1,2-b]pyridazine. ES/MS m/z: 312.20 [M+H].

Intermediate B. 6-chloro-8-(3,3-difluoro-4,4-dimethyl-pyrrolidin-1-yl)imidazo[1,2-b]pyridazine

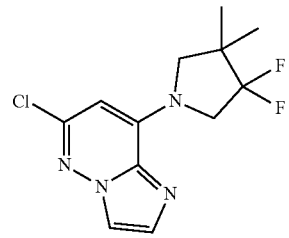

6-chloro-8-(3,3-difluoro-4,4-dimethyl-pyrrolidin-1-yl)imidazo[1,2-b]pyridazine was prepared in the manner described for 6-chloro-8-(3,3-dimethylpyrrolidin-1-yl)imidazo[1,2-b]pyridazine, but replacing 3,3-dimethylpyrrolidine hydrochloride with 3,3-difluoro-4,4-dimethyl-pyrrolidine hydrochloride.

A microwave vial was charged with 8-bromo-6-chloro-imidazo[1,2-b]pyridazine (250 mg, 1.08 mmol, 3,3-difluoro-4,4-dimethyl-pyrrolidine hydrochloride, 1.1 equiv), DIPEA (0.481 mL, 2.69 mmol, 2.5 equiv), and MeCN (5 mL). The reaction mixture was heated to 85° C. After 24 hours, the reaction mixture was concentrated. The residue obtained was triturated with water, the resulting solids were filtered, washed with water, and dried affording 6-chloro-8-(3,3-dimethylpyrrolidin-1-yl)imidazo[1,2-b]pyridazine. ES/MS m/z: 287.10 [M+H].

5-(8-((1S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione was prepared as follows: To a solution of 6-(2,4-dimethoxypyrimidin-5-yl)-8-((1S,2S)-2-(1-(2,2,2-trifluoroethyl)-1H-indazol-5-yl)cyclopropyl)imidazo[1,2-b]pyridazine in MeOH (1.5 mL) was added 1.5 M HCl(aq) solution (1 mL). The reaction vessel was heated to 80° C. for 6 h. Solids separated were filtered, washed with water and dried affording 5-(8-cyclopropyl-2-methyl-imidazo[1,2-b]pyridazin-6-yl)-1H-pyrimidine-2,4-dione and isolated by filtration as a HCl salt. ES/MS m/z: 468.00 [M+H]. ¹H NMR (400 MHz, DMSO-d6) δ 11.62-11.48 (m, 2H), 8.35 (s, 1H), 8.14 (s, 1H), 8.04 (d, J=6.0 Hz, 1H), 7.90 (s, 1H), 7.75 (d, J=8.7 Hz, 1H), 7.68 (s, 1H), 7.59 (s, 1H), 7.39 (dd, J=8.8, 1.6 Hz, 1H), 5.44 (q, J=9.2 Hz, 2H), 2.96-2.89 (m, 1H), 2.81-2.74 (m, 1H), 2.04 (dt, J=10.0, 5.3 Hz, 1H), 1.85 (dt, J=8.6, 5.4 Hz, 1H). ¹⁹F NMR (376 MHz, DMSO-d6) δ −70.15 (t, J=9.1 Hz).

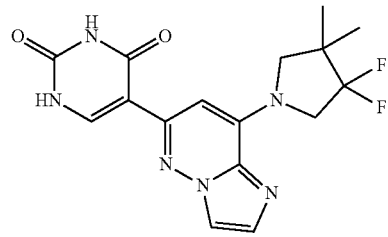 [SMILES: CC1(C)CN(c2cc(-c3c[nH]c(=O)[nH]c3=O)nn3ccnc23)CC1(F)F]

Comparative Example B: 5-[8-(3,3-difluoro-4,4-dimethyl-pyrrolidin-1-yl)imidazo[1,2-b]pyridazin-6-yl]-1H-pyrimidine-2,4-dione

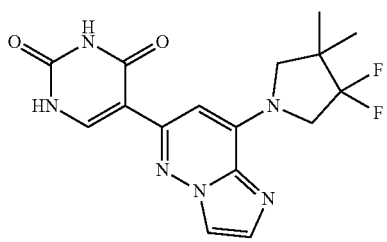 [SMILES: CC1(C)CN(c2cc(-c3c[nH]c(=O)[nH]c3=O)nn3ccnc23)CC1(F)F]

5-[8-(3,3-difluoro-4,4-dimethyl-pyrrolidin-1-yl)imidazo[1,2-b]pyridazin-6-yl]-1H-pyrimidine-2,4-dione was prepared as follows: To a solution of 8-(3,3-difluoro-4,4-dimethyl-pyrrolidin-1-yl)-6-(2,4-dimethoxypyrimidin-5-yl)imidazo[1,2-b]pyridazine in MeOH (2.5 mL) was added 1 M HCl(aq) solution (1.5 mL). The reaction vessel was heated to 80° C. for 6 h. Solids separated were filtered, washed with water and dried affording 5-[8-(3,3-difluoro-4,4-dimethyl-pyrrolidin-1-yl)imidazo[1,2-b]pyridazin-6-yl]-1H-pyrimidine-2,4-dione as an HCl salt. ES/MS: 363.10 [M+1]. ¹H NMR (400 MHz, DMSO-d6) δ 11.58-11.46 (m, 2H), 8.23-8.22 (m, 1H), 8.01-7.97 (m, 1H), 7.81-7.80 (m, 1H), 6.81 (s, 1H), 4.47-4.41 (m, 2H), 3.83-3.82 (m, 2H), 1.22-1.20 (m, 6H). ¹⁹F NMR (377 MHz, DMSO-d6) δ −115.19 (m, 2F).

Comparative Example C

Intermediate 709. Potassium trifluoro((1S,2S)-2-(1-(2,2,2-trifluoroethyl)-1H-indazol-6-yl)cyclopropyl)borate

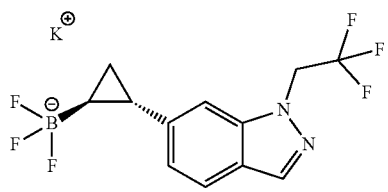 [SMILES: F[B-](F)(F)[C@H]1C[C@@H]1c1ccc2cnn(CC(F)(F)F)c2c1 ; [K+]]

6-((1S,2S)-2-(4,4,5,5-tetramethyl-1,3,2-dioxaborolan-2-yl)cyclopropyl)-1-(2,2,2-trifluoroethyl)-1H-indazole (209 mg, 0.57 mmol) and KHF2 (312 g, 4.0 mmol) were weighed into a vial, and MeOH (2.5 mL) and water (0.5 mL) were added. The mixture was stirred at rt overnight, and then solvent was removed in vacuo. The resulting residue was taken up in MeCN, and filtered to remove solids, washing with MeCN. The filtrate was concentrated in vacuo, then the solid was washed with diethyl ether and dried to afford potassium trifluoro((1S,2S)-2-(4-(trifluoromethyl)phenyl)cyclopropyl)borate. $^1$H NMR (400 MHz, Acetone-d6) δ 7.92 (d, J=1.0 Hz, 1H), 7.53 (d, J=8.4 Hz, 1H), 7.26 (s, 1H), 6.87 (dd, J=8.4, 1.3 Hz, 1H), 5.21 (q, J=9.0 Hz, 2H), 1.80-1.72 (m, 1H), 0.85 (td, J=7.4, 2.6 Hz, 1H), 0.52 (d, J=10.2 Hz, 1H), 0.09--0.02 (m, 1H). $^{19}$F NMR (376 MHz, Acetone-d6) δ −71.97 (t, J=9.0 Hz), −145.46 (d, J=77.9 Hz).

Intermediate 710. 5-bromo-7-((1S,2S)-2-(1-(2,2,2-trifluoroethyl)-1H-indazol-6-yl)cyclopropyl)pyrazolo[1,5-a]pyrimidine

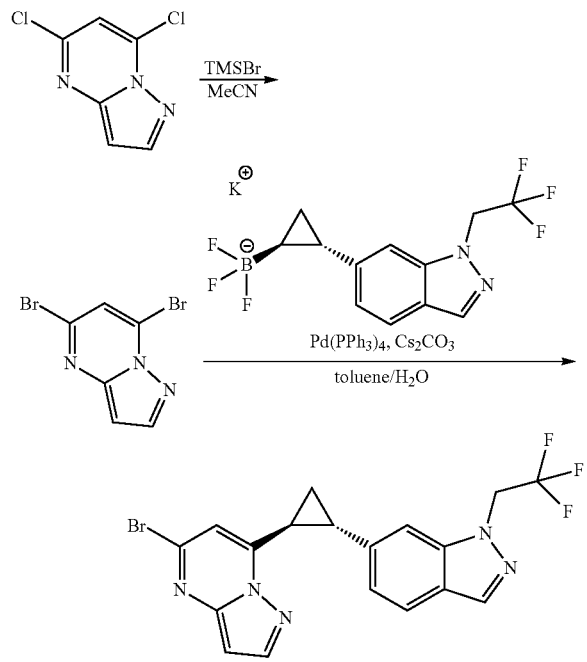

5-bromo-7-((1S,2S)-2-(1-(2,2,2-trifluoroethyl)-1H-indazol-6-yl)cyclopropyl)pyrazolo[1,5-a]pyrimidine was prepared as follows: To a solution of 5,7-dichloropyrazolo[1,5-a]pyrimidine (0.500 g, 2.66 mmol) in MeCN (13 mL) was added bromotrimethylsilane (1.75 mL, 13.3 mmol). The mixture was stirred at 60° C. for 3 h. The suspension was filtered, washing with MeCN, and the solids were dried under vacuum to afford 5,7-dibromopyrazolo[1,5-a]pyrimidine. ES/MS m/z: 276.0 [M+H].

A microwave vial was charged with 5,7-dibromopyrazolo[1,5-a]pyrimidine (354 mg, 1.28 mmol), potassium trifluoro((1S,2S)-2-(1-(2,2,2-trifluoroethyl)-1H-indazol-6-yl)cyclopropyl)borate (295 mg, 0.852 mmol), cesium carbonate (833 mg, 2.56 mmol), and Pd(PPh3)4 (49 mg, 0.043 mmol). The solids were dissolved in toluene (5 mL) and H2O (1 mL), and the mixture was degassed with N2. The vial was sealed and heated to 100° C. for 5 h. The reaction mixture was then cooled and filtered through celite, washing with EtOAc. The filtrate was concentrated in vacuo, and the resulting residue purified by silica gel chromatography (0-100% EtOAc/hexanes), affording 5-bromo-7-((1S,2S)-2-(1-(2,2,2-trifluoroethyl)-1H-indazol-6-yl)cyclopropyl)pyrazolo[1,5-a]pyrimidine. ES/MS m/z: 436.1 [M+H].

Example 456 5-(7-((1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione

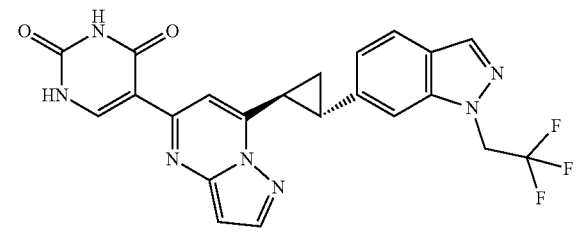 [SMILES: O=c1[nH]cc(-c2cc([C@H]3C[C@@H]3c3ccc4cnn(CC(F)(F)F)c4c3)n3nccc3n2)c(=O)[nH]1]

5-(7-((1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione was prepared as follows: 5-bromo-7-((1S,2S)-2-(1-(2,2,2-trifluoroethyl)-1H-indazol-6-yl)cyclopropyl)pyrazolo[1,5-a]pyrimidine (120 mg, 0.275 mmol), (2,4-ditert-butoxypyrimidin-5-yl)boronic acid (88.5 mg, 0.330 mmol), cesium carbonate (269 mg, 0.825 mmol), and Pd(dppf)Cl2—CH2Cl2 (22.5 mg, 0.0275 mmol) were weighed into a microwave vial, and dioxane (2 mL) and water (0.5 mL) were added. The mixture was degassed with N2, and the vial was sealed and heated to 80° C. for 16 h. The mixture was then cooled to room temperature, and TFA (1 mL) was added slowly. The mixture was stirred at room temperature for an additional 20 min, then concentrated and purified by RP-HPLC (10-90% MeCN/H2O with TFA modifier, Gemini column). ES/MS m/z: 468.1 [M+H]. $^1$H NMR (400 MHz, DMSO-d6) δ 11.62 (dd, J=6.4, 2.0 Hz, 1H), 11.52 (d, J=1.9 Hz, 1H), 8.35 (d, J=6.3 Hz, 1H), 8.19-8.07 (m, 2H), 7.80-7.65 (m, 3H), 7.18 (dd, J=8.4, 1.4 Hz, 1H), 6.63 (d, J=2.3 Hz, 1H), 5.41 (q, J=9.1 Hz, 2H), 3.15 (ddd, J=8.3, 6.6, 4.5 Hz, 1H), 2.84-2.74 (m, 1H), 1.95 (ddd, J=8.3, 6.6, 1.5 Hz, 2H). $^{19}$F NMR (376 MHz, DMSO-d6) δ −70.08 (t, J=9.0 Hz), −75.62.

Comparative Example D

Intermediate 798. 6-((1S,2S)-2-(4,4,5,5-tetramethyl-1,3,2-dioxaborolan-2-yl)cyclopropyl)-1-(2,2,2-trifluoroethyl)-1H-pyrazolo[3,4-b]pyridin

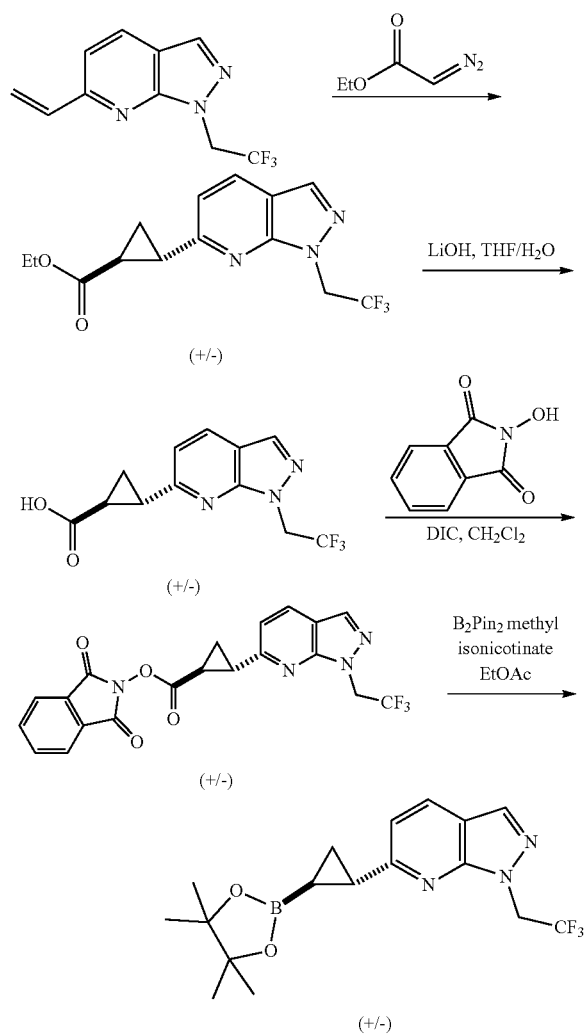

Step 1: To a solution of 1-(2,2,2-trifluoroethyl)-6-vinyl-1H-pyrazolo[3,4-b]pyridine (600 mg, 2.64 mmol, 1 equiv) in toluene (6 mL) was added ethyl diazoacetate (0.42 mL, 3.96 mmol, 1 equiv). The reaction mixture was heated to 80° C. After 24 hours, the reaction mixture was diluted with MeOH (5 mL) and concentrated to ~5 mL. Purification was accomplished by $SiO_2$ chromatography (0-100% EtOAc/Hex), affording racemic ethyl (1S,2S)-2-(1-(2,2,2-trifluoroethyl)-1H-pyrazolo[3,4-b]pyridin-6-yl)cyclopropane-1-carboxylate.

Step 2: To a solution of racemic ethyl (1S,2S)-2-(1-(2,2,2-trifluoroethyl)-1H-pyrazolo[3,4-b]pyridin-6-yl)cyclopropane-1-carboxylate (882 mg, 2.82 mmol, 1 equiv) in 5:1 THF:$H_2O$ (5 mL) was added LiOH—$H_2O$ (591 mg, 14.1 mmol, 5 equiv). The reaction mixture was heated to 45C and stirred for 20 hours. The reaction mixture was neutralized at 0° C. with 2M HCl, then exhaustively extracted with EtOAc. The combined organic layers were dried over $Na_2SO_4$, filtered, and concentrated to afford racemic (1S,2S)-2-(1-(2,2,2-trifluoroethyl)-1H-pyrazolo[3,4-b]pyridin-6-yl)cyclopropane-1-carboxylic acid. ES/MS m/z: 286.10 [M+H].

Step 3: To a solution of racemic (1S,2S)-2-(1-(2,2,2-trifluoroethyl)-1H-pyrazolo[3,4-b]pyridin-6-yl)cyclopropane-1-carboxylic acid (1000 mg, 3.51 mmol, 1 equiv) in $CH_2Cl_2$ (30 mL) was added diisopropylmethanediimine (0.60 mL, 3.86 mmol, 1.1 equiv), DMAP (42.8 mg, 10 mol %), and 2-hydroxyisoindoline-1,3-dione (629 mg, 3.86 mmol, 1.1 equiv). After 5 hours, the reaction mixture was filtered with $CH_2Cl_2$ washings and concentrated. The residue was purified by $SiO_2$ chromatography (0-100% EtOAc/Hex), affording racemic 1,3-dioxoisoindolin-2-yl (1S,2S)-2-(1-(2,2,2-trifluoroethyl)-1H-pyrazolo[3,4-b]pyridin-6-yl)cyclopropane-1-carboxylate.

Step 4: To a solution of racemic 1,3-dioxoisoindolin-2-yl (1S,2S)-2-(1-(2,2,2-trifluoroethyl)-1H-pyrazolo[3,4-b]pyridin-6-yl)cyclopropane-1-carboxylate (1071 mg, 2.49 mmol, 1 equiv) in EtOAc (12 mL) was added $B_2Pin_2$ (1264 mg, 4.98 mmol, 2 equiv) and methyl isonicotinate (0.147 mL, 1.24 mmol, 0.5 equiv). The resulting mixture was heated to 80° C. under an atmosphere of argon. After 12 hours, the reaction mixture was filtered, concentrated, and purified by $SiO_2$ chromatography (0-20% EtOAc/Hex), affording racemic 6-((1S,2S)-2-(4,4,5,5-tetramethyl-1,3,2-dioxaborolan-2-yl)cyclopropyl)-1-(2,2,2-trifluoroethyl)-1H-pyrazolo[3,4-b]pyridine. ES/MS m/z: 368.20 [M+H].

Intermediate 838. 6-((1S,2S)-2-(6-chloro-3-fluoro-imidazo[1,2-b]pyridazin-8-yl)cyclopropyl)-1-(2,2,2-trifluoroethyl)-1H-pyrazolo[3,4-b]pyridine 8-bromo-6-chloro-3-fluoro-imidazo[1,2-b]pyridazine (426 mg, 1.7 mmol), 6-((1S,2S)-2-(4,4,5,5-tetramethyl-1,3,2-dioxaborolan-2-yl)cyclopropyl)-1-(2,2,2-trifluoroethyl)-1H-pyrazolo[3,4-b]pyridine (racemic mixture) (650 mg, 1.42 mmol), cataCXium A Pd G3 (103 mg, 0.142 mmol), and potassium phosphate tribasic (902 mg, 4.25 mmol) were weighed into a microwave vial, which was then evacuated and refilled with $N_2$ 3 times. Pre-degassed dioxane (6.7 mL) and water (1.3 mL) were added, and the vial was sealed and heated to 100° C. for 10 h. The mixture was then filtered through celite, washing with EtOAc. The filtrate was concentrated in vacuo and purified by silica gel chromatography (0-100% EtOAc in hexanes) to afford 4-((1S,2S)-2-(6-chloroimidazo[1,2-b]pyridazin-8-yl)cyclopropyl)-2-(trifluoromethyl)benzonitrile (racemic mixture). ES/MS m/z: 411.10 [M+H].

Intermediate 839. 6-((1S,2S)-2-(6-chloro-3-fluoro-imidazo[1,2-b]pyridazin-8-yl)cyclopropyl)-1-(2,2,2-trifluoroethyl)-1H-pyrazolo[3,4-b]pyridine

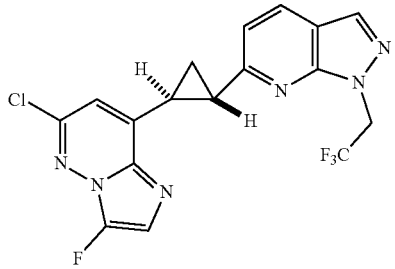 [SMILES: Fc1cnc2c([C@H]3C[C@@H]3c3ccc4cnn(CC(F)(F)F)c4n3)cc(Cl)nn12]

6-((1S,2S)-2-(6-chloro-3-fluoroimidazo[1,2-b]pyridazin-8-yl)cyclopropyl)-1-(2,2,2-trifluoroethyl)-1H-pyrazolo[3,4-b]pyridine was chirally separated from the racemic Intermediate 838 by SFC OJ-H column (15% EtOH).

Intermediate 911. 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[3,4-b]pyridine

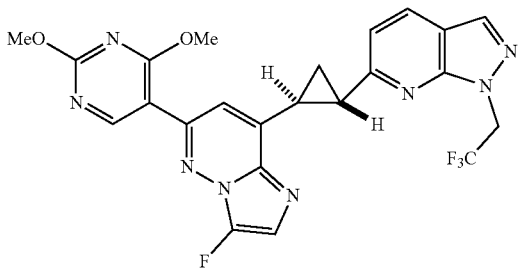 [SMILES: COc1ncc(-c2cc([C@H]3C[C@@H]3c3ccc4cnn(CC(F)(F)F)c4n3)c3ncc(F)n3n2)c(OC)n1]

6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[3,4-b]pyridine was prepared in the manner described for Intermediate A, but replacing 6-chloro-8-((1S,2S)-2-(1-(2,2,2-trifluoroethyl)-1H-indazol-5-yl)cyclopropyl)imidazo[1,2-b]pyridazine with 6-((1S,2S)-2-(6-chloro-3-fluoroimidazo[1,2-b]pyridazin-8-yl)cyclopropyl)-1-(2,2,2-trifluoroethyl)-1H-pyrazolo[3,4-b]pyridine. ES/MS m/z: 515.10 [M+H].

Example 610. 5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione

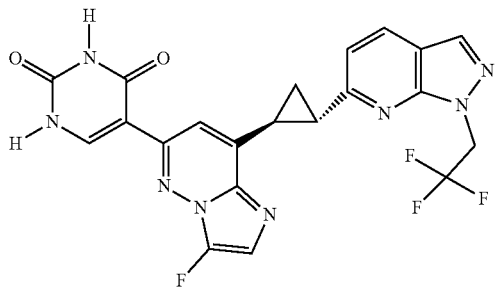 [SMILES: O=c1[nH]cc(-c2cc([C@H]3C[C@@H]3c3ccc4cnn(CC(F)(F)F)c4n3)c3ncc(F)n3n2)c(=O)[nH]1]

5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione was prepared in a manner described for 5-(8-((1S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione, but replacing 6-(2,4-dimethoxypyrimidin-5-yl)-8-((1S,2S)-2-(1-(2,2,2-trifluoroethyl)-1H-indazol-5-yl)cyclopropyl)imidazo[1,2-b]pyridazine with 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[3,4-b]pyridine. ES/MS m/z: 487.10 [M+H]. $^1$H NMR (400 MHz, Methanol-$d_4$) δ 8.20 (s, 1H), 8.12 (s, 1H), 8.12 (d, J=8.2 Hz, 1H), 7.67 (s, 1H), 7.43 (d, J=6.7 Hz, 1H), 7.33 (d, J=8.2 Hz, 1H), 5.35-5.07 (m, 2H), 3.26-3.20 (m, 1H), 3.11-3.04 (m, 1H), 2.20-2.11 (m, 1H), 2.07-1.98 (m, 1H).

Biological Data

The following biological activity data demonstrates some of the properties of some embodiments of the invention.

Thermodynamic Solubility in FASSIF and FESSIF.

The aqueous solubility of compounds over a time of 20 hours was assessed. Solubility was determined at ambient temperature in buffered fasted-state simulated intestinal fluid (FaSSIF, pH 6.5) and buffered fed-state simulated intestinal fluid (FeSSIF, pH 5.0) prepared in-house using BioRelevant Simulated Intestinal Fluid (SIF) powder. Solids were added to FaSSIF or FeSSIF in 1.5-mL Eppendorf tubes, vortexed for 1 minute, then agitated for 20 hours in an Eppendorf ThermoMixer C. To determine concentration in solution, the suspensions were centrifuged for 10 min at 14,800 rpm and supernatants were diluted to a volume of 1 mL with 1:1 v/v acetonitrile:water. All diluted supernatants were analyzed by UPLC using a Waters Acquity UPLC with a PDA UV detector. Results are depicted in Table 3.

Kinetic Solubility at pH 1 and 7

100-fold dilutions of each compound as DMSO stock solution were prepared by combining 3 μL of DMSO stock with 297 μL of the appropriate media in a Millipore solubility filter plate with 0.45 μM polycarbonate filter membrane using Hamilton Starlet liquid handling. The final DMSO Concentration is 1.0% and maximum theoretical compound concentration is 100KM (assuming stock concentration of 10 mM). The filter plate was sealed. Following 24-hour incubation at ambient temperature (22.2-23.6° C.), the samples were vacuum filtered, and the filtrates were collected in a 96 well polypropylene plate for analysis. The collection plate was sealed for analysis. Filtrates were injected into the nitrogen detector for quantification. The equimolar nitrogen response of the detector is calibrated using standards which span the dynamic range of the instrument from 0.08 to 4500 μg/ml nitrogen. The filtrates were quantified with respect to this calibration curve. The calculated solubility values are corrected for background nitrogen present in the DMSO, and the media used to prepare the samples TABLE 3
| Structure | Compound number | FaSSIF (pH 6.5) (ug/mL) | FeSSIF (pH 5.0) (ug/mL) | Kinetic Solubility pH 1 (uM) | Kinetic Solubility pH 7 (uM) |
|---|---|---|---|---|---|
| 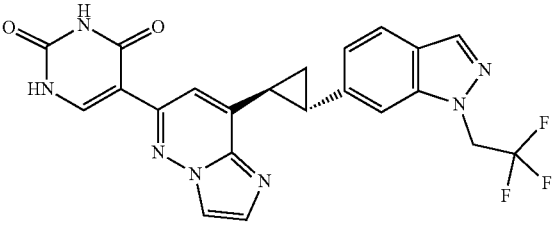 [SMILES: O=c1[nH]cc(-c2cc([C@H]3C[C@@H]3c3ccc4cnn(CC(F)(F)F)c4c3)c3nccn3n2)c(=O)[nH]1] | A | 0.7 | 12.4 | 72 | 10 |
| 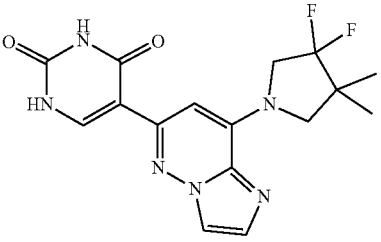 [SMILES: CC1(C)CN(c2cc(-c3c[nH]c(=O)[nH]c3=O)nn3ccnc23)CC1(F)F] | B | 12 | 33 | 95 | 5 |
| 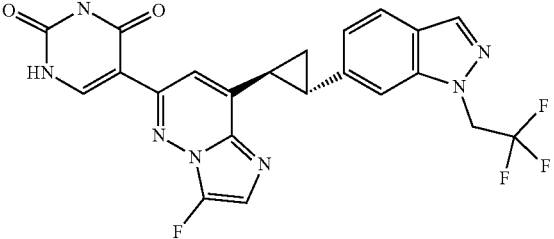 | C | 0.5 | 11.1 | 65 | 7 |
| 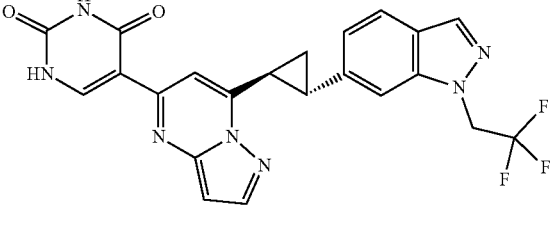 | D | | | 9 | 6 |
| 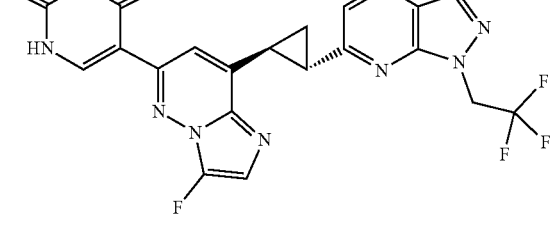 | E | | | 94 | 8 |
| 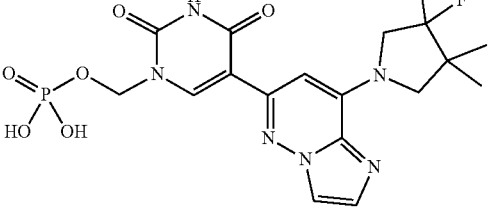 | Ex 1 | >1000 | >1000 | >100 | >100 |

TABLE 3-continued

| Structure | Compound number | FaSSIF (pH 6.5) (ug/mL) | FeSSIF (pH 5.0) (ug/mL) | Kinetic Solubility pH 1 (uM) | Kinetic Solubility pH 7 (uM) |
|---|---|---|---|---|---|
| 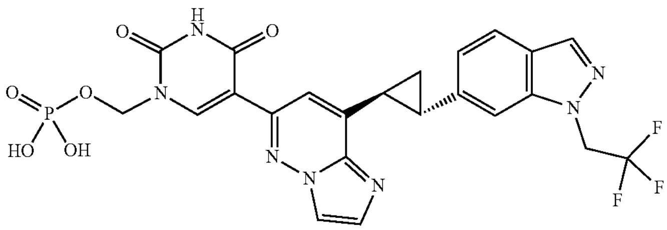 [SMILES: O=c1[nH]c(=O)n(COP(=O)(O)O)cc1-c1cc([C@H]2C[C@@H]2c2ccc3cnn(CC(F)(F)F)c3c2)c2nccn2n1] | Ex 2 | | | 3 | 89 |
| 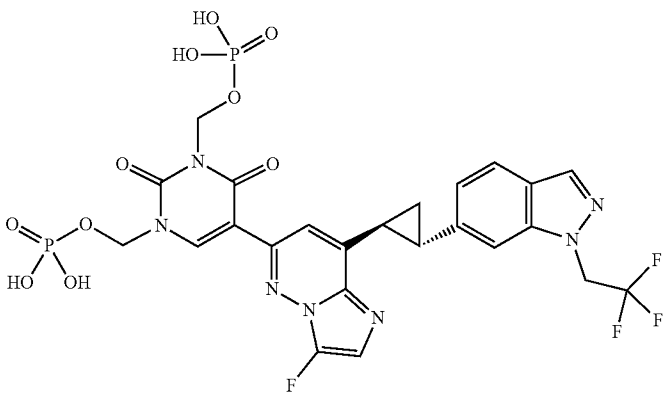 [SMILES: O=c1c(-c2cc([C@H]3C[C@@H]3c3ccc4cnn(CC(F)(F)F)c4c3)c3ncc(F)n3n2)cn(COP(=O)(O)O)c(=O)n1COP(=O)(O)O] | Ex 3 | | | 91 | >100 |
| 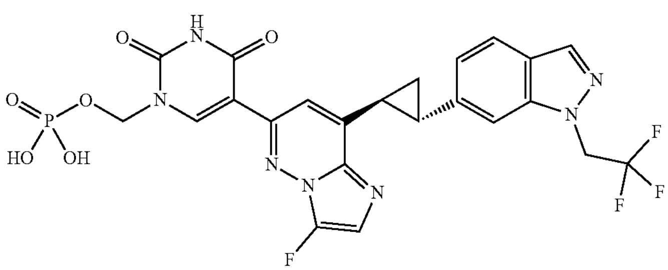 [SMILES: O=c1[nH]c(=O)n(COP(=O)(O)O)cc1-c1cc([C@H]2C[C@@H]2c2ccc3cnn(CC(F)(F)F)c3c2)c2ncc(F)n2n1] | Ex 4 | 1100 | >5400 | 96 | >100 |
| 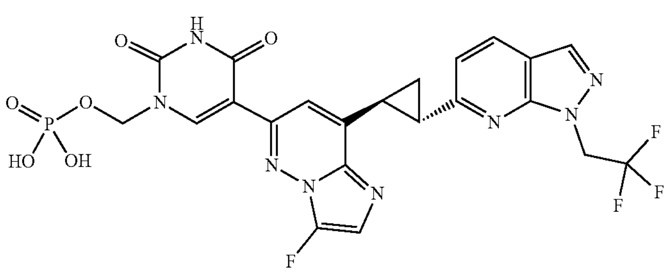 [SMILES: O=c1[nH]c(=O)n(COP(=O)(O)O)cc1-c1cc([C@H]2C[C@@H]2c2ccc3cnn(CC(F)(F)F)c3n2)c2ncc(F)n2n1] | Ex 5 | | | 79 | 86 |
| 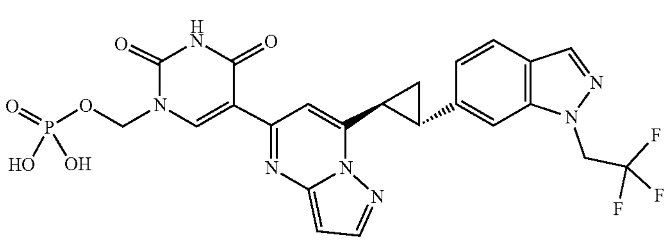 [SMILES: O=c1[nH]c(=O)n(COP(=O)(O)O)cc1-c1cc([C@H]2C[C@@H]2c2ccc3cnn(CC(F)(F)F)c3c2)n2nccc2n1] | Ex 6 | | | 10 | 85 |

TABLE 3-continued

| Structure | Compound number | FaSSIF (pH 6.5) (ug/mL) | FeSSIF (pH 5.0) (ug/mL) | Kinetic Solubility pH 1 (uM) | Kinetic Solubility pH 7 (uM) |
|---|---|---|---|---|---|
| 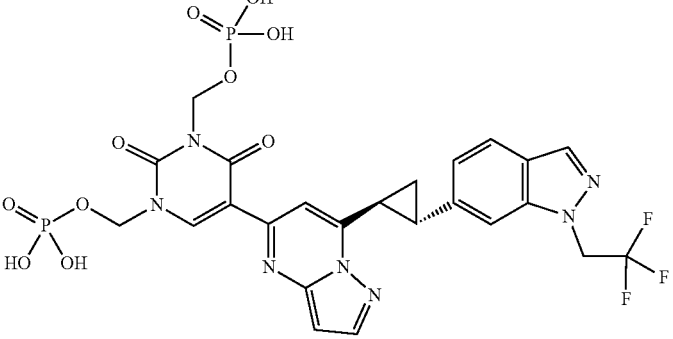 | Ex 7 | | | 89 | >100 |

Alkaline Phosphatase Stability Assay

Alkaline phosphatase stability assays were carried out using purified Bovine intestinal alkaline phosphatase. Duplicate sets were performed with a TECAN liquid handler. Assay substrate concentrations were 2 µM. Purified Bovine intestinal alkaline phosphatase was acquired through MilliPore Sigma as a lyophilized powder. Reaction mixtures were prepared by the addition of 2 µL compound (400 µM stock solution in DMSO) into wells of a 96-well plate containing 396 µL Tris buffer (100 mM, pH 7.8, 1 mM $MgCl_2$ and 1 mM $ZnCl_2$) with and without 100 ng/mL purified Bovine intestinal alkaline phosphatase. Samples were assessed at time points of 3, 30, 60, 120, 180 and 240 minutes. At each time point, 25 µL of the reaction mixtures were added into a 96-well plate containing 225 µL of quench solution (99% Acetonitrile with 1% Formic Acid and 100 nM Labetalol as internal standard). The plates containing the quench samples were then vortexed at 1100 RPM for 10 minutes and centrifuged at 4500 RPM for 20 minutes. 150 µL of the resulting supernatant was transferred into a 96-well plate containing 150 µL of water and vortexed at 1100 RPM for 3 minutes to mix.

Samples were analyzed with a Leap HTC Autosampler and a Dionex UltiMate 3000 HPLC system interfaced to a Thermo Q-Exactive mass spectrometer operating in positive ion electrospray mode. A Thermo Scientific Hypersil GOLD (1.9 µM particle size, 50×2.1 mm) HPLC column was used and mobile phase was pumped at 0.5 mL/min. Elution of analytes was achieved by a series of linear gradients of acetonitrile in water containing 0.1% (v/v) formic acid. Quantification was by analyte/internal standard peak area ratio (PAR).

TABLE 4

| Structure | Example number | ALP half life (minutes) | Assay Buffer half life (minutes) |
|---|---|---|---|
| 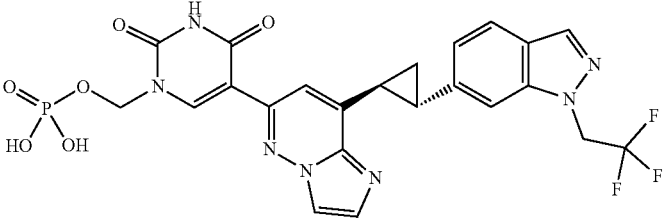 [SMILES: O=c1[nH]c(=O)n(COP(=O)(O)O)cc1-c1cc([C@H]2C[C@@H]2c2ccc3cnn(CC(F)(F)F)c3c2)c2nccn2n1] | Ex. 2 | 11 | >1584 |
| 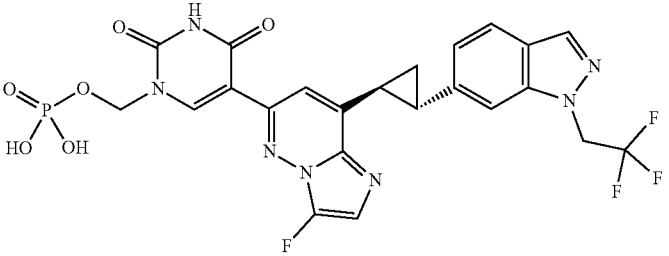 [SMILES: O=c1[nH]c(=O)n(COP(=O)(O)O)cc1-c1cc([C@H]2C[C@@H]2c2ccc3cnn(CC(F)(F)F)c3c2)c2ncc(F)n2n1] | Ex. 4 | 4 | >1584 |

TABLE 4-continued

| Structure | Example number | ALP half life (minutes) | Assay Buffer half life (minutes) |
|---|---|---|---|
| 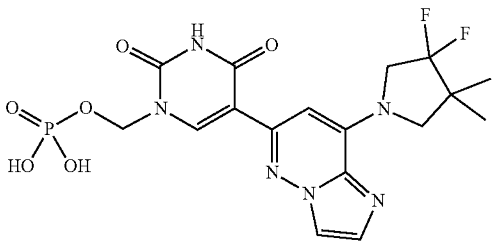 [SMILES: CC1(C)CN(c2cc(-c3cn(COP(=O)(O)O)c(=O)[nH]c3=O)nn3ccnc23)CC1(F)F] | Ex. 2 | 10 | >1584 |
| 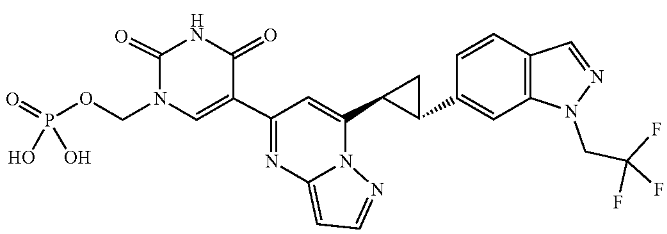 [SMILES: O=c1[nH]c(=O)n(COP(=O)(O)O)cc1-c1cc([C@H]2C[C@@H]2c2ccc3cnn(CC(F)(F)F)c3c2)n2nccc2n1] | Ex. 6 | 8 | >1584 |
| 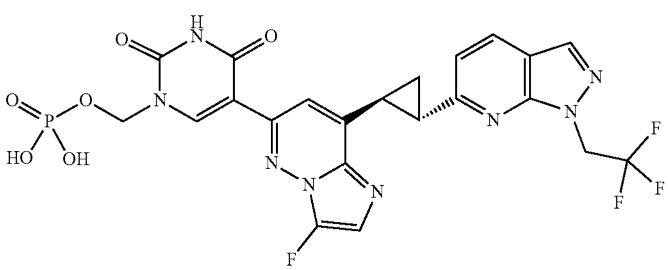 [SMILES: O=c1[nH]c(=O)n(COP(=O)(O)O)cc1-c1cc([C@H]2C[C@@H]2c2ccc3cnn(CC(F)(F)F)c3n2)c2ncc(F)n2n1] | Ex. 5 | 14 | >1584 |

In Vivo Cyno Pharmacokinetics Experiments

In vivo cyno pharmacokinetic experiments of compound Comparator B and Example 1 were assessed as follows.

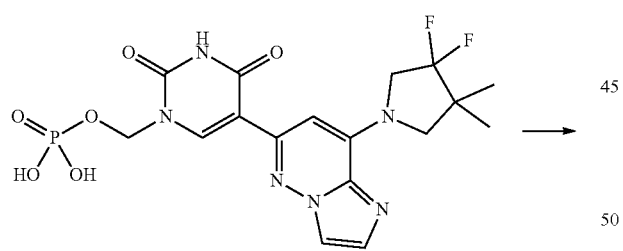

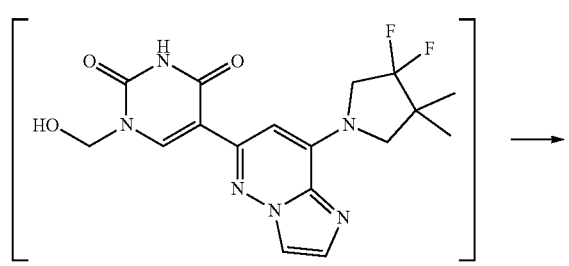

INTERMEDIATE A
(not observed)

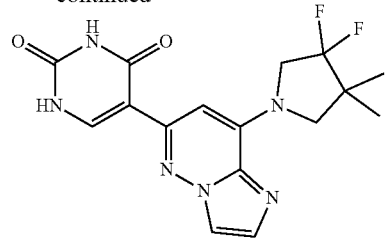

Example 1   Comparator B

Figure 2:
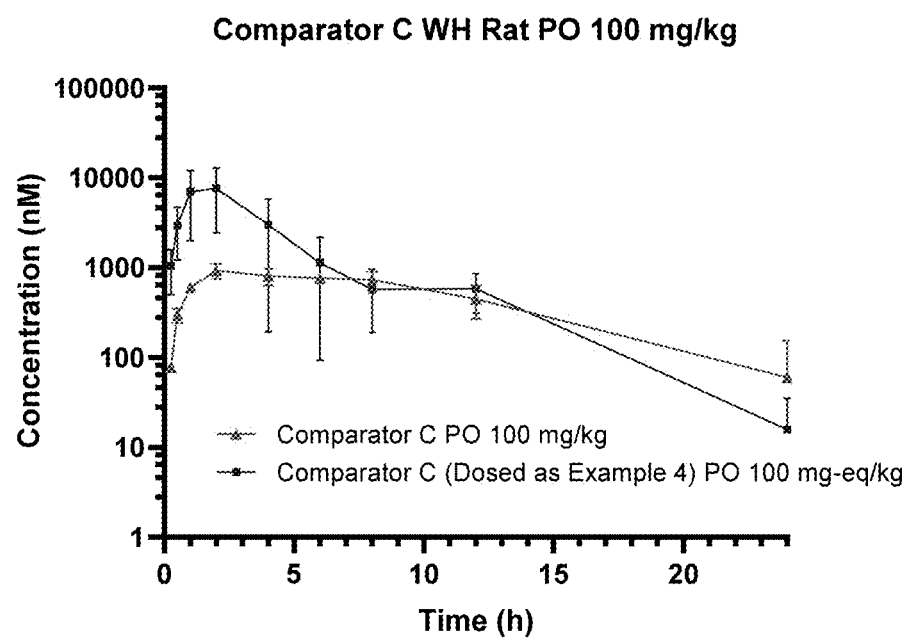
FIG. 2 shows plasma concentrations of Comparator C (nM) during a 24 hour time period after dosing with either Comparator C or Example 4.

Compound Comparator B hydrochloride salt was dosed as a 30 mg/kg suspension to cynomolgus monkeys (N=3) using the following formulation: 0.5% Methocel E4M Premium, 0.1% Tween-80, 99.4% Water. Compound Comparator B free base was dosed separately as a 12.5 mg/kg (50 mg-fixed) suspension to cynomolgus monkeys (N=3) using the following formulation: 0.5% Methocel E4M Premium, 0.1% Tween-80, 99.4% Water. Compound Example 1 was dosed separately as a 12.5 mg/kg (50 mg-fixed) suspension to cynomolgus monkeys (N=3) using the following formulation: 0.5% Methocel E4M Premium, 0.1% Tween-80, 99.4% Water. Samples were assessed for the presence of Example 1 and Comparator B. FIG. 2 shows plasma concentrations of Compound Comparator B (nM) during a 24 hour time period after dosing with either Comparator B or Example 1 using the previously described suspension for mulation. As is shown in Table 4, the AUC 0-24 h measured for Comparator B in plasma was higher after dosing with Example 1 than the value measured after dosing with an equivalent dose of Comparator B.

TABLE 5

| Structure | Compound | Dose | Comparator B AUC 0-24 h (nM-h) |
| --- | --- | --- | --- |
| 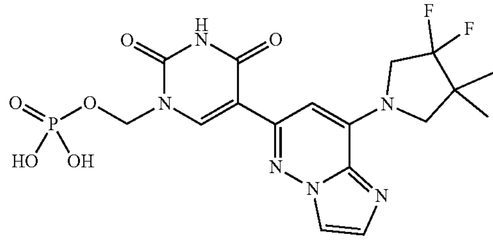 [SMILES: CC1(C)CN(c2cc(-c3cn(COP(=O)(O)O)c(=O)[nH]c3=O)nn3ccnc23)CC1(F)F] | Example 1 | 50 mg fixed (12.5 mg/kg) | 98467 |
| 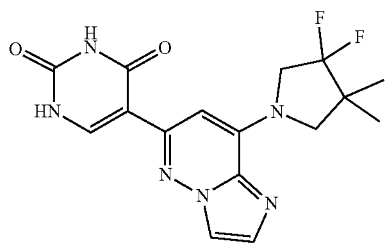 [SMILES: CC1(C)CN(c2cc(-c3c[nH]c(=O)[nH]c3=O)nn3ccnc23)CC1(F)F] | Comparator B HCl salt | 120 mg fixed (30 mg/kg) | 33167 |
| 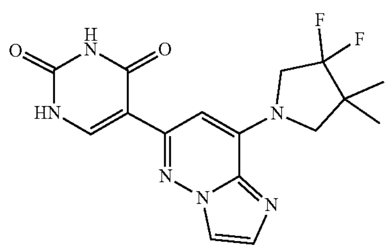 [SMILES: CC1(C)CN(c2cc(-c3c[nH]c(=O)[nH]c3=O)nn3ccnc23)CC1(F)F] | Comparator B Free Base | 50 mg fixed | 6063 |

In Vivo Rat Pharmacokinetics Experiments

In vivo Wister Han rat pharmacokinetic experiments of compound Comparator C and Example 4 were assessed as follows.

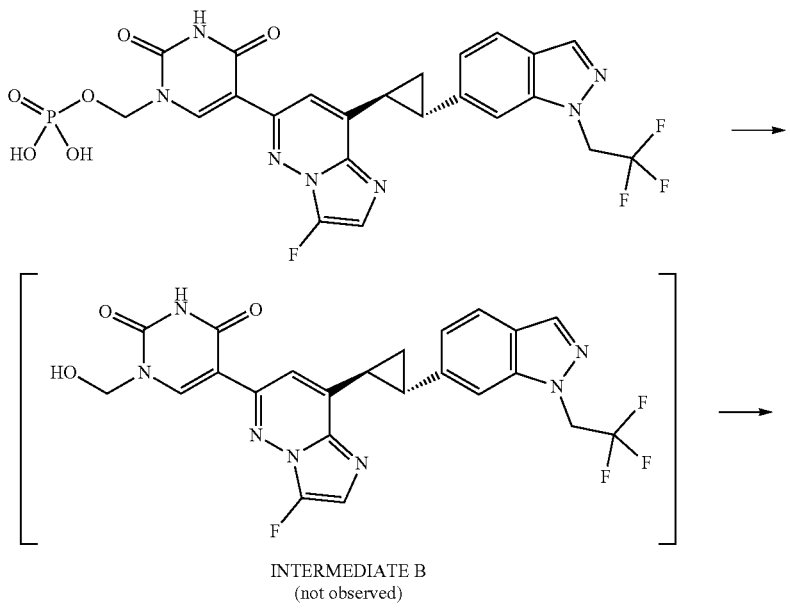

INTERMEDIATE B
(not observed)

-continued

Example 4 Comparator C

Compound Comparator C was dosed as a 100 mg/kg suspension to Wister Han rats (N=3) using the following formulation: 30% captisol, 5% soluplus, 65% pH 2 water. Compound 1170997 was dosed separately as a 100 mg-eq/kg (123 mg/kg) solution to Wister Han rats (N=3) using the following formulation: 0.5% Methocel E4M Premium, 0.1% Tween-80, 99.4% Water. Samples were assessed for the presence of Comparator C.

Comparator C and Example 4. FIG. 2 shows plasma concentrations of Comparator C (nM) during a 24 hour time period after dosing with either Comparator C or Example 4 using the previously described solution formulation. As is shown in Table 4, the AUC 0-24 h measured for Comparator C in plasma was higher after dosing with Example 4 than the value measured after dosing with an equivalent dose of Comparator C.

What is claimed is:

1. A compound of Formula I:

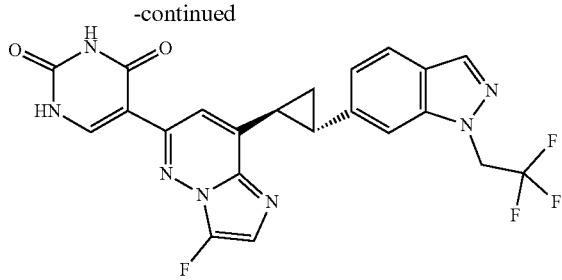

I

| Structure | Compound | Dose | Comparator C AUC 0-24 h (nM-h) |
|---|---|---|---|
| 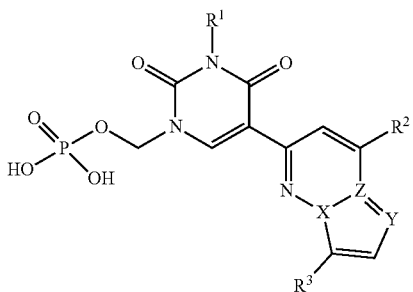 | Ex. 4 | 100 mg-eq/kg | 32800 |
| 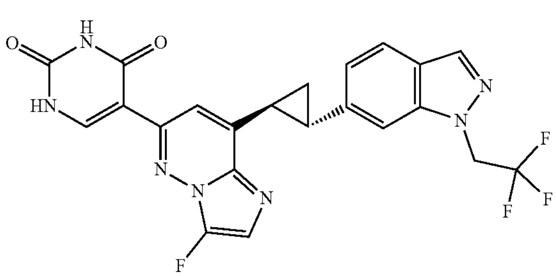 [SMILES: O=c1[nH]cc(-c2cc([C@H]3C[C@@H]3c3ccc4cnn(CC(F)(F)F)c4c3)c3ncc(F)n3n2)c(=O)[nH]1] | Comparator C HCl salt | 100 mg/kg | 11200 |

Or a pharmaceutically acceptable salt thereof, wherein:
  X is C or N,
  Y is CH or N;
  Z is C or N;
  provided that one of X, Y and Z is CH or C, and two of X, Y and Z are N;
  $R^1$ is selected from H and $CH_2OP(O)(OH)_2$;
  $R_2$ is a $C_{3-6}$ cycloalkyl or a 3-8 membered heterocyclyl; wherein said cycloalkyl and said heterocyclyl are substituted with one or more $R^4$,
  $R^3$ is H or halo;
  $R^4$ is independently selected from H, halo, $C_{1-4}$ alkyl, $-OR^5$, $C_{6-10}$ aryl, or 4-10 membered heteroaryl; wherein said $C_{1-4}$ alkyl, $C_{6-10}$ aryl, or 4-10 membered heteroaryl is optionally substituted with one or more $R^6$;
  $R^5$ is $C_{1-5}$ alkyl, $C_{1-5}$ alkenyl, $C_{1-5}$ alkynyl, said $C_{1-5}$ alkyl, $C_{1-5}$ alkenyl, $C_{1-5}$ alkynyl, $C_{6-10}$ aryl, or 4-10 membered heteroaryl and is optionally substituted with one or more $R^6$ and halo;
  $R^6$ is a $C_{1-5}$ alkyl, $C_{3-6}$ cycloalkyl, $C_{1-5}$ alkenyl, $C_{1-5}$ alkynyl, or 4-10 membered heteroaryl, said $C_{1-5}$ alkyl, $C_{3-6}$ cycloalkyl, $C_{1-5}$ alkenyl, or $C_{1-5}$ alkynyl is optionally substituted with halo, and said 4-10 membered heteroaryl optionally substituted with $C_{1-4}$ alkyl, or $C_{1-4}$ haloalkyl.

2. The compound of claim 1 wherein $R^1$ is H.

3. The compound of claim 1 wherein $R^1$ is $CH_2OP(O)(OH)_2$.

4. The compound of claim 1, wherein $R^2$ is a $C_{3-6}$ cycloalkyl substituted with one or more $R^4$.

5. The compound of claim 1, wherein $R^2$ is a 3-8 membered heterocyclyl substituted with one or more $R^4$.

6. The compound of claim 1, wherein $R^2$ is cyclopropyl substituted with one or more $R^4$.

7. The compound of claim 1, wherein $R^4$ is a 4-10 membered heteroaryl, optionally substituted with one or more $R^6$.

8. The compound of claim 7, wherein $R^4$ is a 4-10 membered heteroaryl, substituted with one or more $R^6$.

9. The compound of claim 8, wherein $R^4$ is a 4-10 membered heteroaryl, substituted with one or more $C_{1-5}$ alkyl, said $C_{1-5}$ alkyl optionally substituted with halo.

10. The compound of claim 9, wherein $R^4$ is a 4-10 membered heteroaryl, substituted with one or more $C_{1-5}$ alkyl, said $C_{1-5}$ alkyl substituted with one or more halo.

11. The compound of claim 10, wherein $R^4$ is a 4-10 membered heteroaryl, substituted with one or more $C_{1-5}$ alkyl, said $C_{1-5}$ alkyl substituted with one or more fluoro.

12. The compound of claim 11, wherein $R^4$ is indazole, substituted with one or more $C_{1-5}$ alkyl, said $C_{1-5}$ alkyl substituted with one or more fluoro.

13. The compound of claim 12, wherein $R^4$ is indazole, substituted with one $C_{1-5}$ alkyl, said $C_{1-5}$ alkyl substituted with one or more fluoro.

14. The compound of claim 13, wherein $R^4$ is indazole, substituted with trifluoroethyl.

15. The compound of claim 14, wherein $R^3$ is H.

16. The compound of claim 14, wherein $R^3$ is halo.

17. The compound of claim 16, wherein $R^3$ is F.

18. The compound of claim 13, or a pharmaceutically acceptable salt thereof, selected from the group consisting of:

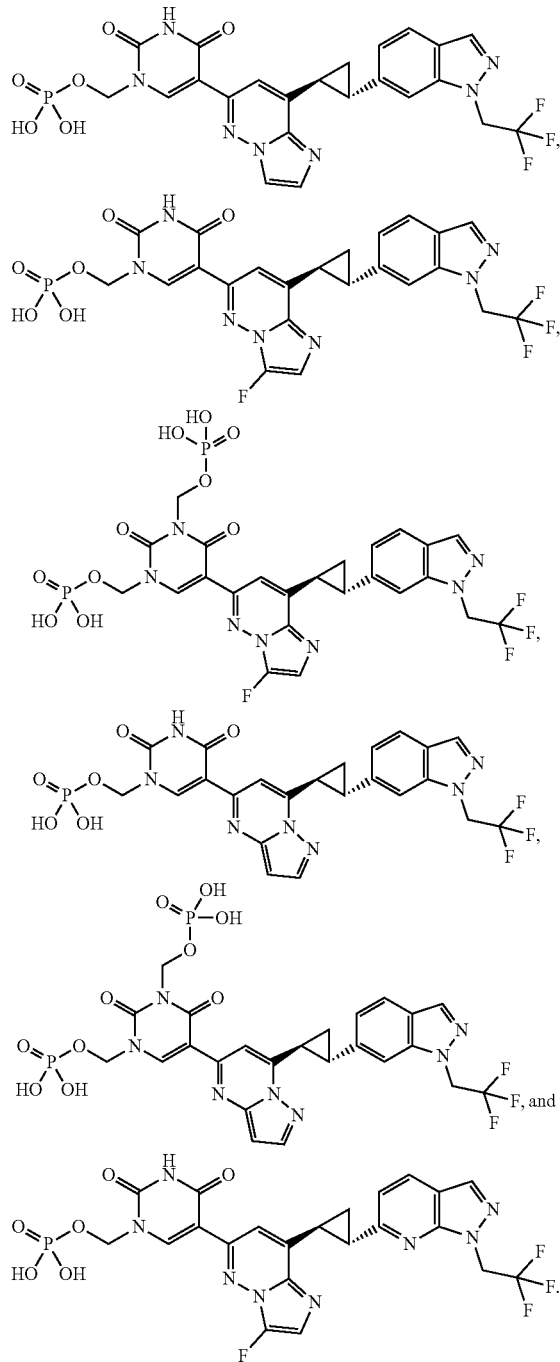

19. The compound of claim 1, wherein $R^2$ is a 3-8 membered heterocyclyl; wherein said heterocyclyl is substituted with one or more $R^4$.

20. The compound of claim 19, wherein $R^2$ is pyrrolidinyl, substituted with one or more $R^4$.

21. The compound of claim 20, wherein said pyrrolidinyl is substituted with two fluoro groups and $-OR^5$.

22. The compound of claim 21, wherein $R^5$ is a 4-10 membered heteroaryl and is optionally substituted with one or more $R^6$ and halo.

23. The compound of claim 20, wherein said pyrrolidinyl is independently substituted with four $R^4$.

24. The compound of claim 23, wherein said pyrrolidinyl is substituted with two methyl and two fluoro groups.

25. The compound of claim 24, wherein said pyrrolidinyl is gem dimethyl substituted.

26. The compound of claim 20, or a pharmaceutically acceptable salt thereof, selected from the group consisting of:

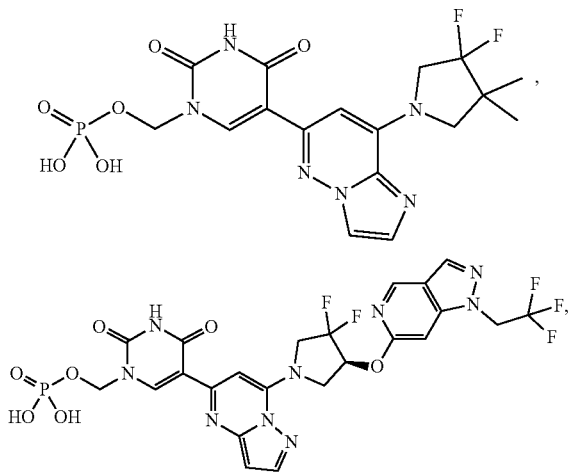

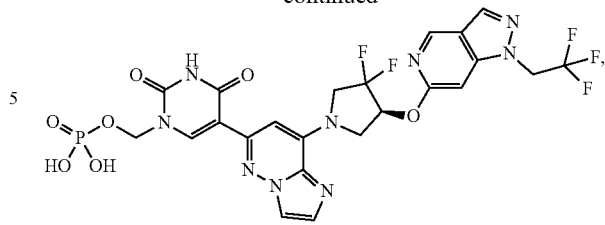

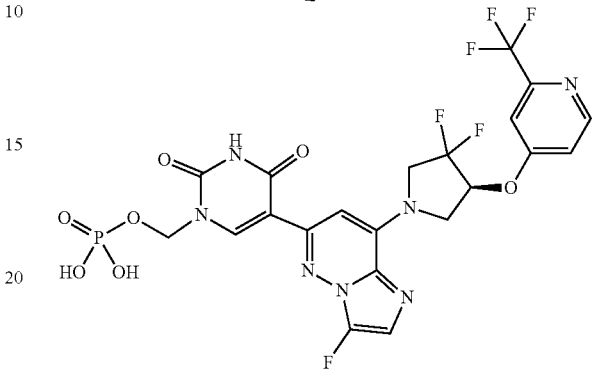

or a pharmaceutically acceptable salt thereof.

27. A pharmaceutical composition comprising a compound of any of claims 1-26, together with a pharmaceutically acceptable carrier.

* * * * *